(12) United States Patent
Xie et al.

(10) Patent No.: US 12,392,766 B2
(45) Date of Patent: Aug. 19, 2025

(54) NANOPORE SENSING DEVICE, COMPONENTS AND METHOD OF OPERATION

(71) Applicant: Oxford Nanopore Technologies PLC, Oxford (GB)

(72) Inventors: Ping Xie, Needham, MA (US); Justin Millis, Oxford (GB); Ken Healy, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 0 days.

(21) Appl. No.: 18/459,592

(22) Filed: Sep. 1, 2023

(65) Prior Publication Data

US 2024/0069007 A1 Feb. 29, 2024

Related U.S. Application Data

(63) Continuation of application No. 16/816,221, filed on Mar. 11, 2020, now Pat. No. 11,789,006.
(Continued)

(51) Int. Cl.
*G01N 33/487* (2006.01)
*G01N 27/12* (2006.01)

(52) U.S. Cl.
CPC ..... *G01N 33/48721* (2013.01); *G01N 27/128* (2013.01)

(58) Field of Classification Search
CPC .................. G01N 27/128; G01N 33/48721
See application file for complete search history.

(56) References Cited

U.S. PATENT DOCUMENTS

| 3,799,743 A | 3/1974 | Alexander et al. |
| 4,154,795 A | 5/1979 | Thorne |

(Continued)

FOREIGN PATENT DOCUMENTS

| AU | 2003240941 A1 | 12/2003 |
| CN | 1500555 A | 6/2004 |

(Continued)

OTHER PUBLICATIONS

U.S. Appl. No. 17/665,011, filed Feb. 4, 2022, Brown et al.
(Continued)

*Primary Examiner* — Judy Nguyen
*Assistant Examiner* — Adam S Clarke
(74) *Attorney, Agent, or Firm* — Wolf, Greenfield & Sacks, P.C.

(57) ABSTRACT

Devices for improved nanopore sensing are described. An example device has a structure arranged to separate an analyte reservoir and an outlet chamber. An example device has a structure arranged to separate an analyte reservoir and an outlet chamber. The structure can include an array of nanopore structures, each nanopore structure comprising a passage for fluid connection through the structure between the analyte reservoir and outlet chamber. Control terminals can be arranged for applying a control signal to alter the electrical potential difference across that nanopore structure. Some embodiments include an electronic circuit configured to detect a signal from an electrical transduction element at each nanopore structure. Additional structural features and methods of operating and making the devices are described.

19 Claims, 15 Drawing Sheets

Related U.S. Application Data

(60) Provisional application No. 62/817,211, filed on Mar. 12, 2019.

(56) References Cited

U.S. PATENT DOCUMENTS

| | | | |
|---|---|---|---|
| 4,874,500 A | 10/1989 | Madou et al. | |
| 5,234,566 A | 8/1993 | Osman et al. | |
| 5,290,240 A | 3/1994 | Horres, Jr. | |
| 5,403,451 A | 4/1995 | Riviello et al. | |
| 5,503,803 A | 4/1996 | Brown et al. | |
| 6,056,922 A | 5/2000 | Ikematsu | |
| 6,300,141 B1 | 10/2001 | Segal et al. | |
| 6,479,288 B1 | 11/2002 | Laffafian et al. | |
| 6,483,931 B2 | 11/2002 | Kalnitsky et al. | |
| 6,503,452 B1 | 1/2003 | Boxer et al. | |
| 6,699,697 B2 | 3/2004 | Klemic et al. | |
| 6,863,833 B1 | 3/2005 | Bloom et al. | |
| 6,913,697 B2 | 7/2005 | Lopez et al. | |
| 6,916,488 B1 | 7/2005 | Meier et al. | |
| 7,077,939 B1 | 7/2006 | Crooks et al. | |
| 7,144,486 B1 | 12/2006 | Fritsch et al. | |
| 7,169,272 B2 | 1/2007 | Fritsch et al. | |
| 7,745,116 B2 | 6/2010 | Williams | |
| 7,939,270 B2 | 5/2011 | Holden et al. | |
| 8,124,191 B2 | 2/2012 | Ervin et al. | |
| 8,197,775 B2 | 6/2012 | Johnston et al. | |
| 8,461,854 B2 | 6/2013 | Chen et al. | |
| 9,057,102 B2 | 6/2015 | Turner et al. | |
| 9,546,400 B2 | 1/2017 | Turner et al. | |
| 9,556,480 B2 | 1/2017 | Turner et al. | |
| 9,613,247 B2 | 4/2017 | Yang | |
| 9,678,056 B2 | 6/2017 | Turner et al. | |
| 9,734,382 B2 | 8/2017 | Wang et al. | |
| 9,738,929 B2 | 8/2017 | Turner et al. | |
| 9,927,398 B2 | 3/2018 | Reid et al. | |
| 10,036,065 B2 | 7/2018 | Jones | |
| 10,215,768 B2 | 2/2019 | Sanghera et al. | |
| 10,338,056 B2 | 7/2019 | Hyde et al. | |
| 10,416,117 B2 | 9/2019 | Reid et al. | |
| 10,549,274 B2 | 2/2020 | Brown et al. | |
| 10,814,298 B2 | 10/2020 | Hyde et al. | |
| 11,084,015 B2 | 8/2021 | Hyde et al. | |
| 11,097,269 B2 | 8/2021 | Goto et al. | |
| 11,561,216 B2 | 1/2023 | Hyde et al. | |
| 11,596,940 B2 | 3/2023 | Waterman | |
| 11,789,006 B2 | 10/2023 | Xie et al. | |
| 11,913,936 B2 | 2/2024 | Hyde et al. | |
| 12,121,894 B2 | 10/2024 | Waterman | |
| 2002/0074227 A1 | 6/2002 | Nisch et al. | |
| 2002/0123048 A1 | 9/2002 | Gau | |
| 2002/0144905 A1 | 10/2002 | Schmidt | |
| 2003/0015422 A1 | 1/2003 | Fritsch et al. | |
| 2003/0075445 A1 | 4/2003 | Woudenberg et al. | |
| 2003/0098248 A1 | 5/2003 | Vogel et al. | |
| 2003/0111340 A1 | 6/2003 | Cheng et al. | |
| 2003/0148401 A1 | 8/2003 | Agrawal et al. | |
| 2003/0224523 A1 | 12/2003 | Thornberg et al. | |
| 2004/0022677 A1 | 2/2004 | Wohlstadter et al. | |
| 2004/0096358 A1 | 5/2004 | Blankstein et al. | |
| 2004/0171169 A1 | 9/2004 | Kallury et al. | |
| 2005/0014162 A1 | 1/2005 | Barth et al. | |
| 2005/0133101 A1 | 6/2005 | Chung et al. | |
| 2005/0230272 A1 | 10/2005 | Lee et al. | |
| 2005/0279634 A1 | 12/2005 | Ozaki et al. | |
| 2006/0079009 A1 | 4/2006 | Salmon et al. | |
| 2006/0163063 A1 | 7/2006 | Picollet-Dahan et al. | |
| 2006/0194331 A1 | 8/2006 | Pamula et al. | |
| 2006/0257941 A1 | 11/2006 | McDevitt et al. | |
| 2007/0035308 A1 | 2/2007 | Ide | |
| 2007/0161101 A1 | 7/2007 | Takeuchi | |
| 2007/0275480 A1 | 11/2007 | Brander et al. | |
| 2008/0254995 A1 | 10/2008 | Kim et al. | |
| 2009/0072332 A1 | 3/2009 | Dekker et al. | |
| 2009/0142504 A1 | 6/2009 | Ervin et al. | |
| 2009/0167288 A1 | 7/2009 | Reid et al. | |
| 2010/0035349 A1 | 2/2010 | Bau et al. | |
| 2010/0147450 A1 | 6/2010 | Takeuchi et al. | |
| 2010/0188109 A1* | 7/2010 | Edel | G01N 33/48721 174/250 |
| 2010/0190253 A1 | 7/2010 | Tazaki et al. | |
| 2010/0196203 A1 | 8/2010 | Sanghera et al. | |
| 2010/0304980 A1 | 12/2010 | Takeuchi et al. | |
| 2011/0120871 A1 | 5/2011 | Reid et al. | |
| 2011/0121840 A1 | 5/2011 | Sanghera et al. | |
| 2011/0133255 A1 | 6/2011 | Merz | |
| 2011/0214991 A1 | 9/2011 | Kim et al. | |
| 2011/0274737 A1 | 11/2011 | Palmaz | |
| 2011/0287414 A1 | 11/2011 | Chen et al. | |
| 2011/0318774 A1 | 12/2011 | Larsen | |
| 2012/0010085 A1 | 1/2012 | Rava et al. | |
| 2013/0048499 A1 | 2/2013 | Mayer et al. | |
| 2013/0071932 A1 | 3/2013 | Itchoda et al. | |
| 2013/0140192 A1 | 6/2013 | Behrends et al. | |
| 2013/0196442 A1 | 8/2013 | Momose et al. | |
| 2013/0207205 A1 | 8/2013 | Chen | |
| 2013/0217106 A1 | 8/2013 | Jones et al. | |
| 2013/0270521 A1 | 10/2013 | Peng et al. | |
| 2013/0309776 A1 | 11/2013 | Drndic et al. | |
| 2014/0174927 A1 | 6/2014 | Bashir et al. | |
| 2014/0190833 A1 | 7/2014 | Lieber et al. | |
| 2014/0243214 A1 | 8/2014 | Haga et al. | |
| 2014/0255921 A1 | 9/2014 | Moysey et al. | |
| 2014/0296083 A1 | 10/2014 | Brown et al. | |
| 2014/0318964 A1 | 10/2014 | Dunbar et al. | |
| 2014/0329693 A1 | 11/2014 | Reid et al. | |
| 2014/0335512 A1 | 11/2014 | Moysey et al. | |
| 2014/0346059 A1 | 11/2014 | Akeson | |
| 2014/0346515 A1 | 11/2014 | Yanagi et al. | |
| 2015/0014160 A1 | 1/2015 | Hyde et al. | |
| 2015/0027885 A1 | 1/2015 | Rajaraman et al. | |
| 2015/0028846 A1* | 1/2015 | Zhu | G01N 33/48721 977/773 |
| 2015/0065354 A1 | 3/2015 | Moysey et al. | |
| 2015/0191709 A1 | 7/2015 | Heron et al. | |
| 2015/0198611 A1 | 7/2015 | Ostrowski et al. | |
| 2015/0204763 A1 | 7/2015 | Stelzle et al. | |
| 2015/0218629 A1 | 8/2015 | Heron et al. | |
| 2015/0232923 A1 | 8/2015 | Drndic et al. | |
| 2015/0259724 A1 | 9/2015 | Guan et al. | |
| 2015/0265994 A1 | 9/2015 | Hyde et al. | |
| 2015/0268256 A1 | 9/2015 | Sanghera et al. | |
| 2015/0300986 A1 | 10/2015 | Reid et al. | |
| 2016/0040230 A1 | 2/2016 | Akeson | |
| 2016/0178576 A1 | 6/2016 | Maney et al. | |
| 2016/0231307 A1 | 8/2016 | Xie | |
| 2016/0257942 A1 | 9/2016 | Bruce et al. | |
| 2017/0189906 A1 | 7/2017 | Moll et al. | |
| 2017/0326550 A1 | 11/2017 | Brown et al. | |
| 2017/0363577 A1 | 12/2017 | Reid et al. | |
| 2018/0321188 A1 | 11/2018 | Reid et al. | |
| 2018/0372713 A1 | 12/2018 | Stamm et al. | |
| 2019/0210021 A1 | 7/2019 | Waterman | |
| 2019/0242913 A1 | 8/2019 | Sanghera et al. | |
| 2019/0352709 A1* | 11/2019 | Clarke | C12Q 1/6869 |
| 2019/0391128 A1 | 12/2019 | Hyde et al. | |
| 2020/0292521 A1 | 9/2020 | Xie et al. | |
| 2021/0086160 A1 | 3/2021 | Hyde et al. | |
| 2021/0170403 A1 | 6/2021 | Waterman | |
| 2021/0300750 A1 | 9/2021 | Waterman | |
| 2022/0023819 A1 | 1/2022 | Hyde et al. | |
| 2023/0228733 A1 | 7/2023 | Hyde et al. | |
| 2023/0258592 A1* | 8/2023 | Bedau | G01N 27/228 324/686 |
| 2023/0311118 A1 | 10/2023 | Waterman | |
| 2023/0349882 A1 | 11/2023 | Xie et al. | |

FOREIGN PATENT DOCUMENTS

| | | |
|---|---|---|
| CN | 101078704 | 11/2007 |
| CN | 100448007 C | 12/2008 |
| CN | 101490277 A | 7/2009 |
| CN | 100571871 C | 12/2009 |
| CN | 102263104 A | 11/2011 |
| CN | 203466320 U | 9/2013 |

(56) References Cited

FOREIGN PATENT DOCUMENTS

| | | |
|---|---|---|
| CN | 103370617 A | 10/2013 |
| CN | 103995035 A | 8/2014 |
| CN | 205828393 U | 12/2016 |
| CN | 106457247 A | 2/2017 |
| DE | 102010022929 A1 | 12/2011 |
| EP | 0532215 A2 | 3/1993 |
| EP | 1110084 A1 | 6/2001 |
| EP | 1120469 A2 | 8/2001 |
| EP | 1419818 A1 | 5/2004 |
| EP | 1535667 A1 | 6/2005 |
| EP | 1669746 A1 | 6/2006 |
| EP | 1677102 | 7/2006 |
| EP | 1688742 | 8/2006 |
| EP | 1710578 | 10/2006 |
| EP | 1712909 A1 | 10/2006 |
| EP | 1779921 A1 | 5/2007 |
| EP | 2219032 A1 | 8/2010 |
| GB | 2237390 | 5/1991 |
| GB | 2446823 | 8/2008 |
| JP | S5-274882 A | 6/1977 |
| JP | H04-215052 A | 8/1992 |
| JP | 7307172 A2 | 11/1995 |
| JP | 2004-158330 A2 | 6/2004 |
| JP | 2005-098718 | 4/2005 |
| JP | 2005-164276 A | 6/2005 |
| JP | 2005-300460 A | 10/2005 |
| JP | 2005-539242 A | 12/2005 |
| JP | 2006-312141 A | 11/2006 |
| JP | 2008-194573 A | 8/2008 |
| JP | 2009-128206 A | 6/2009 |
| JP | 2010-186677 A2 | 8/2010 |
| JP | 2012-247231 A | 12/2012 |
| JP | 2013-148425 A | 8/2013 |
| JP | 2013-242247 A | 12/2013 |
| JP | 2014-190891 A | 10/2014 |
| JP | 2014-529296 A | 11/2014 |
| JP | 2015-064373 A | 4/2015 |
| JP | 2018-510329 A | 4/2018 |
| KR | 10-2017-0012367 | 2/2017 |
| WO | WO 1988/008534 A1 | 11/1988 |
| WO | WO 1994/025862 A1 | 11/1994 |
| WO | WO 1997/016545 A1 | 5/1997 |
| WO | WO 1998/058248 | 12/1998 |
| WO | WO 1999/013101 A1 | 3/1999 |
| WO | WO 2000/013014 A1 | 3/2000 |
| WO | WO 2000/025121 A1 | 5/2000 |
| WO | WO 2001/059447 A1 | 8/2001 |
| WO | WO 2002/024862 A2 | 3/2002 |
| WO | WO 2002/029402 A2 | 4/2002 |
| WO | WO 2002/035221 A1 | 5/2002 |
| WO | WO 2002/082046 A2 | 10/2002 |
| WO | WO 2003/052420 A2 | 6/2003 |
| WO | WO 2005/040783 A1 | 5/2005 |
| WO | WO 2005/124888 A1 | 12/2005 |
| WO | WO 2006/012571 A1 | 2/2006 |
| WO | WO 2006/076703 A2 | 7/2006 |
| WO | WO 2006/100484 | 9/2006 |
| WO | WO 2006/104639 | 10/2006 |
| WO | WO 2006/113550 | 10/2006 |
| WO | WO 2006/138160 A2 | 12/2006 |
| WO | WO 2007/028003 A2 | 3/2007 |
| WO | WO 2007/049576 A1 | 5/2007 |
| WO | WO 2007/116978 A1 | 10/2007 |
| WO | WO 2007/127327 | 11/2007 |
| WO | WO 2007/132002 A1 | 11/2007 |
| WO | WO 2008/012552 A1 | 1/2008 |
| WO | WO 2008/054611 A2 | 5/2008 |
| WO | WO 2008/102120 | 8/2008 |
| WO | WO 2008/102121 | 8/2008 |
| WO | WO 2008/124107 A1 | 10/2008 |
| WO | WO 2008/137008 A2 | 11/2008 |
| WO | WO 2008/156041 A1 | 12/2008 |
| WO | WO 2009/024775 A1 | 2/2009 |
| WO | WO 2009/035647 A1 | 3/2009 |
| WO | WO 2009/077734 A2 | 6/2009 |
| WO | WO 2010/122293 | 10/2010 |
| WO | WO 2010/142954 A1 | 12/2010 |
| WO | WO 2011/046706 A1 | 4/2011 |
| WO | WO 2011/067559 A1 | 6/2011 |
| WO | WO 2011/118211 A1 | 9/2011 |
| WO | WO 2011/154114 A2 | 12/2011 |
| WO | WO 2012/033524 A2 | 3/2012 |
| WO | WO 2012/042226 A2 | 4/2012 |
| WO | WO 2012/138357 A1 | 10/2012 |
| WO | WO 2013/012881 A2 | 1/2013 |
| WO | WO 2013/021815 A1 | 2/2013 |
| WO | WO 2013/041878 A1 | 3/2013 |
| WO | WO 2013/057495 A2 | 4/2013 |
| WO | WO 2013/121193 A2 | 8/2013 |
| WO | WO 2013/121224 A1 | 8/2013 |
| WO | WO 2013/123379 A2 | 8/2013 |
| WO | WO 2014/019603 A1 | 2/2014 |
| WO | WO 2014/064443 A2 | 5/2014 |
| WO | WO 2014/064444 A1 | 5/2014 |
| WO | WO 2014/132343 A1 | 9/2014 |
| WO | WO 2015/183871 A1 | 12/2015 |
| WO | WO 2015/193076 A1 | 12/2015 |
| WO | WO 2016/059427 A1 | 4/2016 |
| WO | WO 2016/127007 A2 | 8/2016 |
| WO | WO 2016/172724 A1 | 10/2016 |
| WO | WO 2016/187519 A1 | 11/2016 |
| WO | WO 2017/061600 A1 | 4/2017 |
| WO | WO 2018/007819 A1 | 1/2018 |
| WO | WO 2019/063959 A1 | 4/2019 |
| WO | WO 2019/160925 A1 | 8/2019 |
| WO | WO 2020/183172 A1 | 9/2020 |

OTHER PUBLICATIONS

U.S. Appl. No. 17/665,035, filed Feb. 4, 2022, Brown et al.
PCT/GB2020/050606, Aug. 25, 2020, International Search Reprort and Written Opinion.
PCT/GB2020/050606, Sep. 23, 2021, International Preliminary Report on Patentability.
International Search Report and Written Opinion for Application No. PCT/GB2020/050606, mailed Aug. 25, 2020.
International Preliminary Report on Patentability for Application No. PCT/GB2020/050606, mailed Sep. 23, 2021.
Third Party Observations for EP 17739663.7, mailed Sep. 23, 2021. 18 pages.
[No Author Listed] Avanti Polar Lipids, Inc. Avanti Polar Lipids-Preparations of Liposomes. Www.avantilipids.com 5 pages. Jul. 1, 2014.
Aghdaei et al., Formation of artificial lipid bilayers using droplet dielectrophoresis. Lab Chip. Oct. 2008;8(10):1617-20. doi: 10.1039/b807374k. Epub Aug. 13, 2008.
Altschul et al., Basic local alignment search tool. J Mol Biol. Oct. 5, 1990;215(3):403-10.
Altschul, A protein alignment scoring system sensitive at all evolutionary distances. J Mol Evol. Mar. 1993;36(3):290-300.
Anrather et al., Supported membrane nanodevices. J Nanosci Nanotechnol. Jan.-Feb. 2004;4(1-2):1-22.
Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.
Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.
Bezrukov et al., Counting polymers moving through a single ion channel. Nature. Jul. 28, 1994;370(6487):279-81.
Bouaidat et al., Surface-directed capillary system; theory, experiments and applications. Lab Chip. Aug. 2005;5(8):827-36. Epub Jul. 1, 2005.
Bruggemann et al., Microchip technology for automated and parallel patch-clamp recording. Small. Jul. 2006;2(7):840-6.
Bull et al., Polymer Films on Electrodes. J. Electrochem Soc. May 1982;129(5):1009-1015.

(56) References Cited

OTHER PUBLICATIONS

Cheng et al., Discrete membrane arrays. J Biotechnol. Sep. 2000;74(3):159-74.
Cheng et al., Single Ion Channel Sensitivity in Suspended Bilayers on Micromachined Supports. Langmuir. 2001;17(4):1240-1242.
Danelon et al., Cell membranes suspended across nanoaperture arrays. Langmuir. Jan. 3, 2006;22(1):22-5.
Devereux et al., A comprehensive set of sequence analysis programs for the VAX. Nucleic Acids Res. Jan. 11, 1984;12(1 Pt 1):387-95.
Estes et al., Electroformation of giant liposomes from spin-coated films of lipids. Colloids Surf B Biointerfaces. May 10, 2005;42(2):115-23.
Fraikin et al., A high-throughput label-free nanoparticle analyser. Nat Nanotechnol. 2011;6(5):308-313. doi:10.1038/nnano.2011.24.
Funakoshi et al., Lipid bilayer formation by contacting monolayers in a microfluidic device for membrane protein analysis. Anal Chem. Dec. 15, 2006;78(24):8169-74.
Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.
Gonzalez-Perez et al., Biomimetic triblock copolymer membrane arrays: a stable template for functional membrane proteins. Langmuir. 2009;25(18):10447-10450. doi:10.1021/la902417m.
Hasanzadeh et al., Room-temperature ionic liquid-based electrochemical nanobiosensors. Trends Anal Chem. Dec. 2012;41:58-74.
Heron et al., Simultaneous measurement of ionic current and fluorescence from single protein pores. J Am Chem Soc. Feb. 11, 2009;131(5):1652-3. doi: 10.1021/ja808128s.
Hirano et al., Lipid Bilayers at Gel/Gel Interface for Ion Channel Recordings. Surf. Sci. Nanotech. 2008;6:130-133.
Holden et al., Functional bionetworks from nanoliter water droplets. J Am Chem Soc. Jul. 11, 2007;129(27):8650-5. Epub Jun. 16, 2007.
Horn, Avoiding Evaporation. Ibidi. Application Note 12. Mar. 29, 2012, pp. 1-3.
Hovis et al., Patterning and Composition Arrays of Supported Lipid Bilayers by Microcontact Printing. Langmuir. 2001;17:3400-3405.
Hromada et al., Single molecule measurements within individual membrane-bound ion channels using a polymer-based bilayer lipid membrane chip. Lab Chip. Apr. 2008;8(4):602-8. doi: 10.1039/b716388f. Epub Feb. 29, 2008.
Ide et al., A novel method for artificial lipid-bilayer formation. Biosens Bioelectron. Oct. 15, 2005;21(4):672-7. Epub Jan. 26, 2005.
Ikariyama et al., Polypyrrole electrode as a detector for electroinactive anions by flow injection analysis. Anal. Chem. 1986, 58, 8, 1803-1806.
Ivanov et al., DNA tunneling detector embedded in a nanopore. Nano Lett. 2011;11(1):279-285. doi: 10.1021/nl103873a.
Jeon et al., Long-term storable and shippable lipid bilayer membrane platform. Lab Chip. Oct. 2008;8(10):1742-4. doi: 10.1039/b807932c. Epub Aug. 22, 2008.
Jung et al., Detecting protein-ligand binding on supported bilayers by local pH modulation. J Am Chem Soc. Jan. 28, 2009;131(3):1006-14. doi: 10.1021/ja804542p. Author Manuscript, 23 pages.
Kam et al., Spatially Selective Manipulation of Supported Lipid Bilayers by Laminar Flow: Steps Toward Biomembrane Microfluidic. Langmuir. 2003;19(5):1624-1631.
Kasianowicz et al., Protonation dynamics of the alpha-toxin ion channel from spectral analysis of pH-dependent current fluctuations. Biophys J. Jul. 1995;69(1):94-105.
Kim et al., Liquid-slate field-effect transistors using electrowetting. Applied Physics Letters. 90:043507-1-043507-3.
Krantz Lab. Planar Lip Bilayer Electrophysiology Equipment. Department of Molecular & Cell Biology, University of California, Berkeley. Oct. 6, 2007. Last accessed at mcb.berkeley.edu/labs/krantz/equipment/blm.html on Nov. 26, 2014.
Kung et al., Printing via Photolithography on Micropartitioned Fluid Lipid Membranes. Adv. Materials. 2000;12(10):731-734.
Langecker et al., Synthetic lipid membrane channels formed by designed DNA nanostructures. Science. Nov. 16, 2012;338(6109):932-6. doi: 10.1126/science.1225624.
Le Pioufle et al., Lipid bilayer microarray for parallel recording of transmembrane ion currents. Anal Chem. Jan. 1, 2008;80(1):328-32. Epub Nov. 15, 2007.
Lee et al., Ion channel switch array: A biosensor for detecting multiple pathogens. Industrial Biotechnology. May 2005;1(1):26-31. doi:10.1089/ind.2005.1.26.
Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.
Lee et al., Polyelectrolyte Micropatterning Using Agarose Plane Stamp and a Substrate Having Microscale Features on Its Surface. Bull. Korean Chem. Soc., vol. 26(10):1539-1542 (2005).
Lewis et al., The Mesomorphic Phase Behavior of Lipid Bilayers. Structure Biological Membranes. 3rd Ed. Ed: Yeagle. CRC Press 2011. 19-89.
Li et al., Microfluidic system for planar patch clamp electrode arrays. Nano Lett. Apr. 2006;6(4):815-9.
Luan et al., Base-by-base ratcheting of single stranded DNA through a solid-state nanopore. Phys Rev Lett. Jun. 11, 2010;104(23):238103. Epub Jun. 10, 2010.
Mach et al., Miniaturized planar lipid bilayer: increased stability, low electric noise and fast fluid perfusion. Anal Bioanal Chem. Feb. 2008;390(3):841-6. Epub Oct. 31, 2007.
Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.
Malmstadt et al., Automated formation of lipid-bilayer membranes in a microfluidic device. Nano Lett. Sep. 2006;6(9):1961-5.
Mangold et al., Reference electrodes based on conducting polymers. Fresenius J Anal Chem. Jun. 2000;367(4):340-2.
Mastrangeli et al., Challenges for Capillary Self-Assembly of Microsystems. IEEE Transactions. Jan. 2011;1(1):133-149.
Mastrangeli et al., Self-assembly from milli- to nanoscales: methods and applications. J Micro Microeng. 2009;19:083001.
Maurer et al., Reconstitution of ion channels in agarose-supported silicon orifices. Biosens Bioelectron. May 15, 2007;22(11):2577-84. Epub Nov. 13, 2006.
McAlduff et al., Freestanding lipid bilayers as substrates for electron cryomicroscopy of integral membrane proteins. J Microsc. Feb. 2002;205(Pt 2):113-7.
Montal et al., Formation of bimolecular membranes from lipid monolayers and a study of their electrical properties. Proc Natl Acad Sci U S A. Dec. 1972;69(12):3561-6.
Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.
Ogier et al., Suspended Planar Phospholipid Bilayers on Micromachined Supports, Langmuir, vol. 16:5696-5701 (2000).
Onoe et al., Three-Dimensional Micro-Self-Assembly Using Hydrophobic Interaction Controlled by Self-Assembled Monolayers. J Micro Systems. Aug. 2004;13(4):603-611.
Parthasarathy et al., Protein patterns at lipid bilayer junctions. Proc Natl Acad Sci U S A. Aug. 31, 2004;101(35):12798-803. Epub Aug. 20, 2004.
Peterman et al., Ion Channels and Lipid Bilayer Membranes Under High Potentials Using Microfabricated Apertures. Biomedical Microdevices, vol. 4(3):231-236 (2002).
Polk et al., Ag/AgCl microelectrodes with improved stability for microfluidics, Sensors and Actuators B., vol. 114:239-247 (2006).
Rauf et al., Studies on sildenafil citrate (Viagra) interaction with DNA using electrochemical DNA biosensor. Biosens Bioelectron. May 15, 2007;22(11):2471-7. Epub Nov. 7, 2006.
Romer et al., Impedance analysis and single-channel recordings on nano-black lipid membranes based on porous alumina. Biophys J. Feb. 2004;86(2):955-65.
Sackmann, Supported membranes: scientific and practical applications. Science. Jan. 5, 1996;271(5245):43-8.

(56) References Cited

OTHER PUBLICATIONS

Sandison et al., Air-exposure technique for the formation of artificial lipid bilayers in microsystems. Langmuir. Jul. 17, 2007;23(15):8277-84. Epub Jun. 22, 2007.
Sandison et al., Rapid fabrication of polymer microfluidic systems for the production of artificial lipid bilayers. J. Micromech. Microeng., vol. 15:S139-S144 (2005).
Sapra et al., Lipid-coated hydrogel shapes as components of electrical circuits and mechanical devices. Sci Rep. 2012;2:848. doi: 10.1038/srep00848. Epub Nov. 14, 2012.
Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.
Schindler et al., Branched bimolecular lipid membranes. Biophys J. Sep. 1976;16(9):1109-13.
Schmidt et al., A Chip-Based Biosensor for the Functional Analysis of Single Ion Channels. Angew Chem Int Ed Engl. Sep. 1, 2000;39(17):3137-3140.
Shim et al., Stochastic sensing on a modular chip containing a single-ion channel. Anal Chem. Mar. 15, 2007;79(6):2207-13. Epub Feb. 9, 2007. Author Manuscript, 13 pages.
Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008. Author Manuscript, 17 pages.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sun et al., Microfluidic static droplet arrays with tuneable gradients in material composition. Lab Chip. Dec. 7, 2011;11(23):3949-52. doi: 10.1039/c1lc20709a. Epub Oct. 12, 2011.
Suzuki et al., Highly reproducible method of planar lipid bilayer reconstitution in polymethyl methacrylate microfluidic chip. Langmuir. Feb. 14, 2006;22(4):1937-42.
Suzuki et al., Planar lipid bilayer reconstitution with a micro-fluidic system. Lab Chip. Oct. 2004;4(5):502-5. Epub Sep. 2, 2004.
Suzuki et al., Planar Lipid Membrane Array for Membrane Protein Chip. 17th IEEE International Conference on Micro Electro Mechanical Systems (MEMS), pp. 272-275 (2004).
Syms et al., Surface Tension-Powered Self-Assembly of Microstructures—The State of the Art. J Micro Systems. Aug. 2003;12(4):387-417.
Third Party Submission Under 37 CFR 1.290 for U.S. Appl. No. 14/302,287 dated May 19, 2016.
Thorsen et al., Dynamic pattern formation in a vesicle-generating microfluidic device. Phys Rev Lett. Apr. 30, 2001;86(18):4163-6.
Urisu et al., Formation of high-resistance supported lipid bilayer on the surface of a silicon substrate with microelectrodes. Nanomedicine. Dec. 2005;1(4):317-22.
Vidinha et al., Ion jelly: a tailor-made conducting material for smart electrochemical devices. Chem Commun (Camb). Nov. 30, 2008;(44):5842-4. doi: 10.1039/b811647d. Epub Oct. 3, 2008.
Vulto et al., Microfluidic channel fabrication in dry film resist for production and prototyping of hybrid chips. Lab Chip. Feb. 2005;5(2):158-62. Epub Dec. 3, 2004.
Wagterveld et al., Ultralow hysteresis superhydrophobic surfaces by excimer laser modification of SU-8. Langmuir. Dec. 19, 2006;22(26):10904-8.
Watanabe et al., Electrical recording of Nanopore membrane proteins in a microfluidic device. The Papers of Technical Meeting on Bio Micro Systems, IEE Japa. 2010; BMS-10(7-27):5-8.
Yusko et al., Controlling protein translocation through nanopores with bio-inspired fluid walls. Nat Nanotechnol. Apr. 2011; 6(4): 253-260. Epub Feb. 20, 2011. doi: 10.1038/nnano.2011.12. Author Manuscript, 22 pages.
Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.
Zagnoni et al., Controlled delivery of proteins into bilayer lipid membranes on chip. Lab Chip. Sep. 2007;7(9):1176-83. Epub Jun. 27, 2007. Author Manuscript, 14 pages.
Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.
Piper et al., Stable silicon-ionic liquid interface for next-generation lithium-ion batteries. Nat Commun. Feb. 25, 2015;6:6230. 10 pages. doi: 10.1038/ncomms7230.
Tomimatsu et al. Possible contamination of ionic liquids upon dissolution and absorption of rubber and resin components, Journal of Molecular Liquids. Mar. 15, 2019;278:78-85.

\* cited by examiner

NANOPORE SENSING DEVICE, COMPONENTS AND METHOD OF OPERATION

RELATED APPLICATIONS

This application is a continuation of U.S. patent application Ser. No. 16/816,221, filed Mar. 11, 2020, entitled "NANOPORE SENSING DEVICE, COMPONENTS AND METHOD OF OPERATION," which claims the benefit of priority under 35 U.S.C. § 119 (e) to U.S. Provisional Patent Application Ser. No. 62/817,211, filed Mar. 12, 2019, and entitled "NANOPORE SENSING DEVICE, COMPONENTS AND METHOD OF OPERATION." The entirety of the applications listed above is herein incorporated by reference.

FIELD

The described technology relates to a device for nanopore sensing, having a plurality (e.g., an array) of nanopore structures configurable as nanopore sensors, as well as methods for operating nanopore sensors and/or for fabricating an array of nanopore structures.

BACKGROUND

Nanopore sensors have been developed for sensing a wide range of species, including single molecules such as polymer molecules. An example of a nanopore sensor device is a MinION™, manufactured and sold by Oxford Nanopore Technologies Ltd. The nanopore-based sensing therein employs the measurement of ionic current flow through a biological nanopore located in a highly resistive amphiphilic membrane. The MinION™ has an array of nanopore sensors. As a molecule, such as a polymer analyte (e.g. DNA), is caused to translocate a nanopore, measurement of the fluctuations in ionic current may be used to determine the sequence of the DNA strand. Nanopore devices for detection of analytes other than polynucleotides such as proteins are described in WO2013/123379 published on 22 Aug. 2013.

An alternative to biological nanopore devices, such as MinION™, are solid state nanopore devices. FIG. 1 shows a portion of a single sensor device 2 with a solid-state nanopore 4 disclosed in WO2016/127007, published on 11 Aug. 2016, hereby incorporated by reference in its entirety, in which an analyte 6 passes through a body 8 from a cis reservoir 10, through the solid-state nanopore 4 and into a fluidic passage 12; a signal is read via a sensor 16 located close to the nanopore. Electrodes 18 are provided in the reservoirs 10, 14 for inducing the analyte through the nanopore.

SUMMARY

The performance of solid-state nanopore sensors is limited by the sensing components, manufacturing techniques and their tolerances, which can occur as a result of variation in the formation of the nanopore or the assembly of the sensor. These and other factors detriment the bandwidth, sensitivity and ability to control such nanopore sensors.

An aspect of the described embodiments is to overcome problems associated with implementing a nanopore sensor array having a plurality of nanopore sensors.

The present inventors sought to improve upon nanopore sensing devices by providing, in some aspects, the ability to control the movement of an analyte while also improving the measurement accuracy by mitigating factors that impede on the measurement, such as noise caused by parasitics and contaminated sensing components. Moreover, the improved devices allow the nanopore structures, and nanopore sensors implemented therefrom, to be formed in large arrays in an efficient manner without inhibiting the control or performance of the array.

In a first aspect, some embodiments include a device for nanopore sensing, said device having: a structure arranged to separate an analyte reservoir and an outlet chamber, the structure comprising an array of nanopore structures, each nanopore structure comprising a passage for fluid connection through the structure between the analyte reservoir and outlet chamber;
  drive electrodes connected respectively to the analyte reservoir and the outlet chamber for imposing an electrical potential difference across the passages;
  electrical transduction elements, each element connected to, or exposed to, the passage of a respective nanopore structure for measuring the fluidic electrical potential at that electrical transduction element in that nanopore structure; and
  control terminals, each terminal connected to a respective nanopore structure for applying a control signal to alter the electrical potential difference across that nanopore structure or to alter an electrical potential within the passage.

The structure can be a support structure. The nanopore structures can be disposed in and/or on the corresponding array of passages. Each nanopore structure can have an aperture forming part of the passage. Each nanopore structure in the array of nanopore structures has a respective passage. The control terminal can be connected to a respective passage in that structure for applying a control signal to alter the fluidic electrical potential distribution around a respective nanopore structure. When provided with a fluid, such that there is a fluid connection between the drive electrodes and the nanopore structure, then the control signal applied to that nanopore structure can alter the electrical potential difference across that nanopore structure with respect to the drive electrodes. The control terminal can be connected to the electrical transduction element. The control terminal can be switchably connected to the electrical transduction element.

The nanopore structures of the array can have a nanopore, be capable of supporting a nanopore or be capable of supporting a membrane having a nanopore.

In operation as a nanopore sensing device, the device comprises an array of nanopores.

When provided with a fluid, fluidic electrical potential can be measured at the electrical transduction element. When provided with a fluid, the fluidic electrical distribution around that nanopore structure can be altered.

In operation, fluid resides in the analyte reservoir, outlet chamber and passages of the device wherein the reservoir and chamber are fluidically connected. The fluid in the reservoir, chamber and passages of the nanopore structure can be different fluids.

A nanopore structure may comprise an aperture having a width of nanometer dimensions. It may be a through hole in a solid-state support, such as a solid state nanopore.

Alternatively, in an embodiment, the nanopore structure may be a structure that is capable of supporting a nanopore to provide a passage of nanometer dimensions. In this embodiment the nanopore structure may comprise an aperture of micrometre or nanopore dimensions. Exemplary nanopore structures that may be used to support a nanopore are disclosed in WO2014/064443, hereby incorporated by reference in its entirety. Examples of nanopores that may be supported by the nanopore structure are biological nanopores such as protein nanopores. The nanopore may be provided in a membrane such as an amphiphilic membrane. The membrane may be supported by the nanopore structure.

In some embodiments, when used for nanopore sensing, the device may comprise (e.g., comprises) an array of nanopores.

The analyte reservoir can function to receive an analyte for sensing by the nanopore array. The outlet chamber can function to receive an analyte that passes through the nanopore array.

The nanopores (where present) separate a cis side and a trans side of the device. The analyte reservoir may be considered as the cis side of the device and the analyte outlet chamber may be considered as being part of the trans side.

The device may be provided with or without fluid. The fluid in the reservoir, chamber and passages of the nanopore structure can be different fluids.

Some embodiments relate to a structure comprising an array of nanopore structures, each nanopore structure comprising a passage for fluid connection through the structure. Each nanopore structure has an electrical transduction element, each element connected to, or exposed to, the passage of a respective nanopore structure for measuring the fluidic electrical potential at that electrical transduction element in that nanopore structure. Each nanopore structure also has a control terminal, each terminal connected to a respective nanopore structure for applying a control signal to alter the fluidic electrical potential distribution within the passage or around a respective nanopore structure.

The structure can be a support structure. The nanopore structures can be disposed in and/or on the corresponding array of passages. Each nanopore structure can have an aperture forming part of the passage. Each nanopore structure in the array of nanopore structures has a respective passage. The control terminal can be connected to a respective passage in that structure for applying a control signal to alter the fluidic electrical potential distribution around a respective nanopore structure. Each aperture of the array can be associated with a respective electrical transduction element and a control terminal.

Each nanopore structure in the array of nanopore structures can be considered a pixel, each pixel comprising an aperture, an electrical transduction element and a control terminal. An array of pixels can be arranged as a rectilinear grid in a manner analogous to the arrangement of pixels on a television screen. The nanopores when present in the nanopore structure forms part of the passage, namely a section of the passage is of nanometer width. The nanopore may be a solid state nanopore, namely wherein an aperture of nanopore width is provided in a solid support. Alternatively, the nanopore may be a hybrid nanopore, wherein a biological nanopore is provided in an aperture of a solid support. The biological nanopore may be supported in an amphipathic membrane. The amphipathic membrane may be supported by pillars such as disclosed in WO2014/064443. The nanopore structure capable of supporting a nanopore may comprise an aperture of a width greater than nanopore dimensions, such as micrometre dimensions. The nanopore structure may comprise means by which to support an amphipathic membrane. The cis can be used to store an analyte, such as an analyte, for analysis. The analyte can be passed through a nanopore in a nanopore sensor of the array. After passing through the nanopore the analyte can either remain in the passage or pass out of the passage in to the outlet chamber. When the cis, trans and passages of the array of nanopore structures are provided with a fluid the drive electrodes can impose an electrical potential difference across the passage. The drive electrodes can provide a potential difference across the apertures to induce passage of a charged analyte through a nanopore of the array. The potential difference can be altered to change the speed or direction of translocation of the analyte.

Each electrical transduction element in the array functions as a sensor electrode. Changes in ion current flow through the nanopore cause fluctuations in electrical potential caused by changes in ion current flow, said electrical potential may be measured to determine the presence or a property of an analyte. The fluid in the device, which can be aqueous, may contain ions. Multiple analytes may be translocated The drive electrode serves to provide a common potential difference across the array of nanopores, wherein multiple analytes may be measured simultaneously in the array. Measurements are made at the electrical transduction elements in each nanopore structure.

In some embodiments, each nanopore structure may have an associated control terminal. This terminal can be an independent connection to a control signal generated externally from the structure. This allows the electrical potential to be applied independently of altering electrical potential differences across other nanopore structures in the array. The control signal can be generated within the nanopore structure in response to an external trigger or switch. Or, the control signal can be generated from a circuit internal to that nanopore structure. The control signal has the effect of changing the voltage level at each nanopore structure. The control signal can be applied via the electrical transduction element for modifying the voltage between the passage and the drive electrode(s). Additionally, or alternatively, the control signal can be applied via an electrical connection, such as a terminal or further control electrode, in the passage.

The device may have a single drive electrode provided in electrical connection with the analyte reservoir and a single drive electrode provided in electrical connection with the outlet chamber wherein the drive electrode serves to provide a common potential difference across the nanopore array.

Alternatively, the device may comprise a plurality of drive electrodes on the cis and/or the trans side of the device.

The application of a control signal to an individual nanopore structure can function to change the potential difference across the nanopore structure, i.e. between that nanopore structure and the drive electrodes. By way of example, the drive electrode in the cis can have a voltage level of −0.1 volts, while the drive electrode in the trans can have a voltage level of 0.2 volts such that the potential difference across the passages of the array is 0.3 volts. The application of a control signal to impose a voltage of −2 volts at the nanopore structure results in a potential difference between the nanopore structure and the cis and trans electrodes of −1.9 volts and −2.2 volts, respectively, or a potential difference between the nanopore structure and the cis and trans electrodes of −1.9 volts and −1.8 volts, respectively.

The electrical transduction element and the control terminal of each nanopore structure can be directly connected. In doing so, the electrical transduction element can function as both a sensor electrode and a control electrode. This can be implemented by providing an electrical transduction element with two terminals: one for connecting to sensing circuitry, the other for connecting to control circuitry. In practice, the sensing circuitry and the control circuitry can reside in the same circuit or component. Any of the circuits can be located off-structure and connected to the structure via, for example, a wire-bond.

The control terminals can be configured to apply a control signal to alter the electrical potential difference from the drive electrodes to each respective nanopore structure in response to a measurement of the fluidic electrical potential at the electrical transduction element of that nanopore structure by said electrical transduction element. The application of the control signal can be configured to alter the potential difference between at least one of the control terminals and at least one of the drive electrodes.

A control signal applied to the control terminal of a nanopore structure can alter the magnitude and/or the polarity of the potential difference between that nanopore structure and a drive electrode, which can change the rate at which an analyte passes though the passage of that nanopore structure or change the direction of movement of that analyte.

The control signal can be connectable to a plurality of the nanopore structures to simultaneously alter the potential difference between the connected control terminals and at least one of the drive electrodes.

The control signal can be applied for purposes other than to reject an analyte or control the speed and or direction of its translocation. For example, the control signal can be applied to induce insertion of a biological nanopore in a membrane supported by the nanopore structure. The electrical transduction elements can be connected to a measuring circuit to read signals received from the electrical transduction element. The nanopore structure can be provided with a switchable connection to a measurement circuit. Said switchable connection can disconnect the measurement circuit prior to the application of a control signal. In this way the control signal can be disconnected from measurement circuitry and inhibit the control signal influencing the performance of measurement circuitry.

In other words, the electrical transduction elements can be isolatable prior to the application of the control signal. Each individual electrical transduction element of each nanopore structure can be selectively isolated prior to application of the control signal.

The control signal can be applied for various purposes.

The control signal can be applied independently of measurements of the analyte. For example, the control signal can be applied to a membrane supported by the nanopore structure to induce insertion of a biological nanopore in the membrane.

The control signal can be applied to a nanopore structure in response to a measurement by the electrical transduction element.

By way of example, the control signal can be applied to for the purpose of unblocking a nanopore when the device determines that the passage through the nanopore is blocked, for example by analyte. The control signal can then be applied to unblock the passage.

The device is able to determine that the nanopore is blocked from the measurement of the change in electrical potential caused by the inhibition of current flow through the nanopore. In the absence of interaction of analyte with the nanopore, ion current flow through the nanopore due to the presence of an ionic salt in the aqueous sample may be referred to as the open pore current. When an analyte interacts with the nanopore, ion current flow through the pore is reduced and variation in the reduction in ion current may be measured as a fluctuation in electrical potential at the sensor electrode (e.g., sensor electrode 126) over time as an analyte such as DNA translocates the nanopore. A blockage of the nanopore, for example due to analyte becoming immobilised in the pore gives rise to a reduced ion current flow whose value changes very little over time. In a further example, the control signal can be applied to eject an analyte from the nanopore which is not of interest or which is no longer of interest. Measurements can be performed in real-time such that a decision to eject the analyte may be made before complete measurement of the analyte, for example a polynucleotide is made.

With regard to the prior mentioned devices for sequencing polynucleotides such as the MinION™ device, current flow though the nanopores is measured under the application of a potential difference between a respective array of electrodes provided on one side of each the nanopores and a common electrode provided on the other side of the electrodes in an analyte reservoir. Because each nanopore has an associated electrode, it is possible to individually control the potential difference across each nanopore of the array and eject an analyte. In the hereinafter described embodiments, there are various advantages associated with carrying out measurement of the local potential at each nanopore by means of the electrical transduction elements. The drive electrodes serve to provide a potential difference across the nanopore array and not to measure analyte. Consequently, individual control of the potential difference at a nanopore by the drive electrodes is not possible. However, it is possible to provide individual control over the potential difference across each nanopore by means control terminals.

The array of nanopore structures can have circuits, each circuit associated with a respective nanopore structure and connected to the electrical transduction element. Each circuit can be configured to modify and/or process the signals received from the electrical transduction element. The circuit can also apply a control signal to the electrical transduction element. The circuit can isolate the control signal applied to the electrical transduction element from other sensing and processing functions.

Each circuit can reside within the pixel of the nanopore structure. Each circuit can be addressable. Each nanopore structure can be addressable. The addressing function can allow an external processor to communicate with a nanopore structure to at least one of receive measurement information or control movement of an analyte in the passage. In this way, the measurement and control of sensing at each individual passage can be independently controlled. The circuits may be provided on or embedded within the support structure.

Each electronic circuit can be associated with a group of nanopore structures. By way of example an electronic circuit can be shared by a group of four nanopore structures. Sensing and control of the nanopore structures in the group can be multiplexed. In this way the circuit can be addressable, and multiplexing used to control individual nanopore structures.

Each circuit may be associated with a respective nanopore structure or a group of nanopore structures. Each circuit can be connected to the control terminal and/or the electrical transduction element, such that the circuit configured to alter at the respective nanopore structure an electrical potential imposed by the drive electrodes in response to a measurement at the electrical transduction element and/or from an external processor attached thereto.

The structure can have a nanopore layer incorporating a nanopore and/or incorporating a well for supporting a solid-state film or a membrane having a nanopore. When provided with a nanopore the nanopore structure can be operated as a nanopore sensor. The nanopore layer can be provided with nanopore after the nanopore structure has been made. Nanopores can be provided by a user after a device having nanopore structures has been provided to them. The nanopore layer can be replaced such that the device is recyclable. The nanopore structure can also include a base layer incorporating channels. The nanopore layer and the base layer can be sandwiched or laminated together such that the nanopores and/or wells are aligned to define the passage. At least one of the electrical transduction element, the circuit, or the control terminal are disposed on or between the outer surface of the structure. The individual nanopore structures may be comprised of a single structure or one or more sub-structures connected to each other. The single or sub-structures may be planar or sheet like.

Each nanopore structure can be defined by its passage. The passage can fluidly connect a cis and trans. The passage can be formed by formations in each nanopore structure which, by way of example, is formed by: a nanopore layer for supporting a nanopore, the layer having a through-hole; a base layer having a channel, which functions as a through-hole. The through-holes of the nanopore layer and the base layer are aligned to for form the passage.

The electrical transduction element defines a part of the passage. By way of example, the electrical transduction element can be sandwiched or laminated between the nanopore layer and the base layer. It can, however, be located elsewhere in the passage. It can be configured around the passage provided there is a fluid connection, and can be a direct fluid connection, between the electrical transduction element and a nanopore provided in the nanopore layer.

The electrical transduction element and/or the circuit can be implemented on a sense layer. The sense layer can be a sub-structure. The sense layer can be sandwiched or embedded between the nanopore layer and the base layer, said sense layer having a through-hole that aligns with the through-holes of the nanopore layer and the base layer. To be clear, the nanopore layer, sense layer and base layer can be sub-structures that are stacked to provide an array of nanopore structures.

A nanopore, when provided in the nanopore structure, forms part of the passage. The rejection of an analyte can be managed using a control signal, which functions to control the movement of an analyte in the nanopore, e.g. reject the analyte from the nanopore. The nanopore in a passage can become blocked. The blockage of a nanopore can be sensed and a control signal applied to the nanopore structure to clear the blockage.

The nanopore can be a solid-state nanopore, namely a hole of nanometer width, provided in a solid-state membrane. This membrane can be the nanopore layer, or be a membrane placed upon the nanopore layer. A solid-state nanopore can be positioned on the nanopore layer. The nanopore can alternatively be a biological nanopore located in a solid-state film or membrane. Further alternatively, the nanopore layer can be formed with a well across which a membrane, such an amphiphilic membrane or a lipid bilayer can be formed such that a nanopore can be inserted in the membrane. In each of these nanopore examples one nanopore can be provided for each nanopore structure in the array.

The present inventors also sought to improve the architecture of nanopore sensors, in particular where the improvements could optimise the sensitivity and performance. The inventors generally sought to achieve this by providing a structure having nanopore structures, wherein the nanopore structures located in the structure provide fluid communication from one side of the structure to the other via a passage provided in each nanopore structure. In this way the structure can separate a cis and a trans. Each of the nanopore structures has a sensor electrode. In order to minimise the attenuation of a signal derived from the sensor electrode and to avoid any detriment to that signal from noise each nanopore structure is provided with a circuit for processing signals from the sensor electrode prior to processed signal being communicated for further processing and/or analysis. The circuit can be embedded in the nanopore structure. The circuit can occupy the same footprint as the nanopore structure such that the nanopore structure can be considered as an active pixel. A nanopore structure having its own circuit can complement the improved control mechanism disclosed herein by having a control signal generated and applied locally, thus minimising the influence of the control signal upon other nanopore structures of the array.

Therefore, some embodiments relate to a device having nanopore structures for sensing an analyte, the nanopore structures arranged to separate an analyte reservoir and an outlet chamber, each nanopore structure providing a passage for fluid connection through the structure between the analyte reservoir and outlet chamber, wherein each nanopore structure comprises: an electrical transduction element; and an electronic circuit configured to detect, and optionally amplify, a signal from the electrical transduction element, wherein each of the structures are configured to store, transmit, process or communicate at least a portion of the signal to a connectable processor, or perform some combination thereof. In some embodiments, each of the structures are configured to at least one of store, transmit, process and communicate at least a portion of the signal to a connectable processor.

The nanopore structures may be comprised as part of an overall structure wherein the individual nanopore structures are joined to each other.

The structure can be configured to separate an analyte chamber for receiving an analyte and an outlet chamber for collecting the analyte. Drive electrodes can be connected respectively in the analyte reservoir and the outlet chamber for imposing an electrical potential difference across the passages in the nanopore structures. When provided with nanopores, the nanopore structure can function as a nanopore sensor and the device can be a nanopore sensing device.

Each of the nanopore structures in the array can further comprise a compensation circuit. The compensation circuit function can be incorporated with the other processing functions of the circuit in the nanopore structure. The compensation circuit can have a variable gain amplifier and/or a variable capacitor in a feedback loop of the compensation circuit.

As described in the first aspect, the structure can have a control terminal for applying a control signal to alter the electrical potential difference across the nanopore structure. The control signal can be switchably applied to the control terminal to adjust the configurable voltage level imposed upon the pore.

The nanopore structures incorporating the circuit, which can include a compensation circuit, can be packaged in a defined footprint or pixel space. The array of pixel-spaced nanopore structures can be arranged in a tessellated array.

By processing the signal from an electrical transduction element, at least in part, within the nanopore structure itself, the signal can be processed or managed locally. For example, the signal can be amplified locally such that there is minimal attenuation or noise influencing the signal before it is analysed elsewhere. The circuit can also store the signal, signal values or data derived from the signal. In this way, information derived from the nanopore structure can be communicated to a processor remote from the nanopore structure on demand. Each nanopore structure, or circuit in the nanopore structure, can be addressable. The circuit can be connected to an analogue to digital converter (ADC) located off the nanopore structure.

The inventors further sought to provide a structure that, in general, improved the manufacturability of an array of nanopore structures, while improving sensitivity and performance. Not only can the array of nanopore structures herein provided an improved nanopore structure but the array of nanopore structures can complement the integration of the control functions and local control.

Therefore, some embodiments relate to a device having an array of nanopore structures. The structures can be configured in a sheet, the sheet comprising: a nanopore layer having an array of nanopores and/or an array of wells for supporting a nanopore; and a base layer having an array of channels, said base layer sandwiched or laminated to the nanopore layer to form the sheet, wherein the nanopores and/or the wells are aligned with the channels, wherein each of the nanopore structures comprise a passage, each passage defined at least in part by: one of the nanopores and/or one of the wells of the nanopore layer, at one side of the passage; a channel of the base layer at the other side of the passage; and an electrical transduction element.

Inventive aspects can reside in the array of nanopore structures itself. When provided with a nanopore each nanopore structure of the array functions as a nanopore sensor. Each nanopore structure has a through-hole defined by a nanopore, if provided, or a well, a channel and an electrical transduction element.

The sheet can be a substantially planar array of nanopore structures. When the nanopore structures are provided with a nanopore they can function as nanopore sensors. The sheet can be configured in the device to separate a cis and a trans chamber. The cis and the trans chamber can accommodate a fluid. The passages can be filled with a fluid and provide a fluid connection between the cis and the trans.

Configuring the nanopore layer and the base layer as separate layers can improve the scalability of the sheets. The layers can facilitate assembly of the device, thus reducing the cost of manufacture. The layering of the sheet can bring together the components of the nanopore structure in an efficient manner. Moreover, by having the different components of the nanopore structure on different layers can enable the formation or configuration of those components to be optimised. It is often the case that the process used in the fabrication of one component is incompatible or detrimental to the fabrication of another component. Furthermore, the optimal material for forming one component can be different from the optimal material for forming other components. By way of example, the array of nanopores and/or an array of wells of the nanopore can be formed separately from the base layer. The nanopore layer and base layer can comprise different materials. The separate layers can enable the components of the nanopore structure to be optimally configured and/or located.

The provisions of layers can enable a layer to be replaceable. The nanopore layer can be removably attachable. In this way a nanopore layer can be replaced with replacement nanopore such that the device can be recycled should, for example, the nanopore layer become contaminated.

Each nanopore structure of the sheet is defined by the passage. The various components of the nanopore structure i.e. the nanopore or nanopore well, the electrical transduction element and the channel form the passage. The nanopore layer does not have to have a nanopore and can be provided with a nanopore. A nanopore can be configured over the well of the nanopore layer, and in so doing this additional nanopore over the well also forms an element of the passage.

The electrical transduction element in each passage can be disposed between the nanopore layer and at least a portion of the channel. The electrical transduction element can be configured with a connection for measuring electrical potential of the fluid at the location of the electrical transduction element when the structure is provided with a nanopore and a fluid is provided in the passage.

The electrical transduction element can develop a characteristic that is indicative of the fluidic electrical potential at the electrical transduction element in that passage, via fluid in the passage that connects the cis and trans. The electrical transduction element can be an electrical connection. It can be located in the cis or the trans reservoir, on a surface of the nanopore structure, at a position within the passage, or other location within the nanopore structure.

The electrical transduction element can be a device or region of a device and/or circuit, a wire, or combination of circuit elements, that senses the fluidic electrical potential at the electrical transduction element of the device. Additionally, or alternatively, the circuit can be provided as a transduction element to develop a signal indicative of local electrical potential.

As described, the device can have a first fluidic reservoir and a second fluidic reservoir separated, at least in part, by the sheet. The first fluidic reservoir can function as a cis and hold an analyte to be analysed by the nanopore structure when provided with a sensor. The passages of the nanopore structures of the array connect the first fluidic reservoir to the second fluidic reservoir. The interface between the first fluidic reservoir and the second fluidic reservoir can be the passage or, more specifically, the nanopore in a nanopore sensor i.e. a nanopore structure provided with a nanopore.

The device can have drive electrodes connected in the first and second reservoirs to impose an electrical potential difference across the array of passages between the first and second fluidic reservoirs.

The sheet can be substantially planar. The surfaces of the sheet, which is the structure incorporating the array of nanopore structures, can have a cis-surface on the nanopore layer for facing a first fluidic reservoir and defining a cis-plane, and a trans-surface of the base layer for facing a second fluidic reservoir and defining a trans-plane. The array of electrical transduction elements can be embedded, at least in part, within the sheet between the cis-plane and the trans-plane. The electrical transduction elements of the array can be sandwiched between the nanopore layer and the base layer.

Each nanopore structure of the array can have a well formed at a first end of the passage. A nanopore can be configured at the first end of each well. The electrical transduction element can be configured on the opposite side of the well to the nanopore. The well can be larger in size that the nanopore and increase the volume of fluid surrounding the nanopore. To be clear, the diameter of the well can be greater than the diameter of the nanopore. The nanopore can reside in a membrane that spans the well. The membrane can be a solid-state membrane, an amphiphilic membrane or a lipid bilayer. The nanopore defines a portion of the passage. Ingress and egress from the well are via the nanopore and a well outlet.

The well can be configured for supporting a fluid membrane such as a polymer membrane or lipid bilayer. The nanopore layer can be fabricated from a different material from the base layer. By using a different material for the nanopore layer a material can be selected to have a surface energy that optimises the formation of a membrane across the well for supporting a nanopore.

The electrical transduction element can be a sensor electrode. The sensor electrode can be directly connectable to the base or gate of a transistor device for measuring variations in electrical potential of the fluid at the location of the electrical transduction element when a fluid is provided in the passage. As described herein, a nanopore structure provided with a nanopore forming a portion of the passage functions as a nanopore sensor, and the sensing is performed by the electrical transduction element.

The electrical transduction elements of the nanopore structures of the array can be connected to an edge-connector or wire-bond. The connector can provide a connection to a measurement circuit off-sheet i.e. separate from the array of nanopore structures. The connector can be connected to a via that leads to a connection at the edge of the sheet, for subsequent connection to a measurement circuit off-sheet. The transistor device can be a field effect transistor.

The sheet has been described thus far having a nanopore layer and base layer. The electrical transduction element can be a layer within the sheet or can have elements sandwiched between layers. The sheet of the device can, however, further comprise a sense layer having an array of the electrical transduction elements, wherein said sense layer is sandwiched between the nanopore layer and the base layer. The electrical transduction element can be formed upon the sense layer. The electrical transduction element can have an exposed portion for connection to a fluid in the passage and an embedded portion embedded within the sheet. Additionally, or alternatively, the electrical transduction element can have a connection portion for connection to a measurement circuit separate from the sheet. By incorporating the electrical transduction element in or upon the sense layer this enables the formation of electrical transduction element to be separate from the manufacture of the other layers. The sense layer can be fabricated using a different material, process and/or techniques from the other layers.

The electrical transduction element can cover, at least in part, a wall of the passage. The electrical transduction element can cover, in cross-section, a portion of a wall of the channel. The electrical transduction element can form an annulus around the passage and/or the base of a well or cavity within the passage.

The electrical transduction elements can be formed on one surface of the sense layer. The sense layer can be sandwiched between the base layer and the nanopore layer with the electrical transduction elements aligned with the nanopore or wells of the nanopore layer and the channels of the base layer. When aligned, the face of the sense layer can have the electrical transduction elements exposed to the nanopore layer, such that the nanopore layer is formed or placed upon the surface having the electrical transduction elements; in this arrangement the electrical transduction element can be said to face the nanopore layer. Alternatively, when aligned, the face of the sense layer can have the electrical transduction elements exposed to the base layer, such that the electrical transduction element is formed or placed upon the surface of the base layer; in this arrangement the electrical transduction element can be said to face the base layer.

The electrical transduction element can form, at least in part, the surface of the sense layer around the passage and have an exposed portion arranged to face the outlet chamber.

The exposed portion can form part of a wall of a cavity formed in the sense layer between the well and the channel. The cavity enables a greater area of the sensor electrode to be exposed to fluid in the passage. This can improve the sensitivity of the sensor electrode.

The electrical transduction element can have an aperture forming a portion of the passage and exposed portion, wherein in cross-section, the ratio of the size of the exposed portion of the electrical transduction element to the size of the aperture is 1:1. The ratio can be about 5:1.

The electrical transduction element can have an aperture forming a portion of the passage and exposed portion, wherein in plan-view, the ratio of the size of the exposed portion of the electrical transduction element to the size of the aperture is 1:1. The electrical transduction element can have an aperture forming a portion of the passage and exposed portion, wherein the ratio is about 5:1. The aperture can be circular.

The electrical transduction element can have a large exposed area to increase the exposure to a fluid in the passage to increase the sensitivity of the element to fluctuations in voltage caused by an analyte passing over, or through, a nanopore in the passage.

The sense layer can incorporate an electronic circuit for each nanopore structures. The circuit can be connected to the electrical transduction element for modifying and/or processing the signals received therefrom. By incorporating an electronic circuit within each nanopore structure then signals from the electrical transduction elements can be processed locally to inhibit any attenuation of information in the signal derived therefrom and/or inhibit any detriment to that signal from noise. Each electrical circuit in the respective nanopore structure can process signals from the sensor electrode prior to said processed signal being communicated off-sheet for further processing and/or analysis. By incorporating the circuit in the sense layer, the circuit can be embedded in the nanopore structure. The circuit can occupy the same footprint as the nanopore structure such that the nanopore structure can be considered as an active pixel. A nanopore structure having its own circuit can complement the improved control mechanism disclosed herein by having a control signal generated and applied locally, thus minimising the influence of the control signal upon other nanopore structures of the array. The circuit within the sense layer of the nanopore circuit can be a compensation circuit.

The electronic circuit can be configured to detect changes in voltage caused by resistance changes at a nanopore in a respective passage when an analyte passes through the nanopore, or adjacent said nanopore. The circuit can detect a resistance change detected through the fluid in the sensor.

While the device has been described as suitable for sensing an analyte it should be appreciated that the analyte is one that can be measured using a nanopore. By way of example the analyte can be a, protein, polymer, polynucleotide or the like.

The electronic circuit can detect resistance changes at the nanopore when a polymer passes through the nanopore and converts it to a voltage signal and amplifies said voltage signal. The electronic circuit can filter the signal. The electronic circuit can sample and/or digitise signals obtained from an electrical transduction element.

Each nanopore structure can have a plurality of electrical transduction elements corresponding to each respective nanopore structure. Similarly, each nanopore structure can have a plurality of circuits corresponding to each respective nanopore structure and/or electrical transduction element provided in that nanopore structure. Each of the electrical transduction elements and/or circuits can be configured in an addressable array. Each nanopore structure can have two or more sensor electrodes. Two or more electrodes can be connected to a single circuit within the nanopore structure or each sensor electrode could be connected to its own circuit.

The array of nanopore structures can be connected to an architecture for enabling readout from each nanopore structure individually (which may be referred to as pixels) in a matrix array. Each nanopore structure can have a row number and column number.

Each electrical transduction element can have a dedicated electronic circuit, and each electrical transduction element and electronic circuit can be located in a footprint. The footprint can be a pixel such that the nanopore structures are tessellated in the array.

While each nanopore structure of the array has an electrical transduction element and, optionally a circuit and/or a control terminal, in light of the teaching herein it can be appreciated that each nanopore structure can have a plurality of electrical transduction elements and/or a plurality of circuits, each circuit providing one or more functions. By way of example, a nanopore structure can have an electrical transduction element for sensing, and a corresponding circuit to process signals from that element and have a second electrical transduction element adapted for applying a control signal to the passage in the nanopore structure, said second electrical transduction element having a circuit for controllably applying said control signal.

It follows that a plurality of electrical transduction elements can be arranged in a module having a plurality of respective nanopore structures. The module can have a common dedicated electronic circuit, and each of the electrical transduction elements and electronic circuit are located in a footprint occupied by the plurality of nanopore structures. The module can have, for example, four nanopore structures, each having a respective electrical transduction element, wherein each element is connected to a common circuit. The common circuit can be addressably connected to an external off-structure or off-sheet electronic circuit.

The plurality of nanopore structures can be arranged in a two-dimensional matrix. The plurality of nanopore structures can be arranged in a tessellated pattern.

The electrical transduction element can be connected to the base or gate of a transistor for sensing. The transistor can be a field effect transistor.

Each of the nanopore structures can have a control terminal for applying a control signal to alter the electrical potential difference across the respective nanopore structure. The control terminal can be switchably connectable to the electrical transduction element. The control terminal can be switchably connectable to a power supply to change the configurable voltage level imposed upon the pore. The electrical transduction element and connection for measuring electrical potential of the fluid can be switchably isolatable from the control signal. The electrical transduction element and control electrode can be physically separate. At least a portion of the electrical transduction element and at least a portion of the control electrode can extend in the same plane. At least a portion of the electrical transduction element and at least a portion of the control electrode form, at least in part, the base of a well. At least a portion of the electrical transduction element and at least a portion of control electrode can extend perpendicularly from one another. At least a portion of the control electrode can be configured, at least in part, in the channel. The surface area of the electrical transduction element exposed to the passage can be less than the surface area of the control electrode exposed to the passage.

The device herein can be configured with a conductive guard configured in at least one of the nanopore layer, base layer or sensing layer. The conductive guard can extend between at least one of the electrical transduction element, and signal conductors connected thereto, and parasitic conductive elements in the nanopore layer, base layer or sense layer to inhibit parasitic capacitance from influencing the measurements obtained from the connection. A buffered version of the input signal can be applied to the guard conductor. As a result, there is no voltage difference across the capacitance from the input signal conductor to the conductive substrate.

The conductive guard can include, at least in part, an insulated guard conductor having and an insulating layer. The conductive guard can be configured to extend, at least in part, between the base layer and the channel.

The inventors have further considered the operation and manufacturability of the devices disclosed herein.

Some embodiments relate to a method of operating a device as described for nanopore sensing, the method comprising: translocating analyte through an array of nanopores under a potential difference applied across the array, measuring a change in the fluidic electrical potential at each nanopore by means of respective electrical transduction elements of and responsive to the measurement, applying a control signal to a control terminal of an electrical transduction element to alter the electrical potential difference across the nanopore. Therefore, some embodiments relate to a method of operating a device for nanopore sensing, the method comprising: imposing an electrical potential difference across an array of nanopore sensors disposed in a structure separating an analyte reservoir and an outlet chamber, each nanopore sensor having a passage for providing a fluid connection between the analyte reservoir and the outlet chamber; providing an analyte for analysis by the nanopore sensors, each nanopore sensor having an electrical transduction element for measuring a change in the fluidic electrical potential at the electrical transduction element of that nanopore sensor when an analyte is induced through a nanopore of the nanopore sensor; and applying a control signal to a control terminal of an electrical transduction element of a nanopore sensor of the array to alter the electrical potential difference across that nanopore sensor. Fluidic electrical potential can be measured at the electrical transduction element. The fluidic electrical distribution across that nanopore structure can be altered when the device is provided with a fluid. In operation, a fluid resides in the reservoir, chamber and passages of the nanopore structure. The fluid in the reservoir, chamber and passages of the nanopore structure can be different fluids.

The electrical potential difference imposed across the array serves to induce an analyte through, or at least in to, the passage. An analyte to be analysed is provided in the analyte reservoir and induced to the outlet chamber, which is achieved by the drive electrodes. The situation can, however, be reversed in that an analyte can be provided in the outlet chamber or an analyte in the outlet can be induced by the drive electrode in to the analyte reservoir e.g. by changing the potential difference between the drive electrodes.

In each case, the electrical transduction elements of each nanopore structure, which are provided with nanopores to function as nanopore sensors, can measure a change in the fluidic electrical potential. The array of nanopore structures is dimensioned such that the electrical transduction element of one nanopore sensors is inhibited from detecting an analyte passing through a nanopore in a neighbouring nanopore structure.

A control signal can be applied to an element to alter the electrical potential difference across the nanopore sensor in which said element resides.

The control terminal connected to the electrical transduction element can be switchably connected to the control terminal of the electrical transduction element for applying the control signal thereto. Additionally, or alternatively, the device can be operated to isolate any sensing circuitry from the electrical transduction element to inhibit damage to said circuitry while the control signal is applied.

The method can include analysing characteristics of the change in the electrical potential locally at a nanopore sensor and applying the control signal to that nanopore sensor in response to predetermined characteristics. The method can apply a control signal to an electrical transduction element of a nanopore sensor to alter the potential difference imposed by the drive electrodes at that nanopore sensor. The change in potential difference can induce movement of an analyte or a free-moving nanopore, which can be charged.

The control signal can perform a plurality of operations including, but not limited to: inducing pore insertion in to a membrane formed across the passage; unblocking a nanopore; rejecting an analyte; altering the rate of translocation of an analyte through that nanopore.

In forming a device having nanopore structures for sensing an analyte, the method of forming comprises: forming nanopore structures in a structure and arranging said structure to separate an analyte reservoir and an outlet chamber of the device such that each nanopore structure provides a passage for fluid connection through the structure between the analyte reservoir and outlet chamber; and fabricating in each nanopore structure: an electrical transduction element; and an electronic circuit configured to measure a signal from the electrical transduction element, wherein each of the nanopore structures are configured to at least one of store, transmit, process and communicate at least a portion of the measured signal, or information derived therefrom, to a connectable processor.

Fabricating an electronic circuit in each nanopore structure can enable measurements to be made at the electrical transduction element at that nanopore structure when provided with a nanopore to function as a sensor.

While measurements taken from a sensor can be communicated directly to an off-structure circuit for analysis the ability to locally process or condition the signal or information therefrom can improve noise performance, data management or amplification. By way of example, a circuit located within the nanopore structure can amplify a signal received from the electrical transduction element and, by amplifying the signal locally the level of noise amplified is minimised. If, for example, a signal received from the electrical transduction element were to be communicated off-structure before amplification for analysis the exposure of said signal to noise would be increased and subsequently amplified thus reducing the signal to noise ratio.

The method can further include configuring an analyte reservoir for receiving an analyte and an outlet chamber for collecting the analyte and configuring the nanopore layer to separate the analyte reservoir and outlet chamber. The structure can separate the cis and the trans of the device.

The method can further include configuring drive electrodes connected respectively in the analyte reservoir and the outlet chamber for imposing an electrical potential difference across the passage of the nanopore structures. The imposed electrical potential difference can be common across the plurality of nanopore structures. Multiple drive electrodes can be provided to achieve a common potential difference across the array of nanopore structures.

The method can further comprise configuring the electronic circuits with a switchable connection for applying a signal to a respective control terminal of the electrical transduction element for altering the electrical potential imposed by the drive electrodes across each respective nanopore structure.

The method can further comprise forming a control electrode in the passage of each nanopore sensor, said control electrode selectably connectable to a signal for altering an electrical potential imposed by the drive electrodes across each respective nanopore structure.

In fabricating a device having nanopore structures for sensing an analyte, the method of fabrication comprises forming a device having an array of nanopore structures configured in a sheet, including arranging the sheet to separate an analyte reservoir and an outlet chamber of the device such that each nanopore structure provides a passage for fluid connection through the structure between the analyte reservoir and outlet chamber, the method comprising: forming a nanopore layer having an array of nanopores and/or an array of support structures, such as wells, for supporting a nanopore; forming an array of electrical transduction elements; forming a base layer having an array of channels, said base layer sandwiched or laminated to the nanopore layer to form the sheet such that the nanopores and/or the wells are aligned with the electrical transduction elements and channels; and providing a passage through each of the nanopore structures such that each passage is defined at least in part by: one of the nanopores and/or one of the wells of the nanopore layer, at one side of the passage; a channel of the base layer at the other side of the passage; and an electrical transduction element.

Aligning the nanopore layer, base layer and array of electrical transduction elements can include sandwiching the array of electrical transduction elements between the nanopore layer and the base layer. The step of sandwiching can include bonding or otherwise connecting the two layers.

The method can further comprise forming cavities adjacent at least a portion of each of the electrical transduction elements. These cavities can increase the area of the element exposed to a fluid in the passage.

The method can further comprise: forming the array of electrical transduction elements on a sense layer; and sandwiching the sense layer between the nanopore layer and the base layer.

The method can further comprise: forming the array of electrical transduction elements on a sense layer; fabricating an array of electronic circuits in the sense layer, said circuits connected to respective electrical transduction elements for modifying and/or processing the signals received therefrom; and sandwiching the sense layer between the nanopore layer and the base layer.

The method can further comprise arranging the electrical transduction element to have: (i) an exposed portion for connection to a fluid in the passage, and (ii) an embedded portion embedded within the structure, and/or (iii) a connection portion for connection to a measurement circuit separate from the structure.

The method can further comprise forming a conductive guard in at least one of the nanopore layer, base layer or sense layer, said conductive guard configured to extend between at least one of the electrical transduction elements and signal conductors connected thereto and parasitic conductive elements in at least one of the nanopore layer, base layer or sense layer to inhibit parasitic capacitance from influencing the measurements obtained from the connection.

The method can further comprise providing for each nanopore structure a buffer, said buffer connecting the output of the electrical transduction element of that nanopore structure to a conductive guard.

The method can further comprise providing amphiphilic membranes in each of the nanopore structures of the array and inserting a biological nanopore in said membranes.

The method can include removably attaching the structure and/or removing the nanopore layer and replacing it with another nanopore layer. In this manner the device can be recycled.

Some embodiments relate to a device having a plurality of nanopore structures configured in a sheet, the sheet comprising: a nanopore layer having a plurality of nanopores and/or a plurality of wells for supporting a plurality nanopores; and a base layer having a plurality of channels, said base layer laminated to the nanopore layer to form the sheet, wherein the plurality of nanopores and/or the plurality of wells are aligned with the plurality of channels, wherein two or more of the nanopore structures each comprise a passage defined at least in part by: one of the nanopores and/or one of the wells of the nanopore layer, at one side of the passage; a channel of the base layer at the other side of the passage; and an electrical transduction element.

Some embodiments relate to a method of operating a device for nanopore sensing, the method comprising: imposing an electrical potential difference across a plurality of nanopore sensors disposed in a structure separating an analyte reservoir and an outlet chamber, two or more of the nanopore sensors each having a passage for providing a fluid connection between the analyte reservoir and the outlet chamber; providing an analyte for analysis by the nanopore sensors, the two or more nanopore sensors each having an electrical transduction element for measuring a change in the electrical potential at the electrical transduction element of that nanopore sensor when an analyte is induced through a nanopore of that nanopore sensor; and applying a control signal to a control terminal of an electrical transduction element of one of the two or more nanopore sensors to alter the electrical potential difference across that nanopore sensor.

Some embodiments relate to a method of forming a device having nanopore structures for sensing an analyte, the method comprising: forming the nanopore structures in a structure and arranging said structure to separate an analyte reservoir and an outlet chamber of the device such that two or more nanopore structures each provide a passage for fluid connection through the structure between the analyte reservoir and outlet chamber; and fabricating in each of the two or more nanopore structures: an electrical transduction element; and an electronic circuit configured to receive a signal from the electrical transduction element, herein the electronic circuit is configured to at least amplify and/or store the signal, or information derived therefrom.

Some embodiments relate to a method of forming a device having an array of nanopore structures arranged in a sheet that is configured to separate an analyte reservoir and an outlet chamber of the device such that two or more nanopore structures each provide a passage for fluid connection through the sheet between the analyte reservoir and outlet chamber, the method comprising: forming a nanopore layer having an array of nanopores and/or an array of wells for supporting a nanopore; forming an array of electrical transduction elements; forming a base layer having an array of channels, said base layer laminated to the nanopore layer to form the sheet such that the array of nanopores and/or the array of wells are aligned with the array of electrical transduction elements and array of channels, wherein each passage of the two or more nanopore structures is defined at least in part by: one of the nanopores and/or one of the wells of the nanopore layer, at one side of the passage; a channel of the base layer at the other side of the passage; and an electrical transduction element.

Many aspects have been described herein, and elements of different aspects can, in light of the teaching herein, be combined. Many further aspects are, therefore, implicit in light of the teaching of the description and the figures, which often combine two or more of the aspects described herein. In general, the different aspects may be combined together in any combination.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
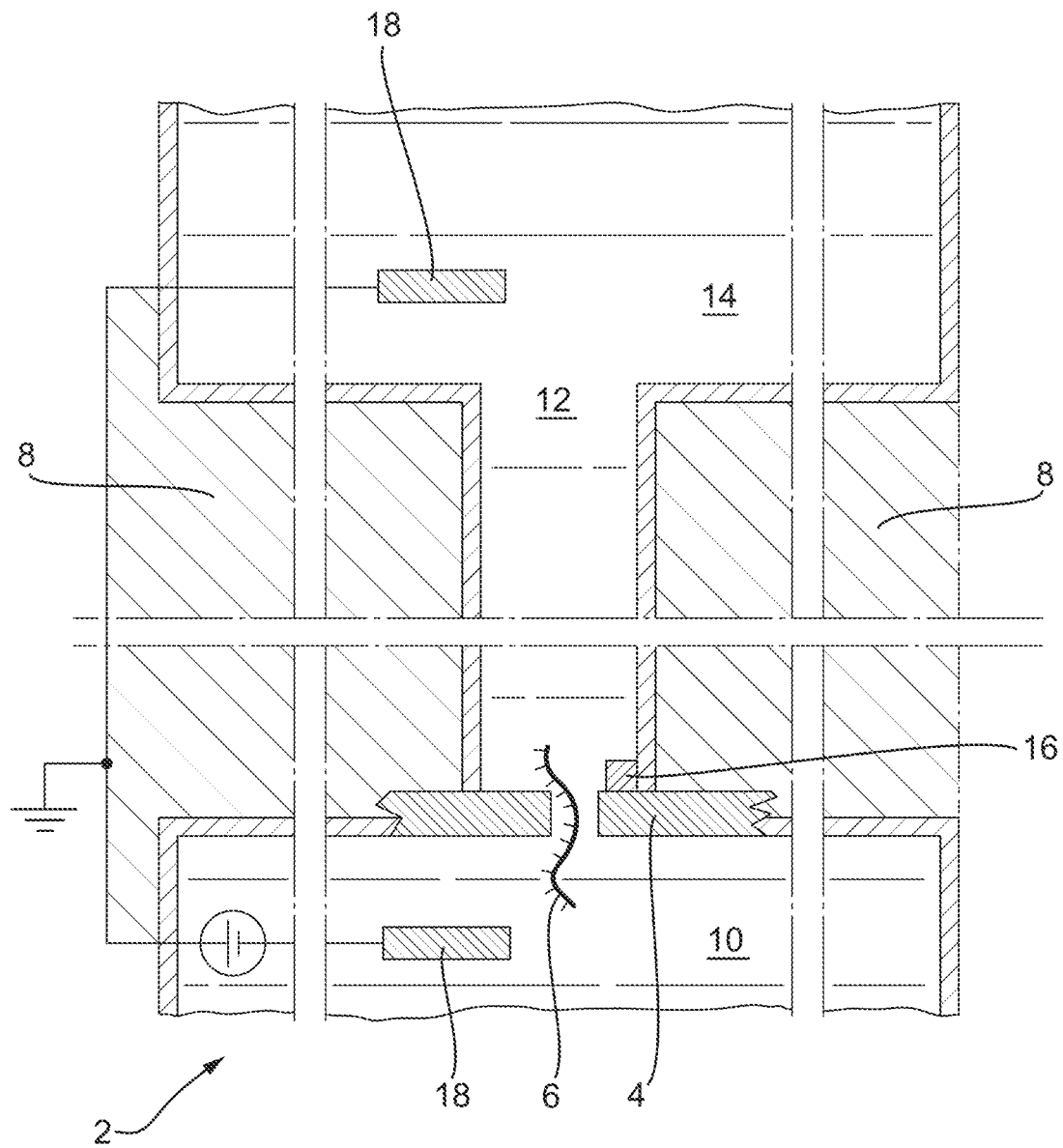
FIG. 1 depicts a cross sectional view of an example nanopore sensor of the related art.

In overview, devices for improved nanopore sensing are described. An example device can have a structure arranged to separate an analyte reservoir and an outlet chamber. The structure can have an array of nanopore structures, each nanopore structure comprising a passage for fluid connection through the structure between the analyte reservoir and outlet chamber. Control terminals can be included wherein each terminal connects to a respective nanopore structure for applying a control signal to alter the electrical potential difference across that nanopore structure. In further aspects, an improved nanopore structure for sensing an analyte can include an electronic circuit configured to detect a signal from an electrical transduction element, and wherein each of the structures may be configured to at least one of store, transmit, process and communicate at least a portion of the signal to a processor.

Some embodiments of a device for improved nanopore sensing have an array of nanopore structures configured in a sheet, the sheet comprising: a nanopore layer having an array of nanopores and/or an array of wells for supporting a nanopore; and a base layer having an array of channels, said base layer sandwiched to the nanopore layer to form the sheet, wherein the nanopores and/or the wells are aligned with the channels, wherein each of the nanopore structures comprise a passage, each passage defined at least in part by: one of the nanopores and/or one of the wells of the nanopore layer, at one side of the passage; a channel of the base layer at the other side of the passage; and an electrical transduction element.

Inventive aspects further relate to a method of operating a device for nanopore sensing, the method including: applying a control signal to a control terminal of an electrical transduction element of a nanopore sensor of the array to alter the electrical potential difference across that nanopore sensor.

Additional embodiments relate to methods of forming a device having nanopore structures for sensing an analyte. An example method may include fabricating in each nanopore structure: an electrical transduction element; and an electronic circuit configured to measure a signal from the electrical transduction element.

In further detail, FIGS. 2 to 4(a) are sectional views of a portion of a structure 100 having a nanopore structure 104 incorporated therein. In some implementations, the structure 100 has an array of nanopore structures 104, each nanopore structure adapted to support a nanopore 116. The nanopore structures of the device can function as nanopore sensors when configured with a nanopore. A nanopore sensor herein includes a nanopore structure having a nanopore. In some embodiments, a nanopore sensor herein is a nanopore structure having a nanopore.

FIGS. 4(b) to 4(f) illustrate that a plurality of the nanopore sensors 102 shown in FIGS. 2 to 4(a) can be arranged as part of an array of nanopore structures 104.

Figure 4A:
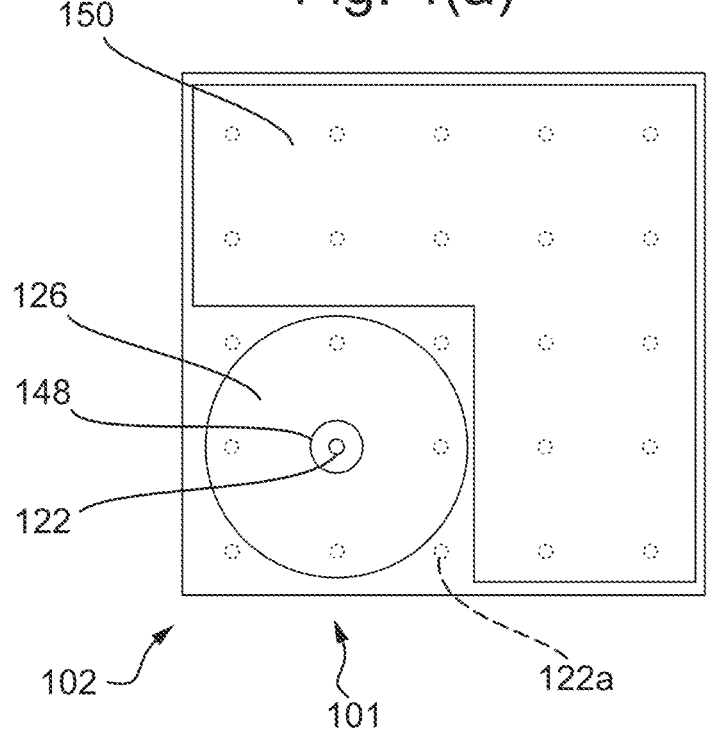
FIG. 4(a) is a schematic view of the layout of a nanopore sensor of FIG. 3(b) indicating the position of the well with respect to the electronic circuitry, according to some embodiments.
Figure 4B:
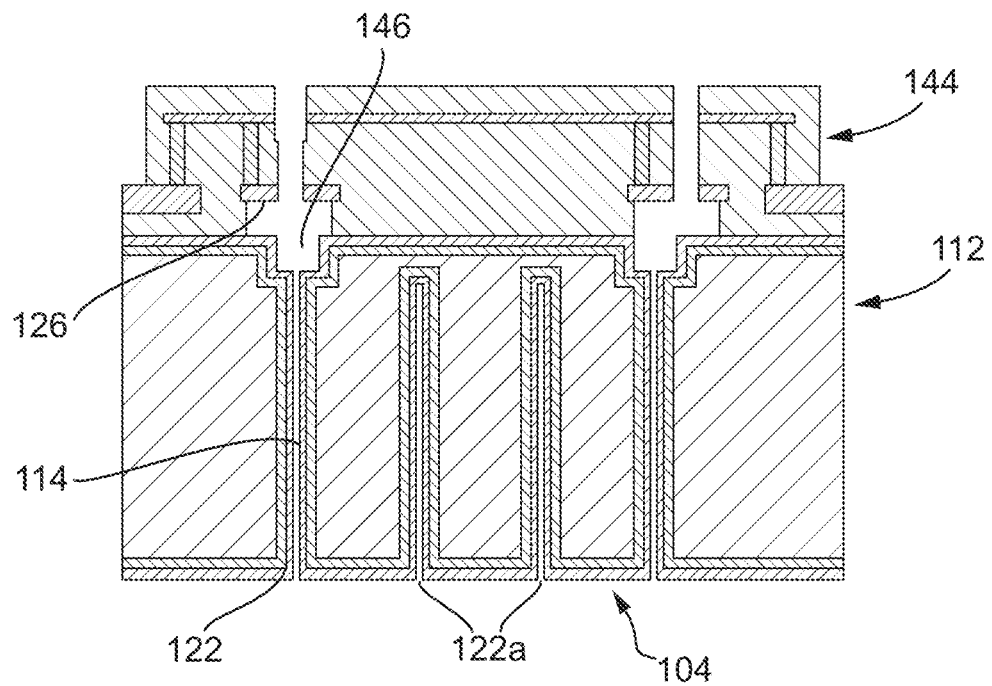
FIG. 4(b) shows two adjacent sensor electrodes before a pore is added.
Figure 4C:
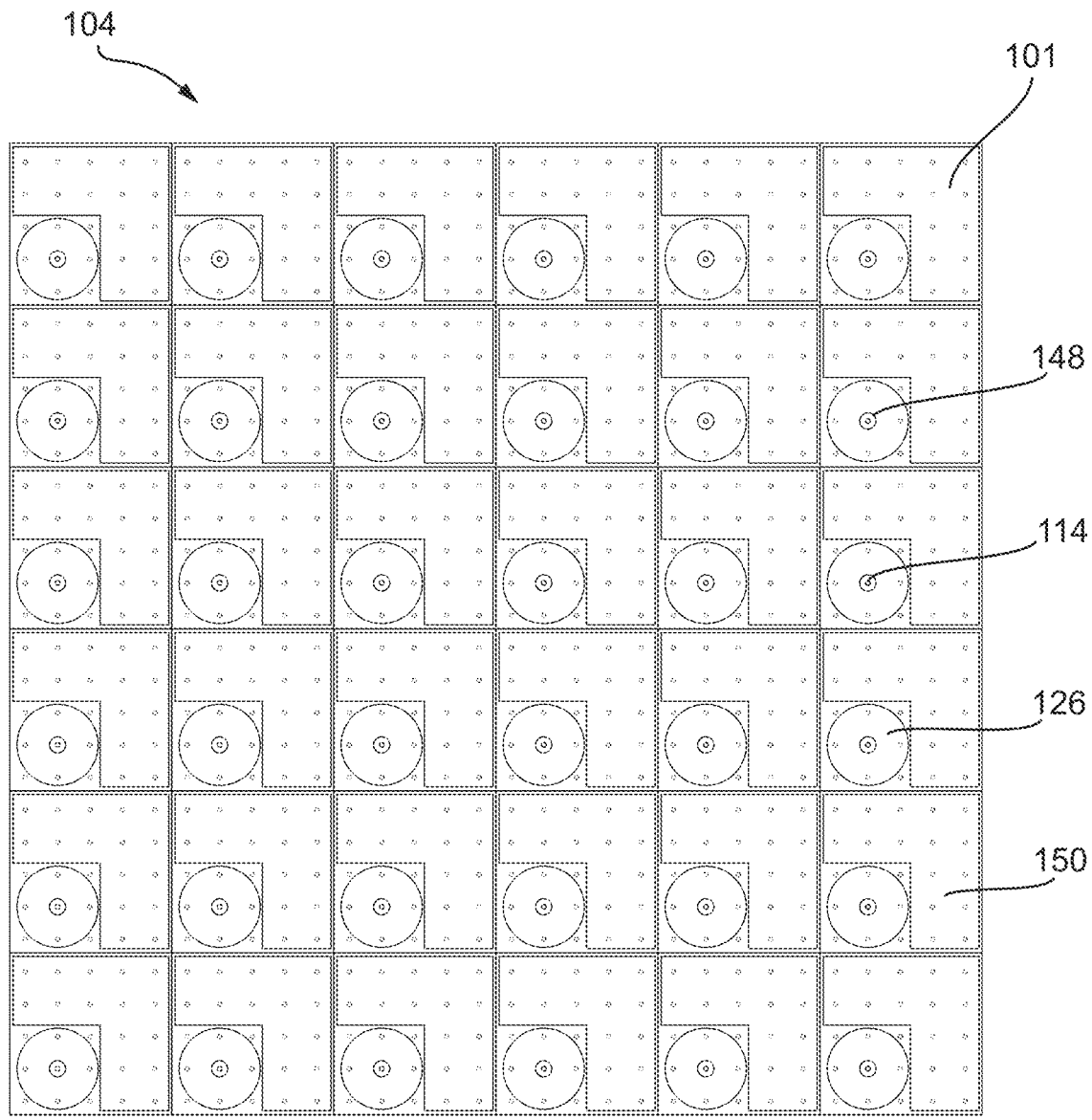
FIG. 4(c) and FIG. 4(d) are examples of portions of a structure having an array of the nanopore sensors of FIG. 4(a)
Figure 4D:
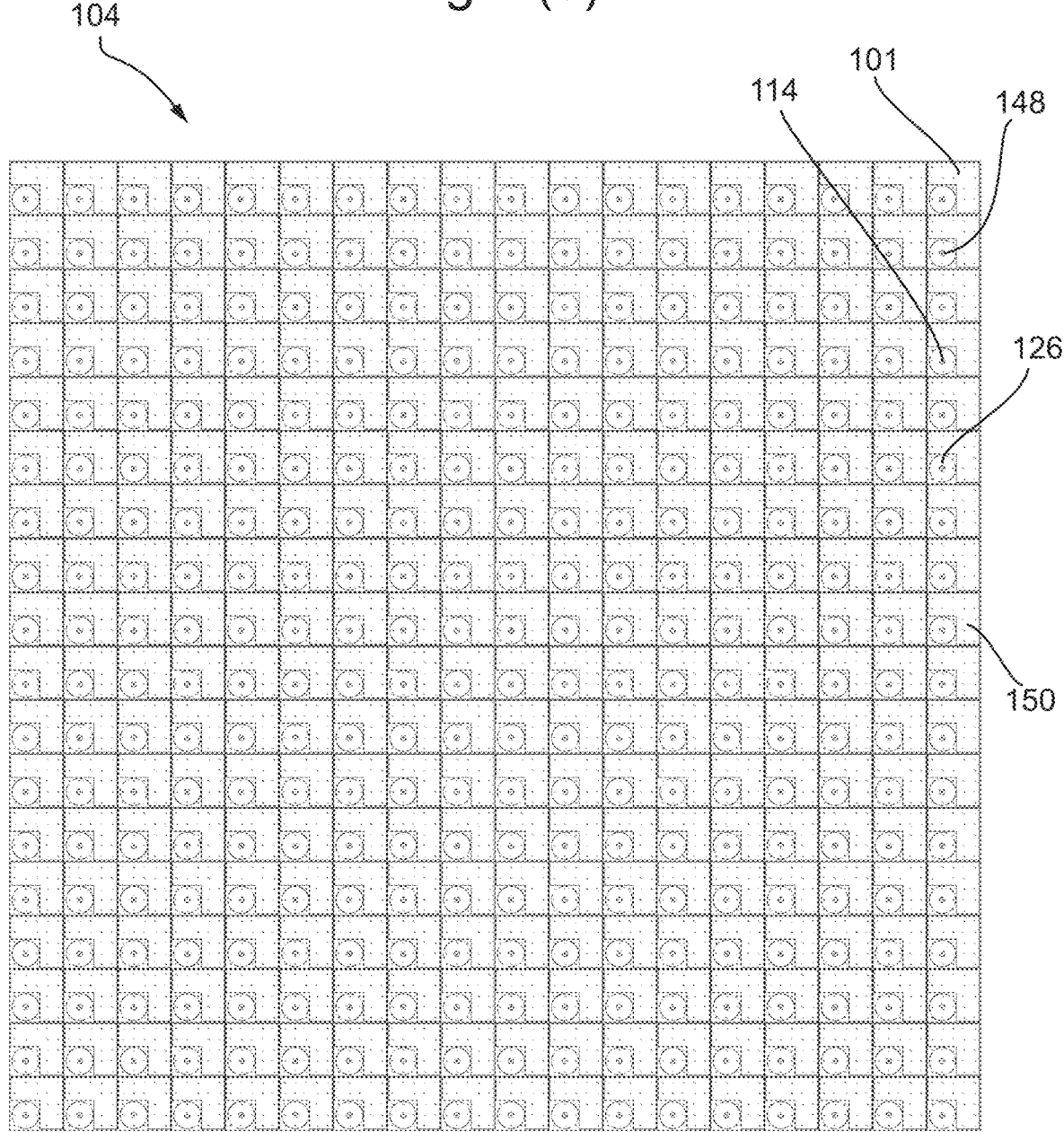
Figure 4E:
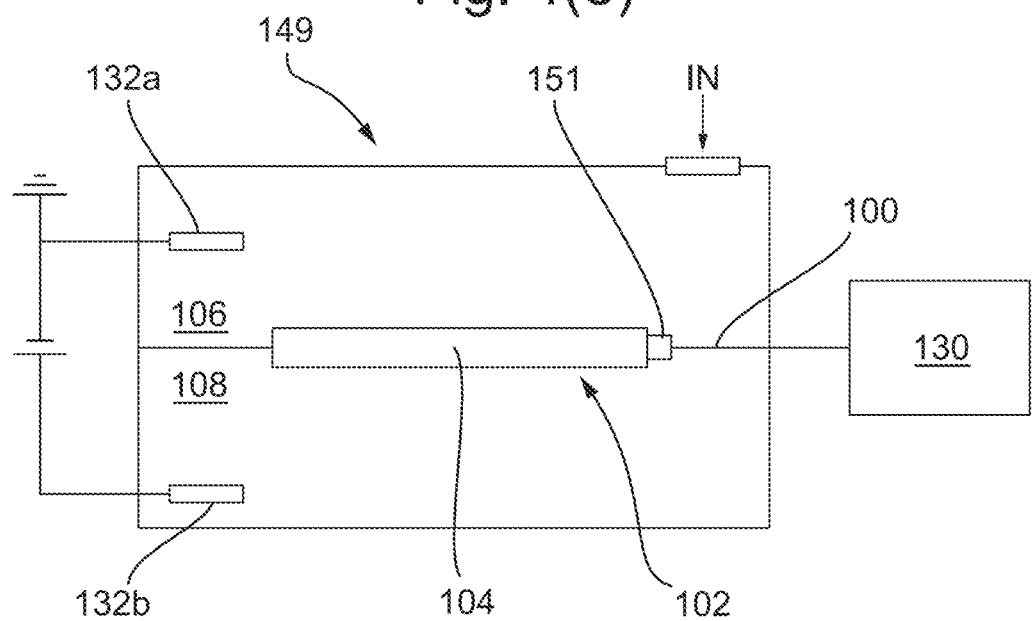
FIG. 4(e) is a schematic showing how a structure can be arranged to separate two chambers in a device, according to some embodiments.

The structure 100, which may take the form of a sheet, incorporates the array of nanopore sensors (n.b. only one nanopore sensor of the array is shown) and can be configured within a device or device for analysing an analyte, as shown in FIG. 4(e).

The structure 100 separates the analyte reservoir 106 for receiving an analyte and an outlet chamber 108. The structure 100 has a nanopore layer 110 configured upon a base layer 112, which together forms at least a portion of the structure having a plurality of nanopore sensors 102. Each nanopore sensor 102 in the array of nanopore structures 104 has a passage 114 configured to extend through the nanopore layer and base layer of the array for connecting the analyte chamber and outlet chamber.

The nanopore layer 110 of each nanopore sensor 102 may optionally be provided with a nanopore 116 in a membrane 118 supported by the nanopore layer. The nanopore layer 110 of each nanopore sensor 102 may optionally be provided with a nanopore 116 in a membrane 118 supported between the pillars of the nanopore layer. Alternatively, the nanopore can be a so-called solid state nanopore, namely a nanometer sized through-hole provided in a solid-state support layer. Further alternatively, the nanopore can be a so-called hybrid nanopore, namely a biological nanopore provided in an aperture of a solid-state membrane. Either way, the nanopore is provided in a membrane proximal the first end 120, or pore end, of the passage 114 (e.g. at the top of the sensor as shown).

The base layer 112 has a channel 122 proximal an opposite end 124, or channel end, of the passage 114 to the first end 120 (e.g. at the bottom of the sensor as shown). The passage 114 extends through the nanopore structure connecting one side to the other. The channel 122 forms part of the passage. The channel is structurally and geometrically configured to function as a fluidic resistor. This can be achieved by defining the aspect ratio of the channel. Additionally, or alternatively other techniques for implementing fluidic resistance in the channel can be used. The channel can be configured such that the resistance of the channel and the nanopore are substantially matched, when the passage is occupied by fluid, and relatively high relative to the resistance of fluid in the cis and trans reservoirs such that the resistance of the reservoirs does not appreciably influence the measurements. In other words, the channel is configured as a fluidic resistor to approximate the resistance of the nanopore means that the resistance of other circuit elements such as the of the fluid in the reservoirs has less significance and does not require compensation to account for it when measurements are taken.

The fluidic resistance of the channel 122 can be varied by varying its dimensions, in particular its aspect ratio and by varying the ionic concentrations of the fluids in the analyte reservoir 106 and the outlet chamber 108. For example, the channel 122 can be configured with a high aspect ratio to increase the resistance. Additionally, or alternatively, the fluid in the channel can have a lower ionic concentration compared to the fluid in the cis and trans to increase the channel's resistance. Maintaining a higher ionic concentration higher in the cis and the trans improves the signal to noise ratio.

In some embodiments, the aspect ratio can, for example, be between about 100:1 to about 2000:1, which is a ratio of channel length to channel diameter or largest transverse dimension. In some embodiments, the ionic concentration difference may be between about 1:1 to about 2000:1, for example around 1000:1, which is a ratio of ionic concentration in the cis and/or trans reservoirs to the ionic concentration in the channel.

The signal-to-noise ratio may be optimised by selecting the fluidic resistance of the channel 122 to be equal to the resistance of the nanopore 116. However, this is not essential and the fluidic resistance of the channel 122 may be varied from this value to take account of other factors, while still obtaining an acceptable signal-to-noise ratio. An acceptable signal-to-noise ratio may be achieved with the fluidic resistance of the channel 122 being significantly less than the resistance of the nanopore 116, for example with the fluidic resistance of the channel 122 being 10% or less of the resistance of the nanopore 116, for example 2% of the resistance of the nanopore 116 or less. In some embodiments, a lower limit on the fluidic resistance of the channel 122 may be set by the desired signal to noise ratio. In other embodiments, a lower limit on the fluidic resistance of the channel 122 may be set by the threshold for crosstalk between adjacent channels during flicking (as described below). That is, the fluidic resistance of the channel 122 is desirably significantly greater than the resistance from the end of the channel 122 to the electrical transduction element to prevent these resistances forming a voltage divider which applies a fraction of the applied voltage to adjacent channels 122.

Other factors that may be considered in the selection of the fluidic resistance of the channel 122 are as follows.

As the fluidic resistance of the channel 122 increases, the diffusion of ions decreases, causing increased depletion of ions near the pore, and thereby causing a decay of the signal over the timescale of a typical event over which a signal is obtained. In order to increase the limit on read length caused by this effect, the fluidic resistance of the channel 122 may be reduced. In many embodiments, this factor may place an upper limit on the fluidic resistance of the channel 122.

As the fluid channel 122 and the nanopore 116 act as a voltage divider, the voltage across the nanopore 116 is affected by the current flowing through it. As the fluidic resistance of the channel 122 increases, the variation in the voltage across the nanopore 116 increases, which can complicate signal processing. In order to limit this effect, the fluidic resistance of the channel 122 may be reduced.

Channels having lower fluidic resistances are easier to fabricate, and may open up alternative fabrication techniques that improve yield or reduce cost.

Reducing the fluidic resistance of the channel 122 may increase bandwidth or provide leeway for additional capacitance in the passage.

Taking into account these factors, the fluidic resistance of the channel 122 may be less than the resistance of the nanopore 116, typically at most 50%, or at most 25% of the resistance of the nanopore 116. In some embodiments, the optimal fluidic resistance of the channel 122 may be around 10% of the resistance of the nanopore 116.

When reducing the ratio of the fluidic resistance of the channel 122 to the resistance of the nanopore 116, the signal to noise ratio does not scale directly with that resistance ratio. For example, in some embodiments when the fluidic resistance of the channel 122 is around 10% of the resistance of the nanopore 116, then the signal to noise ratio is around 30% of its optimal value.

The channel can be formed in a wafer, and after a passage is formed therethrough an oxide layer can be used to reduce the diameter of the passage through the base layer, thus enabling the amount of oxidisation to adjust the aspect ratio.

A sensor electrode 126 is disposed between the nanopore 116 and at least a portion of the channel 122. The sensor electrode 126 forms an electrical transduction element in this example. More generally, the sensor electrode 126 could be adapted to be formed as an electrical transduction element of any of the various types disclosed in WO2016/127007. The sensor electrode 126 is exposed, at least in part, to the passage 114 in the nanopore sensor 102, and configured with a connection 128 for measuring electrical potential of the fluid at the location of the sensor electrode 126 when a fluid is provided in the passage. The connection 128 may attach to a control terminal 129. Together with the nanopore layer and base layer, the sensor electrode defines the walls of the passage 114. The connection 128 can be a wire-bond to a separate electronic circuit 130, said circuit configured to apply control signals (e.g., bias voltages) and/or analyse signals obtained from the sensor electrode 126.

The analyte chamber or cis 106 can function as a first fluidic reservoir, while the outlet chamber or trans 108 can function as a second fluidic reservoir. The structure 100 can separate, at least in part, the cis and the trans and the passage 114 of a sensor 102 connects the first fluidic reservoir to the second fluidic reservoir.

In use, the passage 114 of each nanopore sensor 102 is occupied by a fluid. Further, drive electrodes 132 in the cis and trans comprise at least one respective cis electrode 132a and at least one respective trans electrode 132b configured to impose an electrical potential difference across the fluidic passages 114 of the nanopore structures in the array of nanopore structures 104 between the first and second fluidic reservoirs.

The structure 100 can be substantially planar. The array of nanopore structures 104 can be substantially planar. Non-planar configurations are envisaged by the inventors but not described herein. The sensors 102 in the array have a cis-surface 134 of the nanopore layer 110 arranged facing the first fluidic reservoir 106 and defining a cis-plane 136, and a trans-surface 138 of the base layer 112 for facing a second fluidic reservoir 108 and defining a trans-plane 140. This cis-plane 136 and trans-plane 140 are indicated by the hashed line in FIGS. 2, 3(*b*) and 7(*b*). The sensor electrode 126 is embedded within the structure between the cis-plane and the trans-plane. The nanopore 116 can lie substantially on the cis-plane 136 at the first end 120 of the passage while the opposite end 124 of the passage can lie substantially on the trans-plane 140.

Figure 2:
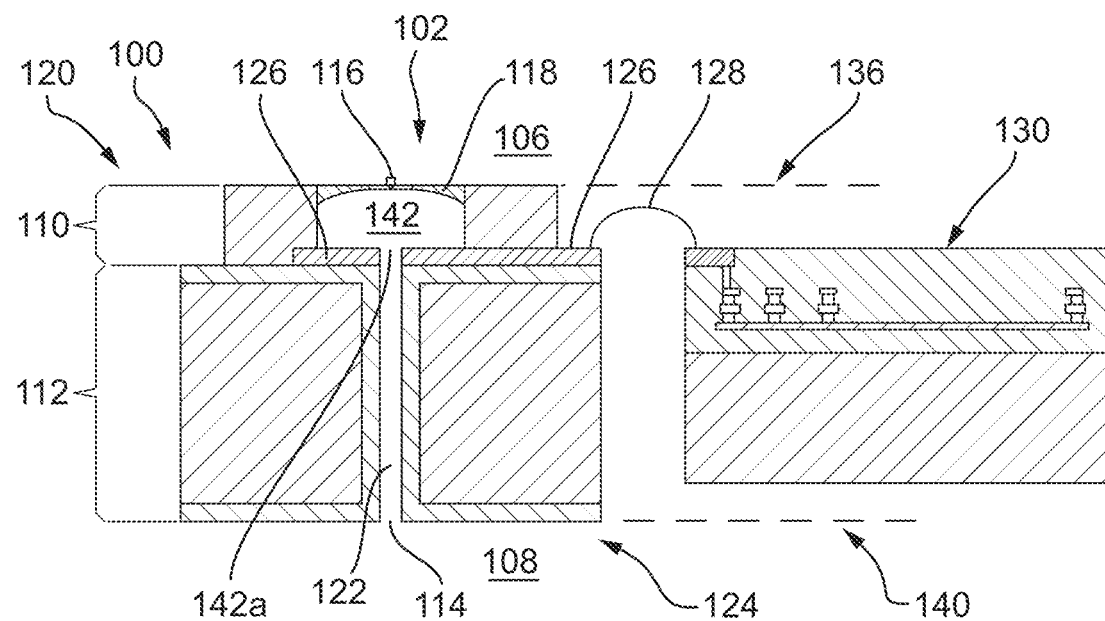
FIG. 2 is a cross-section of a single sensor electrode and corresponding biological nanopore within a nanopore array configured in a structure, and connected via a wire to a measurement circuit, according to some embodiments.

As shown in the assembly of FIG. 2, the sensor electrode 126 can, at least in part, be embedded between in the structure 100 between the nanopore layer 110 and the base layer 112. In other words, the sensor electrode 126 is sandwiched or laminated between the nanopore layer and the base layer.

The nanopore layer 110 has a well 142 formed at the first end of the passage. In the example of FIG. 2 the nanopore 116 is configured at the first end of the passage 114, on one side of the well, substantially on the cis-plane 136. The sensor electrode 126 can be configured (e.g., is configured) on the opposite side of the well to the nanopore, as shown. The well 142 is shown as a cup-shaped recess with a membrane, shown in cross-section, across its rim. The well is configured to receive an analyte that has passed through a nanopore. Note that the well 142 is fluidly connected to the channel 122 via a well aperture 142*a*, which can be described as a well outlet. The aperture 142*a* functions to enable the analyte chamber to be fluidly connected to the outlet chamber. The aperture 142*a* does not function as a nanopore. In some implementations, the aperture 142*a* is configured to enable an analyte to pass therethrough uninhibited i.e. without influencing movement of the analyte from the cis to the trans.

Although the aperture provides a fluid connection between the cis 106 and trans 108 an analyte that has passed through the nanopore 116 can remain in the well 142. The well 142 and channel 122 can be considered part of the outlet chamber 108. In the example shown in FIG. 2, the aperture is centrally located at the base of the well within the sensor electrode 126.

The well 142, and more generally the nanopore layer 110, is configured for supporting a fluid membrane 118 such as a polymer membrane or lipid bilayer. The nanopore layer 110 can be fabricated separately from the base layer 112. The nanopore layer can be formed from a different material from the base layer, and may be formed from a material other than a polymer or lipid bilayer. The nanopore layer can be formed from at least one of: a photolithographically prepared material; a moulded polymer; or a laser etched plastic.

According to some embodiments, the sensor electrode 126 is directly connectable to the base or gate of a transistor device for measuring electrical potential of the fluid at the location of the sensor electrode 126 when a fluid is provided in the passage. In some cases, the sensor electrode 126 can be connected to an edge-connector or wire-bond, optionally by a conductive via and/or interconnect, to a measurement circuit 130 off-structure. The transistor device can be a field effect transistor and the configuration of the transistor and its optional integration in to the structure is described in an example below. In some embodiments, the transistor device (not shown) can be located in the electronic circuit 130.

The nanopore sensor 102 shown in FIG. 2 is an example in which the sensor electrode can be formed upon the base layer 112. While the sensor electrode 126 of FIG. 2 can be formed on the base layer 126 directly it can, alternatively, be formed separately upon a sense layer 144, as depicted in FIG. 3(*a*) and FIG. 3(*b*). After forming the sensor electrode 126 on a sense layer, the sense layer may then be sandwiched (e.g., is sandwiched) between the nanopore layer 110 and base layer 112, resulting in the structure shown in FIG. 3(*a*) in some implementations.

The sense layer 144 can be fabricated in a similar manner to the base layer 112, wherein a wafer has passages formed therethrough, substantially perpendicular to the surfaces of the wafer. Alternatively, the wafer can be post-processed to open up the passage. The passages and/or channels 122 can be formed using techniques such as photolithography or deep reactive-ion etching (DRIE) or combinations thereof. The wafer can be enclosed by an oxide layer. The wafer can be a CMOS wafer. The sensor electrode 126 can be formed on the sense layer around the passages on one side of the sense layer, according to some embodiments. The passages through the sense layer 144, and the sensor electrode 126 formed around these passages, are arranged to have a pitch or layout that results in alignment with channels 122 on the base layer 112. When secured together, the passages of the sense layer 144 are aligned with the channels 122 of the base layer. In some cases, the nanopore layer 110 may be a polymer that is moulded or lithographically etched. The base layer 112 may comprise a semiconductor material, such as silicon. The sense layer 144 may comprise semiconductor materials and may be part of a CMOS wafer.

By way of example, the nanopore layer 110 may be made of polymer, which can be moulded or lithographically etched; the base layer 112 may be formed of a silicon wafer; and/or the sensor layer 144 may be a CMOS wafer.

The sense layer 144 can be aligned and bonded to the base layer 112 in one of two orientations. In one orientation (not shown) the sensor electrode remains fully exposed after bonding—that is to say that the sensor electrode: is not sandwiched between the sense layer; is distal from the base layer after the sense layer is secured to the base layer; and is subsequently sandwiched between the sense layer and the nanopore layer. In the other orientation, as shown in FIG. 3(*a*), the sensor electrode 126 is formed on top of a sense layer which is then inverted before bonding to the base layer such that the sensor electrode faces down, as viewed, and is sandwiched between the sense layer 144 and the base layer 112. Prior to bonding in this configuration, a section of the oxide layer on the base layer around the channel can be etched away or otherwise removed to create a cavity 146 such that there is an increased area of the sensor electrode exposed to the passage 114 after bonding. The area of exposed electrode can be maximised to increase contact with a fluid in the passage.

The wells 142 of the nanopore layer 110 are aligned with the passages and sensor electrodes 126 are bonded to the sense layer with the sensor electrodes 126 sandwiched therebetween. Looking at FIG. 3(*b*), and noting that the sensing layer 144 is fabricated from the bottom upwards, the last stage is the application of the sensor electrode 126 on top. When assembled, the sensor layer 144 is flipped over such that the sensor electrode 126 that was on top is now facing downwards, as shown in FIG. 3(*b*). The space 146 etched out of the base layer 112 oxide layer (the grey part) means that the sensor electrode is sufficiently exposed.

In some embodiments, the sensor electrode 126 remains exposed, at least in part, to the passage and configured with a connection for measuring electrical potential of the fluid at the location of the sensor electrode near the nanopore or at the nanopore when a fluid is provided in the passage. Arrangements of the sensor electrode 126—which minimise its surface area openly facing one of the analyte or outlet chambers (e.g. the arrangements of FIG. 2 or FIG. 3(*a*))—function to limit exposure to the analyte chamber 106 or outlet chamber 108 to inhibit contamination of the surface of the sensor electrode 126. One such example is shown in FIG. 3(*a*) that shows the sensor electrode substantially partially enclosed in the passage. Before population with a fluid, or during the formation of an amphiphilic membrane for supporting a biological nanopore, the surface of the sense electrode 126 can be exposed to fluids that could contaminate the surface of the electrode, thus if there is a contamination risk then it can be mitigated.

In one configuration, at least a portion of the sensor electrode 126 can be arranged to face away from the well 142 toward the channel 120, as shown in FIG. 3(*a*). An exposed portion of the sensor electrode provides a connection to a fluid in the passage 114 for sensing fluctuations in the fluidic electrical potential at the sensor electrode when an analyte passes through the pore. The sensor electrode 126 also can have (e.g., has) an embedded portion embedded within the structure. The sensor electrode 126 can also have a connection portion 128, such as a wire-bond, for connection to an electronic circuit 130, such as a measurement circuit or control circuit, which can be separate from the structure as shown in FIG. 3(*a*).

In each of the examples, the sensor electrode 126 can be configured in various configurations for exposure to a fluid within the passage and can, at least one of: cover, at least in part, a wall of the passage; cover, in cross-section, a portion of a wall of the passage; form an annulus around the passage; form, at least in part, the surface of the base layer or the sense layer around the passage and have an exposed portion arranged to face the analyte chamber; form, at least in part, the surface of the sense layer around the passage and have an exposed portion arranged to face the outlet chamber. In particular, a cavity 146 can be formed in the passage to create a region that enables the area of sensor electrode exposure to be increased and come in to contact with an increased amount of fluid. The cavity 146 is formed by recesses formed in the base layer 112 and/or sense layer 144 before the base and sense layer are aligned and connected.

While the sensor electrode 126 can have a minimal degree of exposure to the fluid in a well, such as in the form of a nanowire, the inventors have proposed the examples herein to optimise performance of the nanopore sensor 102 and improve manufacturability.

As shown in FIGS. 2 and 3(*a*) the sensor electrode 126 is substantially planar and shaped to accommodate the passage 114. In other words, the sensor electrode 126 is configured to enable uninhibited fluid communication between the cis 106 and trans 108, which can be achieved by either (i) shaping the sensor electrode to extend around the passage 114 or well aperture 142*a*, and/or (ii) forming a sensor aperture 148 in the sensor electrode.

The footprint of the exposed portion of the sensor electrode 126 can be any shape. The well 142 of FIG. 2 and the cavity 146 of FIG. 3(*a*) can be cylindrical such that the floor of the well is circular, or a planar surface of the cavity is curved. These configurations result in the exposed portion of the sensor electrode being circular or disc-shaped. In the examples shown a sensor aperture 142*a*, 148 is provided such that the footprint of the exposed portion is shaped like an annulus. The exposed area of the sensor electrode can be maximised, which can mean covering at least one face or surface of the well 142 and/or cavity 146.

The sensor electrode 126 and the sensor aperture 148 are shown as circular but could have other shapes. In some embodiments having circular shapes, the ratio of the radius of the exposed portion of the sensor electrode 126 to the radius of the sensor aperture 148 can be in a range from about 2:1 to about 100:1 (e.g., the ratio can be about 2:1) or in a range from about 10:1 to about 100:1. In the case of non-circular shapes, the ratio of the square roots of the areas may have the same values.

Alternatively, the area of exposed portion of the sensor electrode 126 can be expressed in relation to the ratio between the area or footprint as viewed of the sensor aperture 148 can be about 1:1, or about 10:1 or about 100:1

By way of example, the sensor electrode 126 may have a diameter (or maximum dimension) in a range from 10 μm to 50 μm and the sensor aperture 148 may have a diameter (or maximum dimension) in a range upwards from 0.5 μm. The sensor aperture 148 does not function as a sensor so its size does not have an upper limit within the bound that it is desirable to minimise the restriction of the remaining area of the sensor electrode 126.

The sensor electrode 126 may be formed from a suitable conductive material. In some cases, the sensor electrode 126 may be formed using platinum. In some implementations, the sensor electrode 126 may be formed using gold.

While FIGS. 2 and 3(*a*) have a sensor electrode 126 having a connection 128 to a separate electronic circuit 130, FIG. 3(*b*) illustrates that the structure 100 and array of nanopore structures 104 can accommodate an integrated circuit 150. The integrated circuit can incorporate one or more of the functions of the electronic circuit 130. In other words, various functions, such as sensing, amplifying, controlling, filtering, reading out, etc. which can be implemented on the separate electronic circuit 130 can be implemented, alternatively, on the integrated circuit 150. The integrated circuit can be formed on a separate layer or wafer and subsequently connected to the sense layer having the sensor electrode thereon. The inventors envisage, however, that the integrated circuit 150 is fabricated within the sense layer together with the sensor electrode. An integrated circuit can be provided for each nanopore sensor 102.

According to some embodiments, after fabrication of the sense layer 144 having the integrated circuit 150 and sensor electrode 126 formed and exposed on one side, the sensing structure is flipped and bonded to the base layer in the same way as it was in relation to FIG. 3(*a*). Connections 128 (not shown in FIG. 3(*b*)) connect the integrated circuit with a connector for sending signals or data produced by the integrated circuit off the structure. The connections can be connected to a connector 151 as shown in FIG. 4(*e*), although other configurations are implementable. With the sense layer connected to the base layer the nanopore layer 110 can be formed thereon such that the sense layer is sandwiched between the nanopore layer and the base layer. As before with FIG. 3(*a*), when bonded together, the passages of the sense layer 144 align with the channels of the base layer and the well of the nanopore layer form a portion of the passage 114.

In use, the electronic circuit and/or integrated circuit 150 is configured to detect resistance changes at the nanopore when an analyte, such as a polymer, passes through the nanopore, said resistance change detected through the fluid in the sensor (e.g., a measure of resistance being detected as a voltage over the effective voltage divider, as described above). For example, changes in resistance at the nanopore can cause changes in an applied voltage, which is detected by the circuit 150. In an array of nanopore structures 104 the integrated circuit of each sensor 102 can be communicably addressable. In light of parasitics, noise from communications, and background noise, the detected voltage changes or the detected resistance can be difficult to read directly using an off-board processor. To provide a processor with a better signal, i.e. a cleaner reduced noise signal, the integrated circuit can be configured to locally transform or modify or otherwise process signals derived from the detection of a polynucleotide or other analyte passing through the nanopore 116. In some embodiments, the integrated circuit can be configured to at least one of: amplify signals, such as amplifying a voltage level of the signal; filter the signal, for example to remove noise; sample the signal; digitise the signal using an analogue to digital converter (ADC) implemented in the electronic circuit.

According to some embodiments, at least one integrated circuit 150 can be formed or packaged within at least one nanopore sensor 102 footprint within the array of nanopore structures 104 of the structure 100.

By way of example, each nanopore sensor 102 of the array of nanopore structures 104 can be contained or packaged within a nanopore sensor footprint 101, which can be regarded as a footprint of a nanopore sensor 102, as viewed in FIG. 4(*a*), which can be considered to represent a schematic plan view of a nanopore sensor 102 depicted in FIG. 3(*b*). As illustrated in FIG. 4(*a*), each nanopore sensor footprint 101 accommodates a nanopore sensor 102, an sensor electrode 126, and integrated circuit 150. The sensor electrode 126 and integrated circuit can be arranged to inhibit noise interference created by the integrated circuit from being detected by the sensor electrode 126. For example, the integrated circuit 150 may be separated from the nanopore sensor 102, as depicted in FIG. 4(*a*). This separation can be implemented by configuring the integrated circuit 150 to be located outside the nanopore sensor footprint 101, as viewed.

This separation may simplify (e.g., simplifies) the manufacturing process. Alternatively, the integrated circuit 150 can be distanced from the sensor electrode (e.g., the distance between the electrode and the circuit in the depth direction, or thickness of the structure, and/or lateral distance is increased to minimise noise interference). Note that the depth direction of FIG. 4(*a*) is in a direction into and out of the page, as viewed.

In the example shown, the nanopore sensor footprint 101 is square and has a side length of 20 μm, but in other examples may be in a range from 10 μm to 50 μm. By way of example, the integrated circuit occupies about three-quarters of the footprint, while the remaining quarter is occupied by the sensor electrode 126 which has a diameter of 10 μm in the example shown.

Other arrangements are envisaged. In some embodiments, the sensor electrode 126 may be larger than the example shown in FIG. 4(*a*), for example covering almost all of the area of the nanopore sensor. In some embodiments, the sensor electrode 126 may be have other shapes covering more area, for example square or rectangular. The sensor electrode 126 may have dimensions of up to 50 μm, in which case it may have an area of up to 250 μm$^2$, depending on its shape. In some embodiments, pixels may be square or rectangular with a larges edge dimension between 5 microns and 60 microns.

For packaging efficiency, the pixel can be tessellated, and, for example, the tessellation can be hexagonal.

Each sensor 102 has a passage 114, although during fabrication of the base layer 112 more channels 122 could be created in the base layer 112 than are needed, depending on the method of fabrication. Some methods of fabrication such as reactive ion etching can etch a single channel for each footprint 101. Some other method such as photo assisted electrochemical etching requires a high-density array of channels to be etched at the same time to maintain the geometry of those channels—in this case unused channels in the base layer are blocked during fabrication of the array of nanopore structures 104 such that only one channel and one passage are provided per nanopore sensor footprint 101. The density of the channels 122 formed in the base layer 112 can vary. FIG. 4(*b*) shows, by way of comparison, a cross-section of a nanopore sensor having a lower density of blocked channels 122*a* than that shown in FIG. 4(*a*). The channels, as shown in FIG. 4(*b*) can be blocked prior to the sense layer 144 being added to the base layer, or may be blocked by a substrate of the sense layer. It is to be noted that FIG. 4(*b*) is shown with portions of two nanopore structures, each with its own passage 114, and has not yet had a nanopore layer 110 added upon the sense layer 144.

FIG. 4(*c*) shows the nanopore sensor 102 footprint 101 of FIG. 4(*a*) arranged in a 6×6 layout providing an array of nanopore structures 104 of 36 nanopore sensors, while FIG. 4(*d*) has an 18×18 array having 324 nanopore sensors. The array size can be 1000×1000, providing 1,000,000 nanopore sensors. In the present example, an array of one million sensors of the type shown in FIG. 4(*a*) would have a footprint of 4 cm$^2$, however sensors having pixels as small as 5 μm can bring the footprint of a one million sensor array down to around 25 mm$^2$. The array size can be 100,000. The array may comprise any number of sensors between 1000 and 10 million sensors.

FIG. 4(*e*) shows an array of nanopore structures 104 having nanopore sensors 102 as described herein arranged in a structure 100 provided in a device 149 for receiving and analysing an analyte of polymer such as nucleic acid. The array of nanopore structures 104 can be a sub-component of the device. The array can be a disposable component and replaceable. Additionally, or alternatively, the nanopore layer 110 of the array of nanopore structures 104 can be a disposable component and replaceable. While some of the inventive aspects relate to a device as a whole, some inventive aspects can also reside in the nanopore sensor 102 and/or the array of nanopore structures 104. The device 149 can include a connectable circuit 130 as described above.

In some embodiments, processing of the signals measured by a nanopore sensor can be performed by the circuit 130. In some embodiments, the integrated circuit 150 can perform pre-processing prior to further analysis by the circuit 130 of the device 149.

According to some embodiments, the device 149 houses the structure 100 to separate and define the analyte chamber 106 and outlet chamber 108. While often referred to, respectively, as the cis and the trans, the analyte can flow from the analyte chamber to the outlet chamber. The array of nanopore structures 104 has a plurality of nanopore sensors 102, each with a passage therethrough, to fluidly connect the cis and trans. By way of example, the electrodes 132 in the cis and trans can impose an electrical potential difference across the fluidic passage, between the first and second fluidic reservoirs, to induce an analyte to flow from the cis to the trans. The electrodes can be configured such that the potential difference is substantially the same across all the nanopore sensors 102.

Additionally, or alternatively, the device can be configured to induce an analyte from the cis to the trans using other techniques. As an analyte passes through a nanopore the fluctuation in electrical potential caused by changes in ion current flow is detected by the sensor electrode 126.

The sensor electrode 126 can function as, or connect directly to, the base of a transistor, which can be a gate of a field effect transistor (FET) device, for example. The transistor outputs a signal that can be processed by the integrated circuit 150 of each sensor 102, which can then be addressed in a row-column type manner. For example, the voltage at the drain of the transistor may depend upon the electrical potential sensed by the sensor electrode 126, and the voltage at the drain can be read out, along with other drain voltages on other nanopore sensors 102 in an array of nanopore structures 104, in a row-column manner. The processed signal(s) can then be analysed further—off the array of nanopore structures 104—to determine one or more properties of the analyte.

Figure 4F:
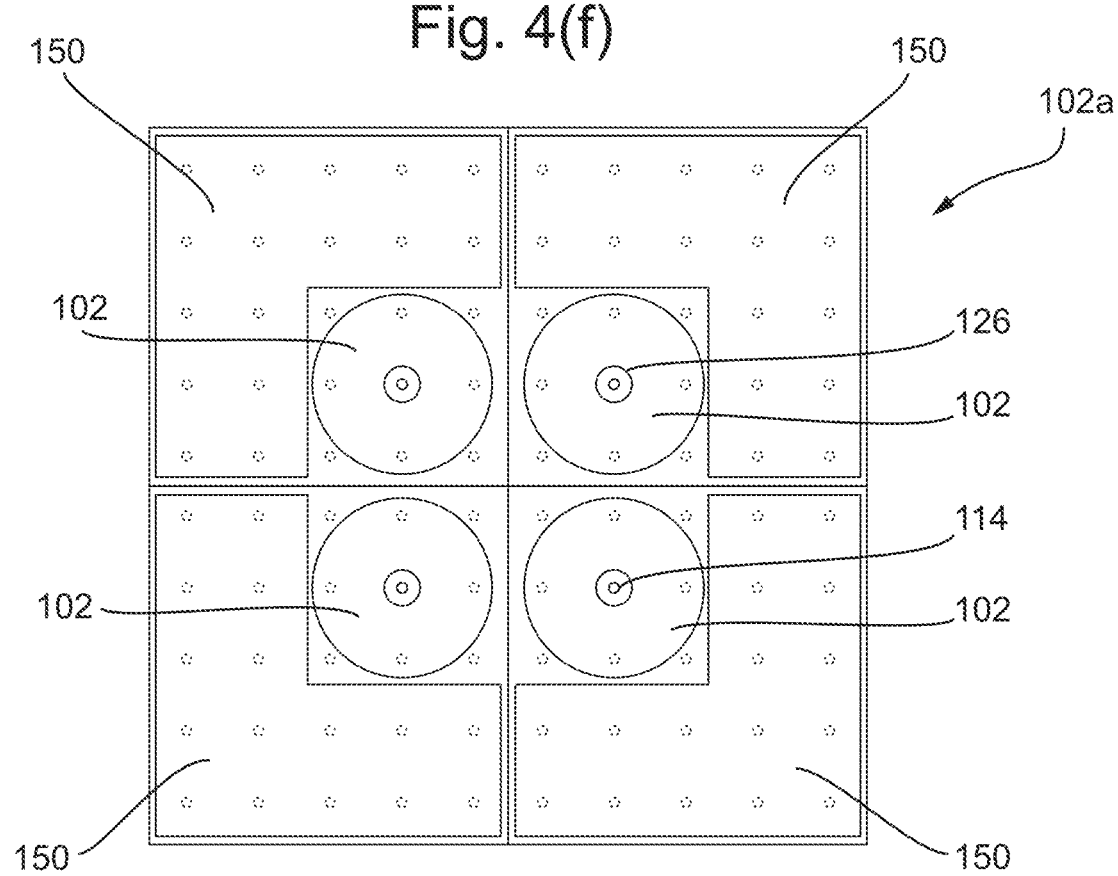
FIG. 4(f) is an alternative layout of four nanopore structures.

In the examples above, each nanopore sensor footprint 101 has its own integrated structure 150, but an integrated structure can be configured to serve a plurality of nanopore sensors. In FIG. 4(f), four nanopore sensors 102 are shown as a sensor module 102a, wherein the integrated circuit 150 is common to four centrally located electrodes, as shown. Other configurations are feasible. In such module configurations the information or data obtained from each individual sensor is addressable for control and/or retrieval of information. While the examples above have a dedicated integrated circuit for each nanopore sensor 102, combining nanopore sensors into a module enables the efficiency of the layout to be improved. Efficiency improvements can, for example, be achieved because a common filter is used for each of the nanopores within the module. This is possible if the integrated circuit switches or multiplexes between the individual nanopore sensors in turn. By sharing functions between the nanopore sensors either the footprint of the integrated circuit can be reduced or, alternatively, more functions can be accommodated.

Figure 5A:
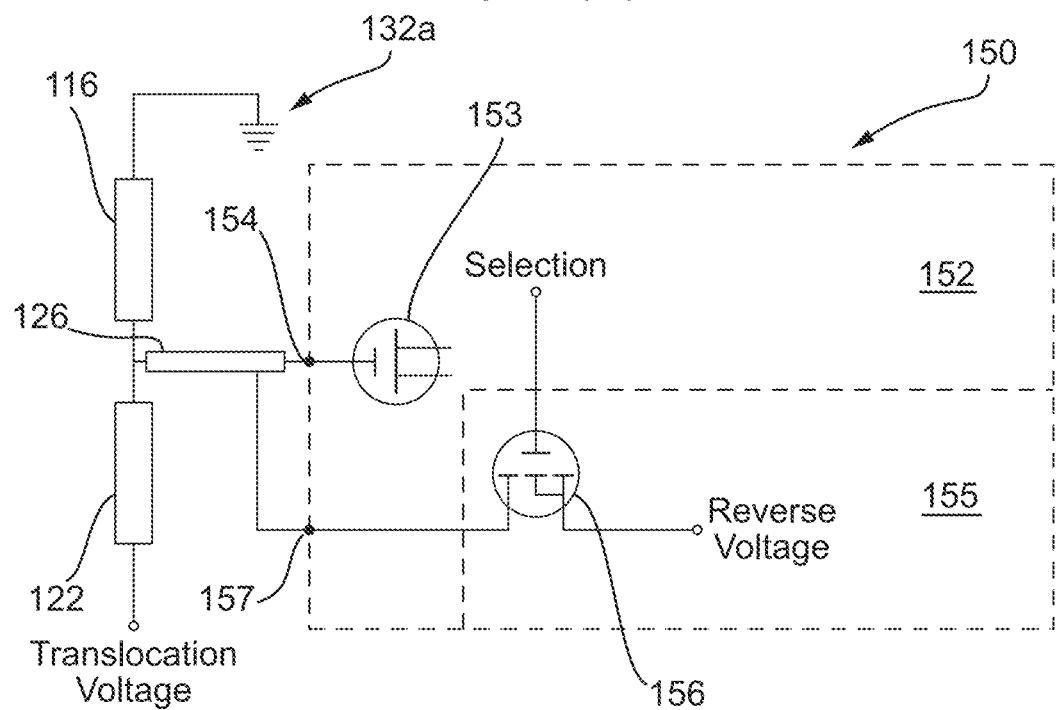
FIG. 5(a) illustrates example circuitry for interfacing with an electrical transduction element, according to some embodiments.

FIG. 5(a) is an example schematic representation of the connections to the sensor electrode 126 for each sensor 102 in the array of nanopore structures 104. In some embodiments, the cis electrode 132a can be connected to ground while a translocation voltage is applied to trans electrode 132b, though other configurations of applied voltage(s) and/or grounding may be used. The resistance of the nanopore 116 and the resistance of the channel 122, which is configured to function as a fluidic resistor, dominate the circuit between the electrodes via each passage 114 of each sensor 102. In this way the circuit behaves like a voltage divider having two resistors of similar value. The nanopore resistance and resistance of the channel or fluidic resistor, are approximately the same such that an electrode positioned therebetween is positioned to detect changes in the nanopore resistance caused by an analyte passing therethrough. The sensor electrode 126 resides, as described above, in the region of each nanopore. The sensor electrode 126 can lie between the nanopore and the channel. The effective impedance of the nanopore and the channel are much larger than the bulk fluidic resistance of the cis reservoir and trans reservoir—this means that FIG. 5(a) can be used to model the circuit between the electrodes.

The circuitry includes a sensing circuit 152 which is configured to detect changes in fluidic electrical potential at the sensor electrode 126 of the nanopore structure for producing signals from the nanopore that are indicative of analyte characteristics.

The sensing circuit 152 may include, for example a sensing transistor 153 which may be a field effect transistor (FET). In this case, the electrode 126 may be connected to the base of the sensing transistor 153. The sensing circuit 152 may reside, at least in part, in the integrated circuit 150. Thus, the sensor electrode 126 may be connected to a sensor terminal 154 of the sensing circuitry 152, as shown in FIG. 5(a).

In some cases, the sensor electrode 126 can additionally be connectable to a control circuit 155, as shown, which applies a signal to the sensor electrode to alter an electrical potential difference across the nanopore imposed by the drive electrodes 132 in response to a control signal. The control circuit 155 may include, for example a control transistor 156 which may be a field effect transistor (FET). In this case, the electrode 126 may be connected to the drain of the control transistor 156. The sensing circuitry and/or control circuitry 155 can reside, at least in part, in the integrated circuit 150. Thus, the sensor electrode 126 may be connected to a control transistor 156 of the control circuit 155, as shown in FIG. 5(a) for application of the control signal.

The application of the control signal enables an alteration of the potential difference imposed across the individual nanopore by altering the potential difference between the control connection of the control circuit 155 and the analyte electrode and/or the outlet electrode. The signal applied to the sensor electrode can be a reverse-voltage that induces the charged analyte, such as a species, to change the direction in which it is moving through the passage 114.

In some cases, the voltage applied can be an alternating current voltage, though other voltage waveforms (e.g., ramp, step, impulse, DC) may be applied.

The circuit of FIG. 5(a) enables a common electrode to be configured for each of the cis and trans reservoirs, while each nanopore sensor 102 can operate to detect an interruption to ion current flow across the passage by detecting variations in electrical potential caused by a variation in nanopore resistance. Furthermore, the circuit enables each nanopore sensor 102 within the array of nanopore structures 104 to be individually controlled to enable the sensor electrode to either detect an analyte passing through the pore through, for example, a connection with a sensing FET or control the flow of a charged analyte, such as a species, in the passage 114 of individual sensors 102 in the array of nanopore structures 104 by adjusting the voltage applied to the sensor electrode 126 using, for example, a control FET. The control of the flow of a charged analyte, such as a species, in the passage 114 of individual sensors 102 in the array allows for an analyte passing through the nanopore 116, or an analyte blocking the nanopore, to be passed back or ejected by a voltage applied by the control FET. This action can be described as "flicking" or "rejecting" and occurs by using a control voltage, such that an analyte passing from one side of the structure 100 through the passage 114 is modified—either stopped, reversed or accelerated. A control voltage can be applied to each pore, individually, because each sensor 102 is individually addressable for controlling and sensing. To be clear, the application of a control signal to the electrode 126 in each sensor 102 means that the voltage near the nanopore 116 at each pixel can be controlled.

The control voltage can be applied to alter the movement of an analyte through the nanopore 116 in response to at least one condition from conditions including: when a blocked pore is detected; when the analyte detected is no longer of interest and is to be ejected for the purposes of enabling another sample to be received and measured; and to alter the rate at which an analyte is induced into or out of the pore.

An electronic sensor, inevitably, has capacitances, resistances and inductances associated with the path along which the sensor signal travels, which may be referred to as parasitics. These are due to the properties of the materials the sensor is constructed from, the geometry of the sensor, and the methods by which it is feasible to fabricate the sensor. Without any kind of capacitance compensation, these parasitics (most commonly the resistances and capacitances)

interact to limit the bandwidth of the signal. In the simplest case, a resistor-capacitor circuit will limit the bandwidth to $1/(2\pi R C)$.

Figure 5B:
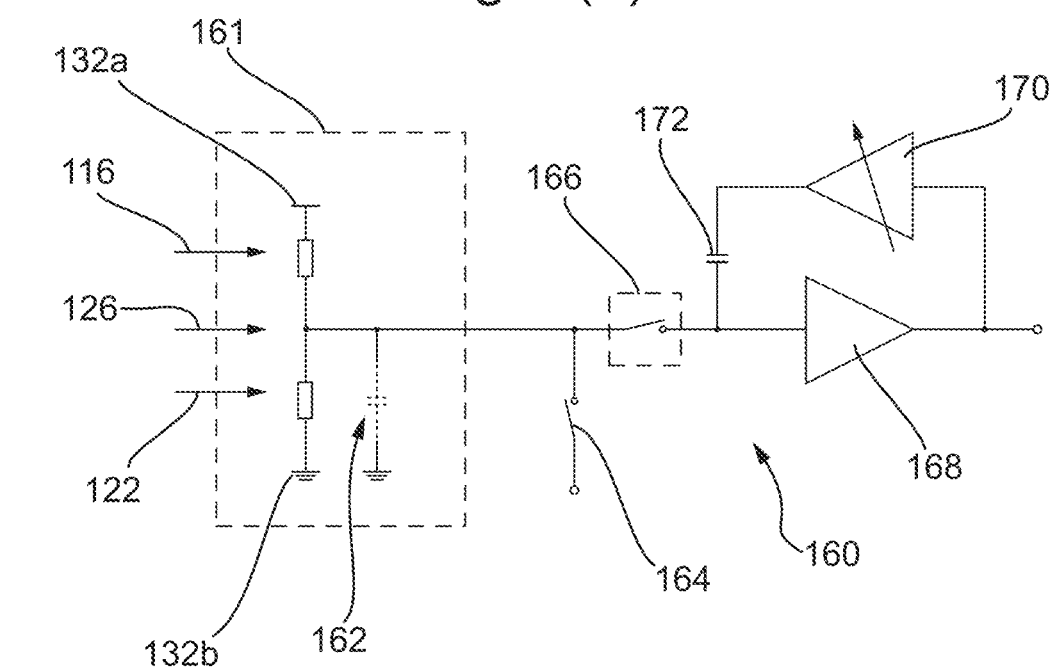
FIG. 5(b) illustrates example circuitry for interfacing with an electrical transduction element, according to some embodiments.

FIG. 5(b) is an alternative schematic of FIG. 5(a) that illustrates the resister model 161 of the nanopore 116 and the channel 122 and further includes a compensation circuit 160 connected to the voltage divider. According to some embodiments, a compensation circuit 160 has an inline amplifier 168, with gain G, connected to the output of the sensor electrode 126, which is influenced by the parasitic input capacitance 162. The output of the inline amplifier has a feedback loop connected to its input, said feedback loop having a feedback amplifier 170, with gain H, and a capacitor C representing compensation capacitance $C_{compensation}$.

A capacitor 162 is shown arranged in parallel with the resistor representing the channel 122, which represents parasitic capacitance in at least one of: the membrane in which the nanopore rests; the fluidic walls of the channel; the electrode; and a trace capacitance associated with a connector or wire-bond. The sensor electrode 126 is, in effect, connected to the mid-point in the voltage divider between the nanopore and channel and connected to the compensation circuit 160. The connection to a reverse or flicking voltage is represented by a flicking switch 164, such as a FET. An optional guard switch 166 is shown implemented between the sensor 126 and the compensation circuit. This switch, which can be implemented using a FET, can function to isolate the compensation circuit 160 and/or any sensing circuitry connected thereto from the flicking voltage applied via the flicking switch 164.

Overall, the compensation circuit 160 mitigates the effects of the total parasitic capacitance 162 at the input to the sensing stage. Although the parasitic capacitance resides in various elements of the sensor 102 it can be modelled as shown in FIG. 5(b). Without being bound to a particular theory, a total parasitic capacitance 162 $C_p$ can be considered as a sum of various parasitic capacitances, as follows.

$$C_p = C_{membrane} + C_{fluidic\ walls} + C_{electrode} + C_{trace}$$

The rate at which the input capacitance charges is proportional to the current flowing through it. In turn, the resistance limits the charging current to a finite value. The compensation circuit 160 functions to supply additional current to charge the input capacitance faster, thus increasing the bandwidth.

In some embodiments, the input voltage is amplified and fed back through the compensation capacitor so as to provide additional current to charge the total parasitic capacitance 162. According to some embodiments, an effective input capacitance of this circuit can be expressed as:

$$C_{effective} = C_p - C_{compensation}$$

wherein $$C_{compensation} = C^*(G^*H - 1)$$

The components of the compensation circuit 160 are configured such that the total parasitic capacitance $C_p$ is substantially negated or cancelled. In practice, the degree of compensation is limited by dynamic changes in the component values and parameters (e.g. temperature dependence). The compensation circuit can compensate for a range of different parasitic capacitance values if capacitance C, inline gain G or feedback gain H is made adjustable, hence the feedback amplifier is illustrated as variable in FIG. 5(b). The gain G can be fixed such that the output from the compensation circuit has a consistent gain, therefore either the capacitor C and/or the feedback gain H can be varied.

Figure 5C:
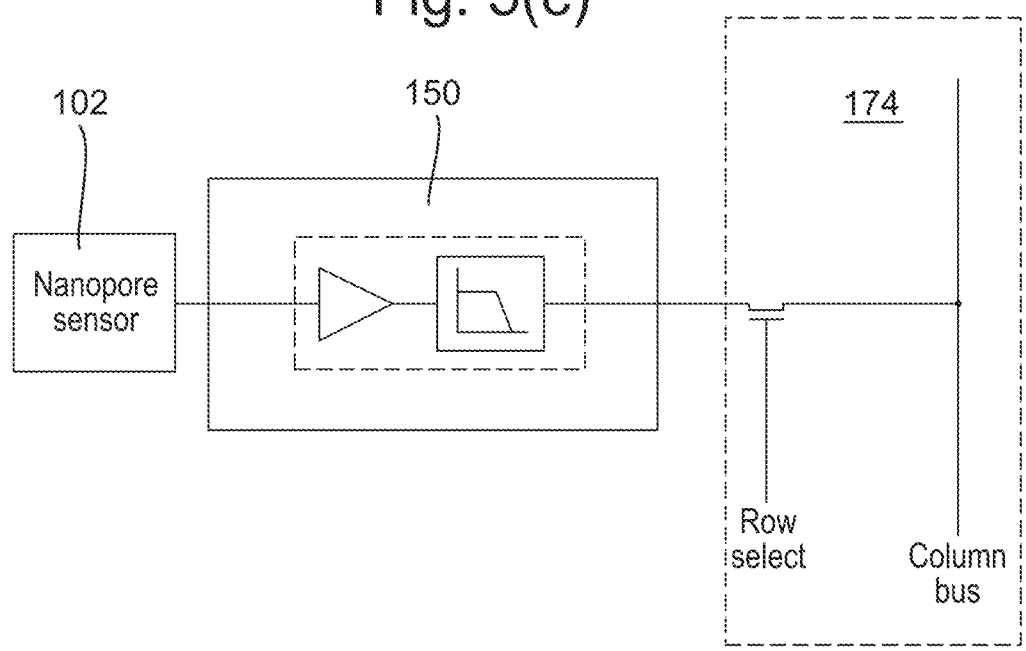
FIG. 5(c) illustrates example circuitry for interfacing with an electrical transduction element, according to some embodiments.

The front-end electronics can reside, at least in part, in the integrated circuit 150, which is figuratively represented in FIG. 5(c). In some embodiments, the control circuit 155 and/or compensation circuit 160 can optionally be incorporated within the integrated circuit 150. The integrated circuit or electronic circuit is operable to influence the movement of an analyte in the nanopore, such as by flicking, by applying a reverse voltage, and amplifying the signal from the nanopore sensor 102. The integrated circuit 150 or electronic circuit 130 can additionally incorporate further processing of the signal, such as filtering, and may include circuitry to store information locally at the sensor 102, in the case of the integrated circuit, for managed communication with an external processor.

Figure 3A:
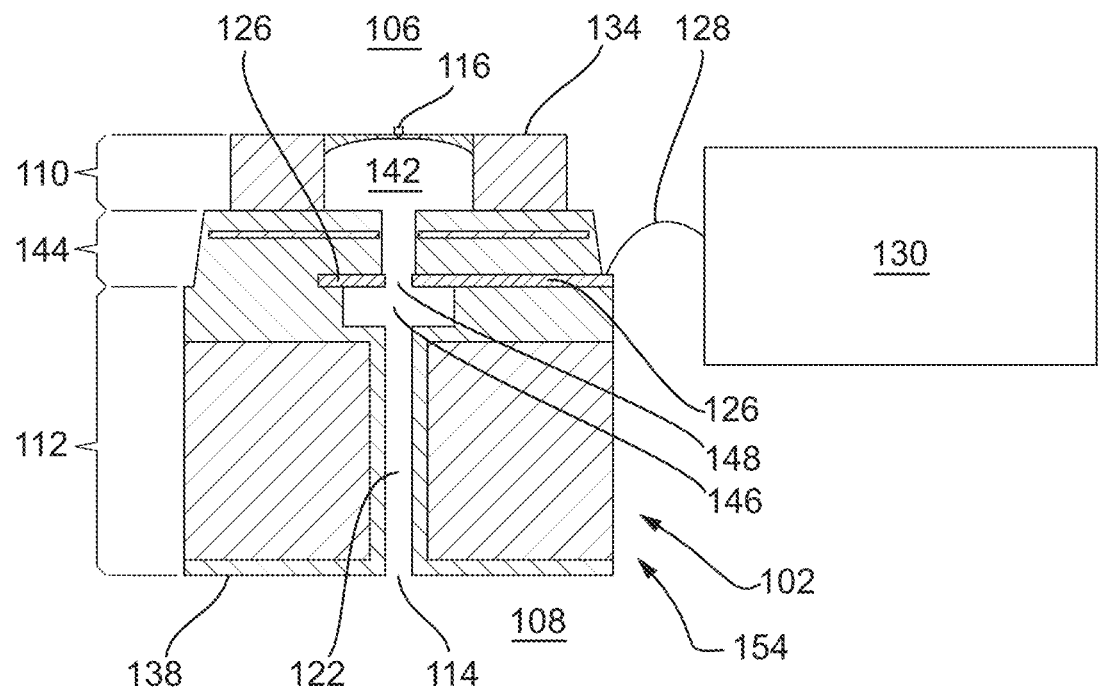
FIG. 3(a) is an alternative cross-section of a single sensor electrode, and corresponding biological nanopore, the sensor electrode configured on a sensor layer that is sandwiched between a nanopore layer and a base layer within a portion of a structure of a nanopore sensor array, wherein the sensor electrode is connected via a wire to an electronic circuit, according to some embodiments.
Figure 3B:
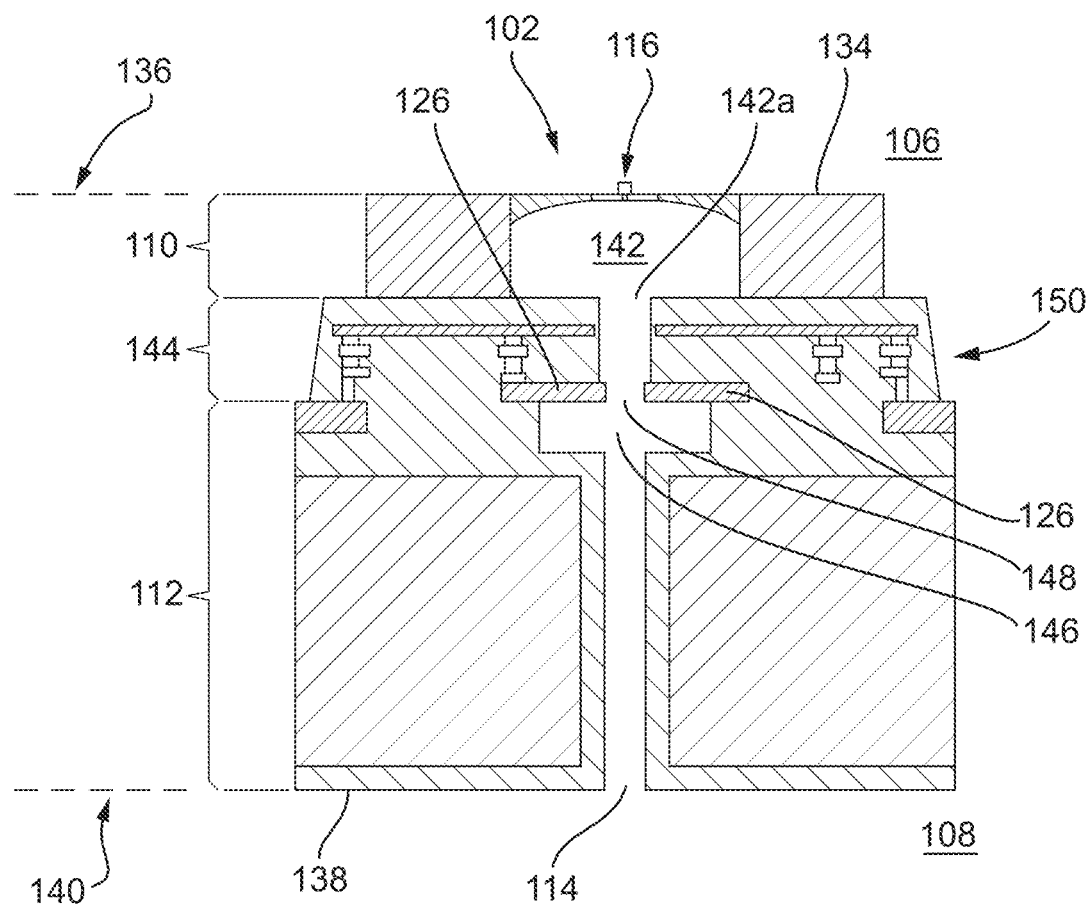
FIG. 3(b) is comparable to FIG. 3(a) wherein the sensor layer incorporates electronic circuitry.
Figure 5D:
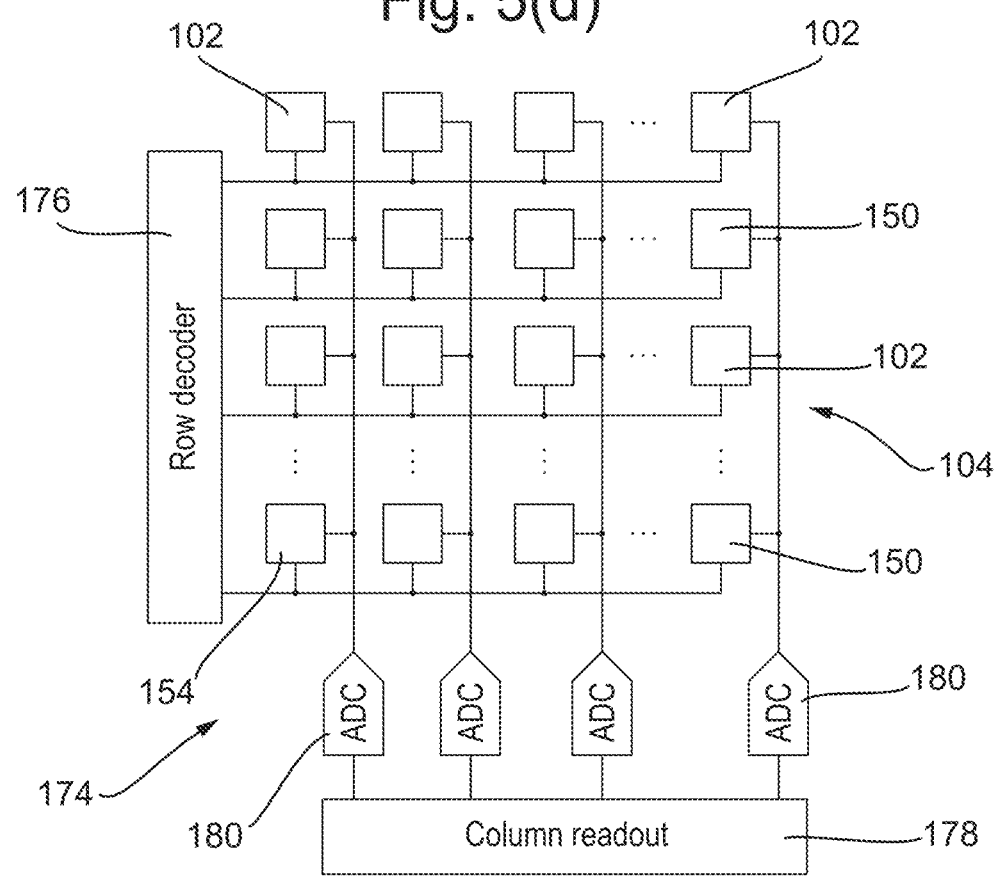
FIG. 5(d) illustrates example circuitry for interfacing with a plurality of electrical transduction elements, according to some embodiments.

According to some embodiments, each nanopore sensor 102, such as those illustrated in FIG. 2 and FIG. 3(a), can be addressable. FIG. 5(c) represents the nanopore sensor 102 of FIG. 3(b) that incorporates the integrated circuit 150 within a nanopore sensor footprint 101, as shown in FIG. 4(a) for example, and is also addressable via row-selection and column bus. FIG. 5(d) is an example of a row-column readout circuit 174 connected to each sensor 102 in an array of nanopore structures 104, such as the array shown in FIG. 4(d), via a row-selection and column bus connection shown in FIG. 5(c). Each sensor 102 is connected to a row decoder 176 and column readout 178 via an analogue to digital converter 180. The readout circuit 174 can be connected to the integrated circuit 150 of each sensor 102 or group of sensors in some embodiments, or may be connected directly to the sensor electrode 126 in each nanopore sensor 102 within the array of nanopore structures 104.

The examples above describe the sensor electrode 126 being connectable to an integrated circuit 150 and having the option of dual functionality when a control voltage is applied (i.e. the sensor electrode 126 can be used to sense the change of ion flow when an analyte passes through a nanopore and create an electrical potential within the passage and a potential difference across the passage between the cis and or trans electrodes 132 under the control of the control circuit 155). In this case, the sensor electrode 126 is directly connected to a control terminal, which is a terminal of the integrated circuit 150, for creating a potential difference across the passage. In some embodiments, the sensor electrode 126 can be connected to a control terminal, which is a terminal of the integrated circuit 150, for creating a potential difference across the passage.

Figure 6A:
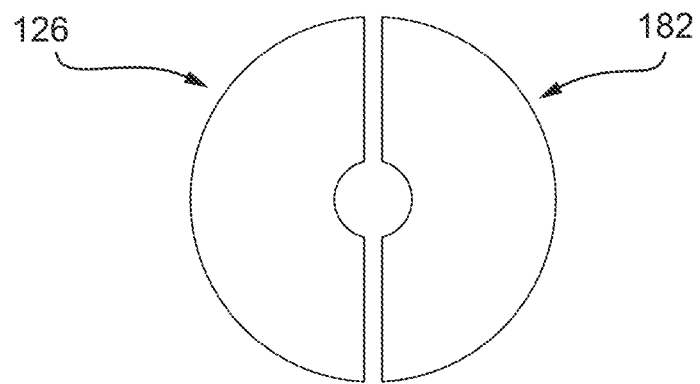
FIGS. 6(a) depicts an electrical transduction element in plan view, according to some embodiments.
Figure 6B:
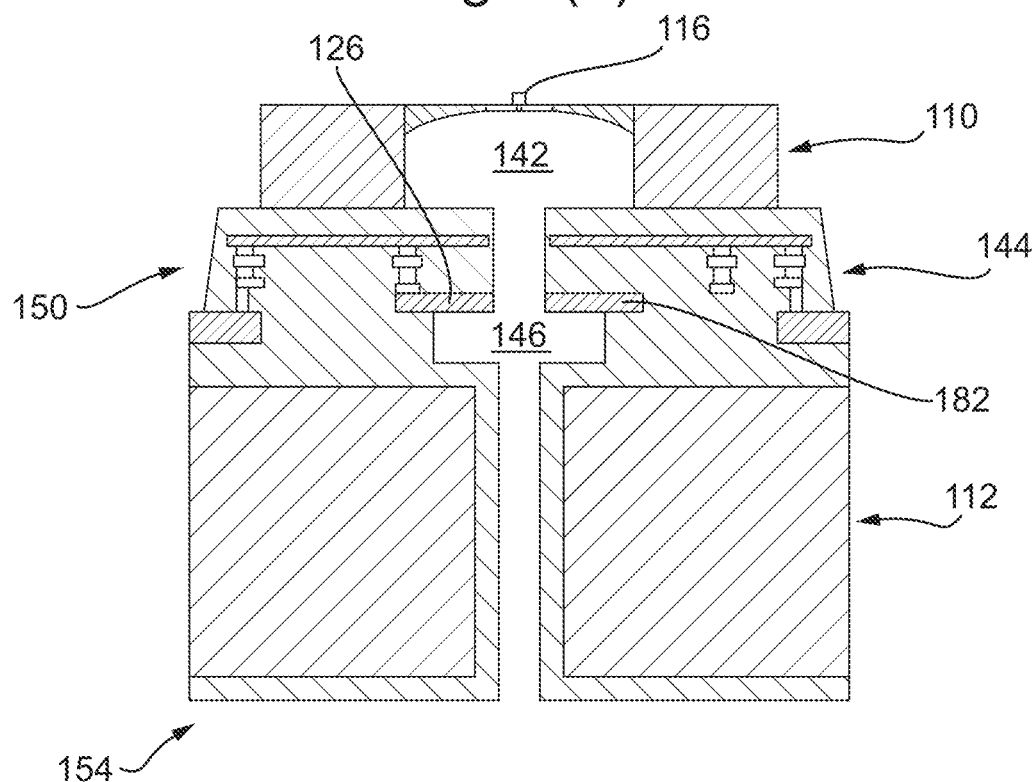
FIG. 6(b) depicts a cross section of a sensor electrode and control electrode configured in a sensor of the array, according to some embodiments.
Figure 6C:
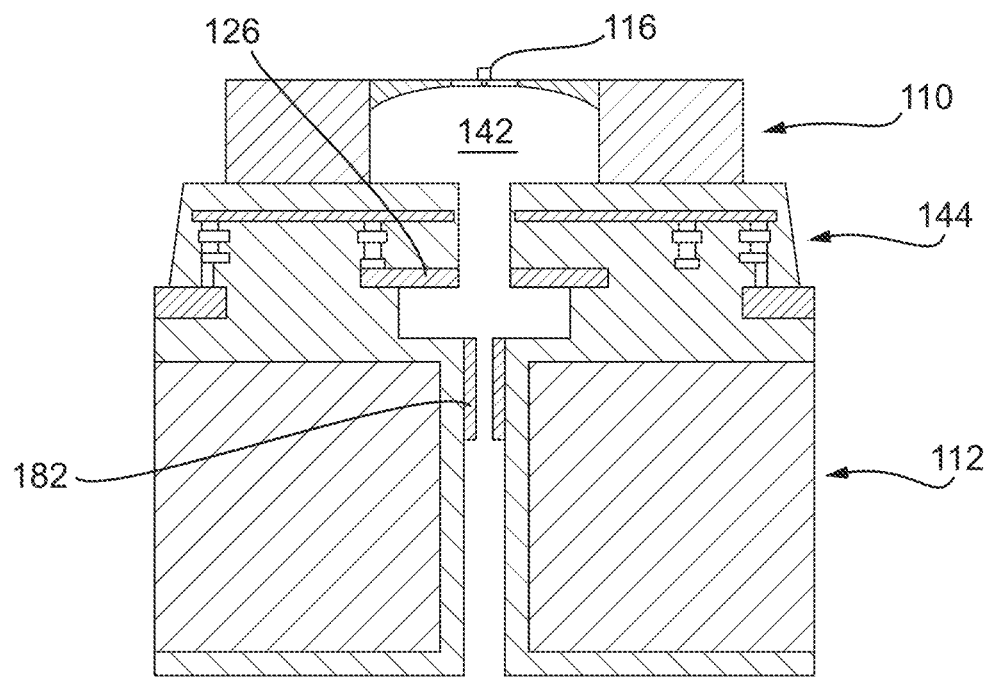
FIG. 6(c) depicts a cross section of a sensor electrode and control electrode configured in a sensor of the array, according to some embodiments.
Figure 6D:
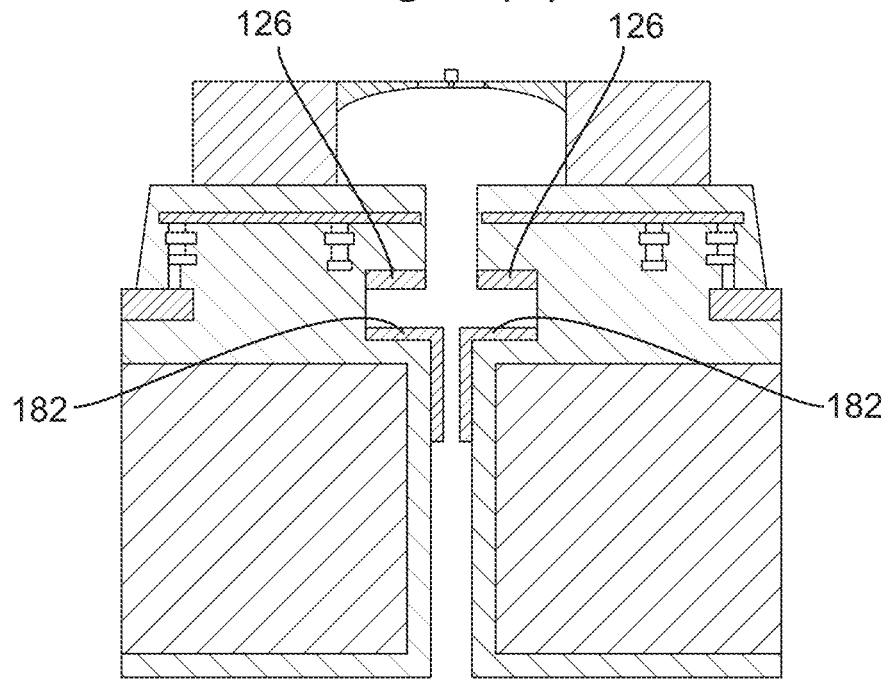
FIG. 6(d) depicts a cross section of a sensor electrode and control electrode configured in a sensor of the array, according to some embodiments.
Figure 6E:
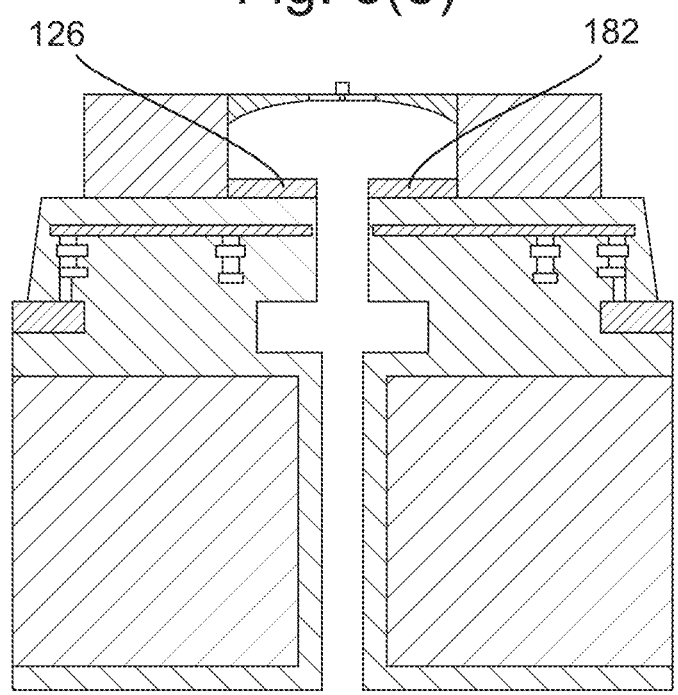
FIG. 6(e) depicts a cross section of a sensor electrode and control electrode configured in a sensor of the array, according to some embodiments.

In some implementations, the sensing and control functions in each sensor 102 can be implemented by separate electrodes. FIG. 6(a) shows a sensor electrode 126 and control electrode 182 arranged like an annulus, while FIGS. 6(b) to 6(e) are cross-sectional schematics of nanopore sensors 102 having configurations in which a control electrode 182 is provided in addition to the sensor electrode 126. In this case, the control electrode 182 is connected to a control terminal of the control circuit 155 for creating the electrical potential within the passage. In some embodiments, the control electrode 182 can be connected to a sensing circuit but additionally or alternatively can be connected to a control terminal of the control circuit 155 for creating the electrical potential within the passage.

In an example herein, the sensor electrode 126 has been described as an annulus, as illustrated in FIG. 4(a). The sensor electrode could also be implemented by an exposed wire. The sensor electrode could be a nanowire, but can be a larger surface area that occupies, for example, substantially all of the base of a well 142, as shown in FIG. 6(*e*), or one face of a recess 146. Similarly, a separate control electrode 182 could be a nanowire but can have a large surface area, as shown in FIG. 6(*d*).

From a manufacturability and cost perspective, a basic implementation of a control electrode 182 is shown in FIG. 6(*a*), wherein the annulus footprint—suitable for the base of a well 142—is substantially maintained, while one half of the footprint forms the sensor electrode 126 and the other half, which is physically disconnected or decoupled from sensor side, forms the control electrode 182. There is no wired or solid-state connection between the sensor electrode 126 and the control electrode 182. The electrodes 126, 182 are shown having two equally sized semi-circle shapes occupying the footprint. In some embodiments, the electrodes can be different sizes, and, for example, the control electrode can have a greater surface area than the sensor electrode to increase the conductivity with the fluid within the passage.

Having separate sensor and control electrodes can simplify the integrated circuit because, by being separate, an extra degree of separation is provided, although they will still be connected through a fluid in the passage. However, it can be possible to avoid the need of isolating switch to protect, for example, the compensation circuit 160, which can form part of the sensing circuit, from the voltages applied by the control circuit. The electrodes can be tailored in shape, size and configuration to be optimised for their purpose.

FIG. 6(*b*) indicates how the electrode of FIG. 3(*b*) can be divided into separate sensor electrode 126 and control electrode 182. In this example the electrodes extend in the same plane. In an alternative configuration shown in FIG. 6(*c*) the sense electrodes reside in the cavity 146 and extend in a plane extending in parallel with the cis-surface 134 and trans-surface 138, while the control electrodes extend in the channel 122 and extend perpendicularly from said surfaces. In FIG. 6(*c*) the sensor electrode 126 is shaped like an annulus while the control electrode is shaped like a cylinder. In yet another alternative, as shown in FIG. 6(*d*), the sense electrodes reside in the cavity 146 and extend in a plane extending in parallel with the cis-surface 134 and trans-surface 138, while the control electrodes extend in the channel 122 and in the cavity 146, thus extending in vertical and horizontal planes, as viewed. FIG. 6(*e*), which is similar to FIG. 6(*b*), shows the electrodes 126, 182 formed at the base of the well 142, which can offer easier fabrication.

As described above, an electronic sensor inevitably has capacitances, resistances and inductances associated with the path along which the sensor signal travels, which may be referred to as parasitics, which includes parasitic capacitances. Additionally, or alternatively to the compensation circuit 160 described above, the array of nanopore structures 104 and sensors therein can be fabricated with a guard conductor 184 incorporated therein, as shown in FIGS. 7(*b*) to 7(*d*), while FIG. 7(*a*) shows first and second schematic circuits 201, 202 with and without a guard conductor 184 in order to illustrate how a guard conductor 184 is configured. In the left-hand first schematic circuit 201 of FIG. 7(*a*), the parasitic capacitance $C_{parasitic}$ is shown between two conductive elements 203, 204 of the sensor 102, typically being a conductor, such as the sensor electrode 126 and a conductive substrate of the base layer. The first conductive element 203 (e.g. sensor electrode 126) may carry a voltage $V_{sensor}$ and the second conductive element 204 (e.g. the conductive substrate) may carry a different voltage $V_{substrate}$.

Guarding is shown implemented in the right-hand, second schematic circuit 202, wherein the guard conductor 184 which is a third conductive element is configured between the first conductive element 203 carrying the signal and the second conductive element 204 such that two parasitic capacitances $C_{par1}$, $C_{par2}$ can be modelled as connected in series. In this schematic 202, the parasitic capacitance occurs (i) between the first conductive element 203 or conductor carrying the signal and the guard conductor 184 (i.e. $C_{par1}$) and (ii) between the guard conductor 184 and the second conductive element 204 (i.e. $C_{par2}$). According to some embodiments, a buffer 205 (which may be an amplifier) is connected between the first conductive element 203 and the guard conductor 184 to apply a buffered version of the input signal is applied to the guard conductor 184. As a result, there is no voltage difference across the parasitic capacitance $C_{par1}$ between the first conductive element 203 and the guard conductor 184.

For a capacitor, the current is given by $$I = C \frac{dV}{dt}$$

In the right-hand schematic, $V_{guard} = V_{sensor}$, thus $$\frac{dV}{dt} = 0.$$

No current flows through the capacitor $C_{par1}$, thus the effective capacitance is zero. The capacitance between the guard and the substrate conductors must still be charged, but the buffer 205 is able to supply much more current than the high-impedance sensor input, so it charges much faster.

These conditions are met when $V_{guard}$ accurately follows $V_{sensor}$, which depends on the performance of the buffer 205 having sufficient bandwidth to enable the capacitance to be nulled. Precise buffers with bandwidths of several MHz can be implemented.

FIG. 7(*b*) is analogous to FIG. 2(*b*) and shows, by way of comparison, a guard conductor 184 extending between oxide layers 192 along the length of the channel 122, vertically as viewed, and continues horizontally, as viewed, along the top of the base layer 112 beneath the sensor electrode 126. Notably, both the sensor electrode 126 and the guard conductor 184 are connected to the separate electronic circuit 130. In this configuration the guard conductor inhibits current flow in the parasitic capacitance between the sensor electrode and the substrate of the base layer. The conductive guard can include, at least in part, a guard conductor and an insulating layer that insulates the guard conductor from the conductor being guarded or the conductor being guarded from. The insulating layer is not part of the guard and functions to isolate the guard from surrounding conductors. The insulating layer, therefore, can be a non-conductive component of the structure 100. The guard can be a conductor inserted into the middle of the parasitic capacitances to divide them in two, which is possible because capacitors are by nature insulators, thus the guard is located in an existing insulating layer.

Figure 7A:
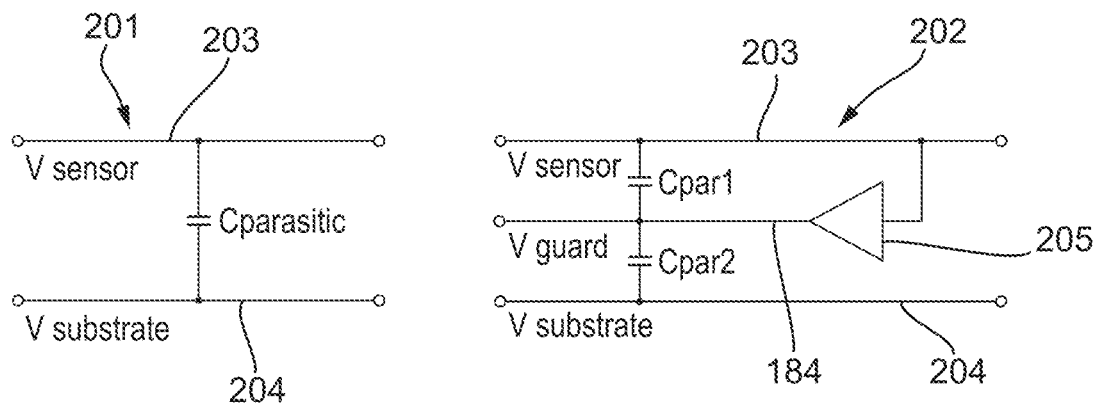
FIG. 7(a) depicts, respectively, two schematic circuits illustrating the parasitic capacitance in the array with and without guarding.
Figure 7B:
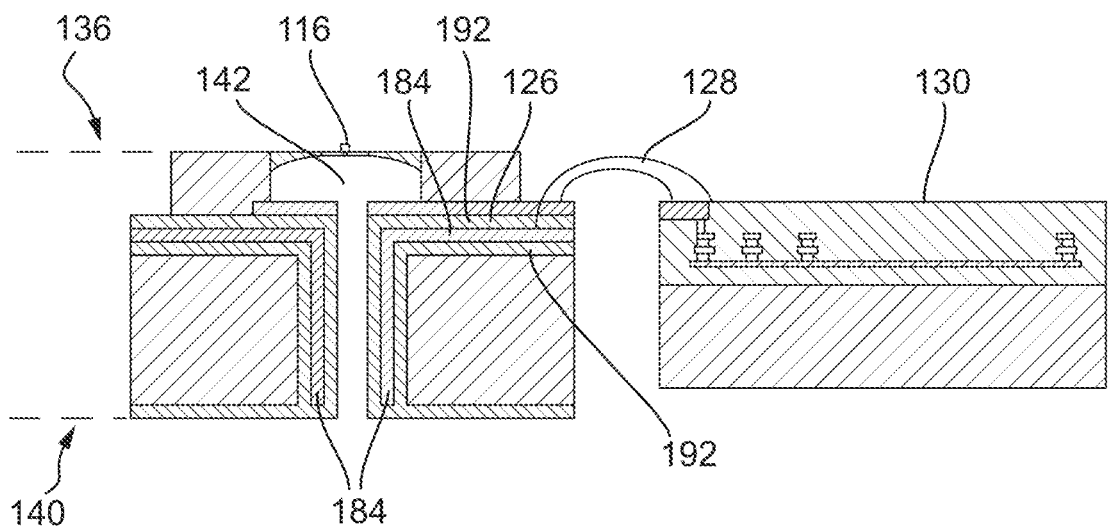
FIG. 7(b) depicts an alternative cross-sectional view to that shown in FIG. 2, in which a guard conductor is configured in the structure and connected via an additional wire to the measurement circuit, according to some embodiments.
Figure 7C:
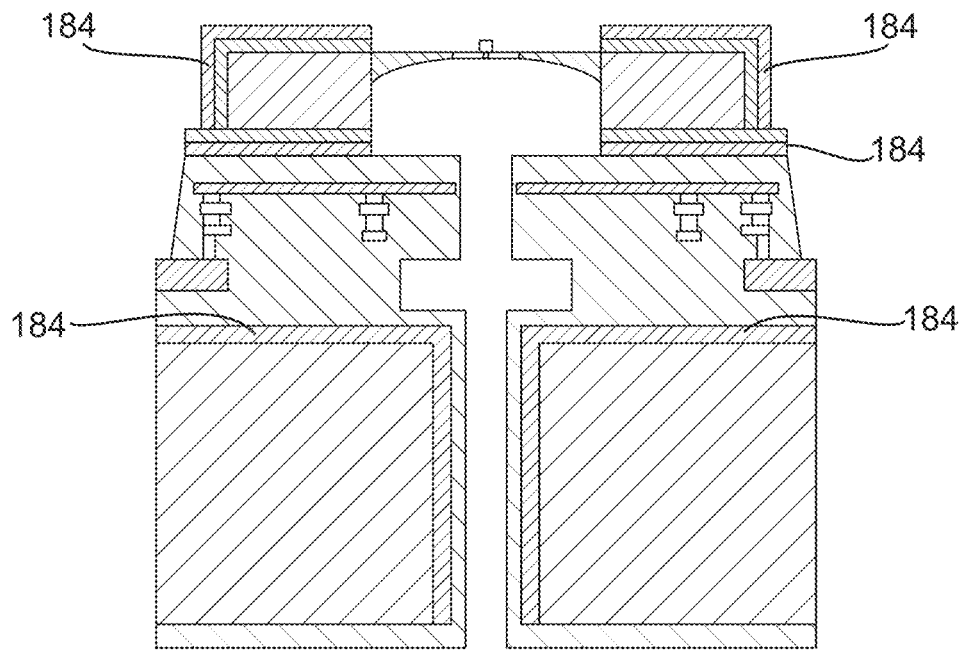
FIG. 7(c) depicts an alternative cross section of a nanopore structure in which guarding is implemented.
Figure 7D:
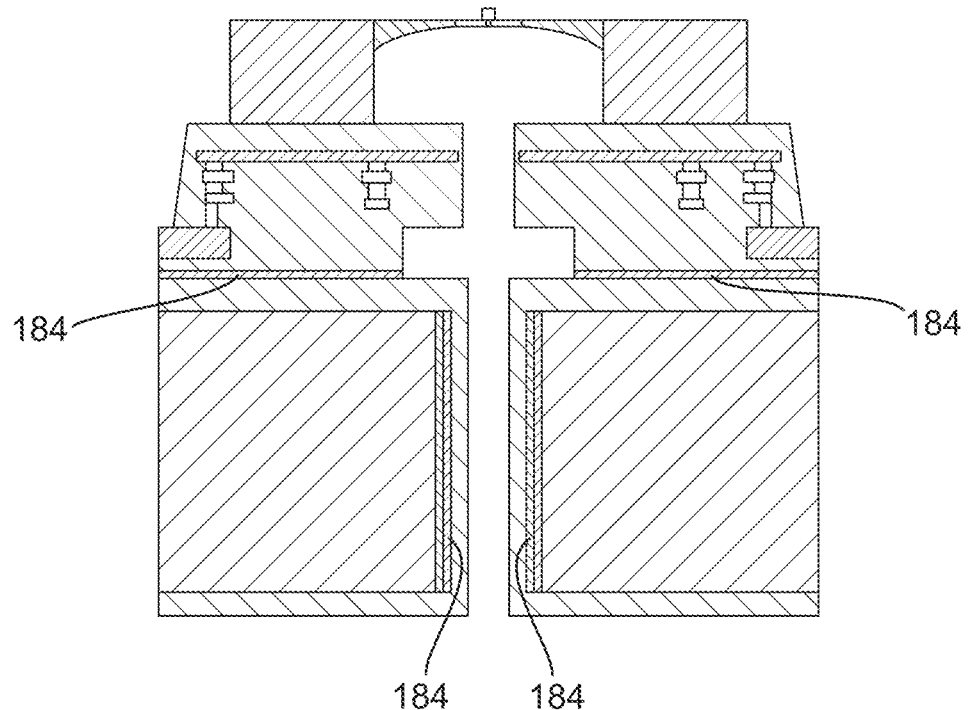
FIG. 7(d) depicts an alternative cross section of a nanopore structure in which guarding is configured.

The guard conductor 184, including an insulating layer, can be configured in a number of different configurations, or combination thereof, comprising at least one of: extending over at least a portion of the nanopore layer 110 for separating the nanopore layer from an analyte in the analyte chamber 106, as shown in FIG. 7(c), which guards the solution underneath the nanopore from the solution above; extending between the at least a portion of the nanopore layer 110 and the sense layer 144 for separating the sensor electrode 126 and integrated circuit 150 from the solution in the cis 106, as also shown in FIG. 7(c); extending between the base layer 112 and the sense layer 144, at least in part, for separating the sensor electrode 126 and integrated circuit 150 from the base layer, as also shown in FIG. 7(c); and a plurality of conductive guards, as shown in FIG. 7(d), wherein a first guard extends between the walls of the channel 122 and the base layer 112 and a second guard extends between the sense layer 144 and the base layer.

In light of the teaching herein a skilled person would appreciate that one of the guard arrangements taught herein, or a combination thereof, could be implemented. It will also be appreciated that the guard conductor 184 can be provided in an array of nanopore structures, e.g. the array of FIG. 4(c).

It is to be noted that guard-based capacitance compensation techniques, shown in FIGS. 7(a) to 7(d) have the advantage that they generally do not appreciably increase the noise level of the signal. However, such a technique cannot compensate for the membrane capacitance when a potential difference across the membrane is used to drive the analyte being studied through the pore, but it may be possible to drive the analyte by another means, e.g. pressure. A compensation circuit 160, on the other hand, can compensate for the entire input capacitance, but does so at the expense of added noise. The noise gain of the feedback capacitor 172 increases with frequency. Therefore, the noise in the input signal is scaled by this feedback gain 'G' and adds to the overall noise. This becomes significant at higher frequencies or when compensating for larger input capacitances. The guard conductors shown in FIGS. 7(b) to (d) can, therefore, be implemented in the array of nanopore structures 104 in any combination and/or in combination with a compensation circuit 160.

The sensors 102 can be manufactured using a number of different techniques and the functions are taught, by way of example with reference to FIG. 2, which is indicative of the other sensors taught in the application. Although only one of the sensors 102 of the array of nanopore structures 104 is shown in FIG. 2, the fabrication of an array can be understood from the teaching herein. The base layer 112 is formed from a standard silicon (Si) wafer that has channels 122 formed therein to pass from one side of the layer to the other. Only one channel is shown in FIG. 2, formed through the Si wafer extending substantially perpendicularly to the surfaces of the wafer. In practice, the array has channels formed across the wafer using techniques such as photolithography or deep reactive-ion etching (DRIE) or combinations thereof. At least one channel is formed for each sensor. Techniques such as thermal oxidation can be used to adjust the diameter of the channel to calibrate the aspect ratio, if required. In some cases, the channels can be embedded in an oxide layer, which may be formed on a silicon wafer, for example.

The example of FIG. 2 schematically shows a portion of the structure 100 having an array of nanopore structures 104 of nanopore sensors 102 (only one of which is shown) and is configured to separate a cis and trans having electrodes 132 therein. All of the sensors 102 herein can be located in a structure as shown in FIG. 4(e). The nanopore 116 lies in the passage 114 between the cis and the trans, which are fluid filled. The passage is fluid filled such that the cis and trans are fluidically connected. To be clear, the nanopore lies in a path of fluidic communication between the analyte chamber 106 and outlet chamber 108.

Figure 8:
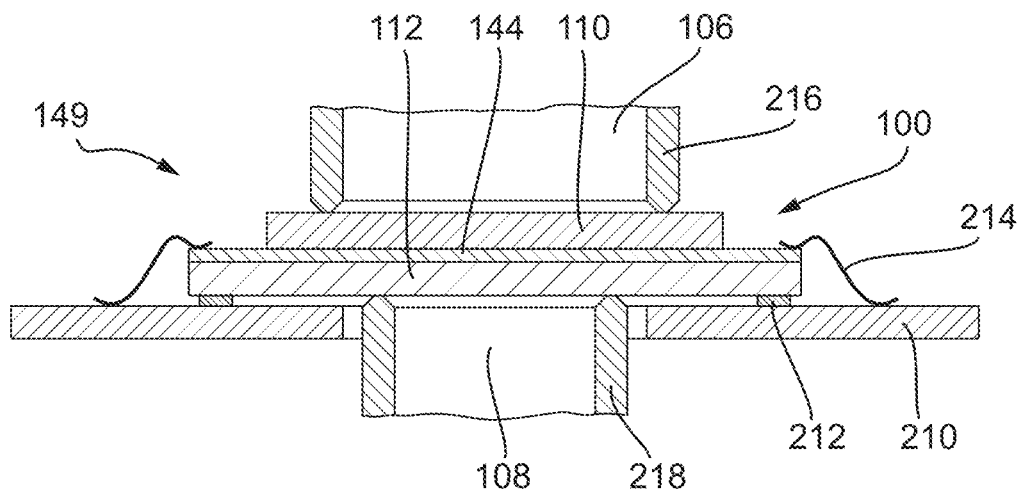
FIG. 8 and FIG. 9 show two examples of a device 149 including a structure 100.
Figure 9:
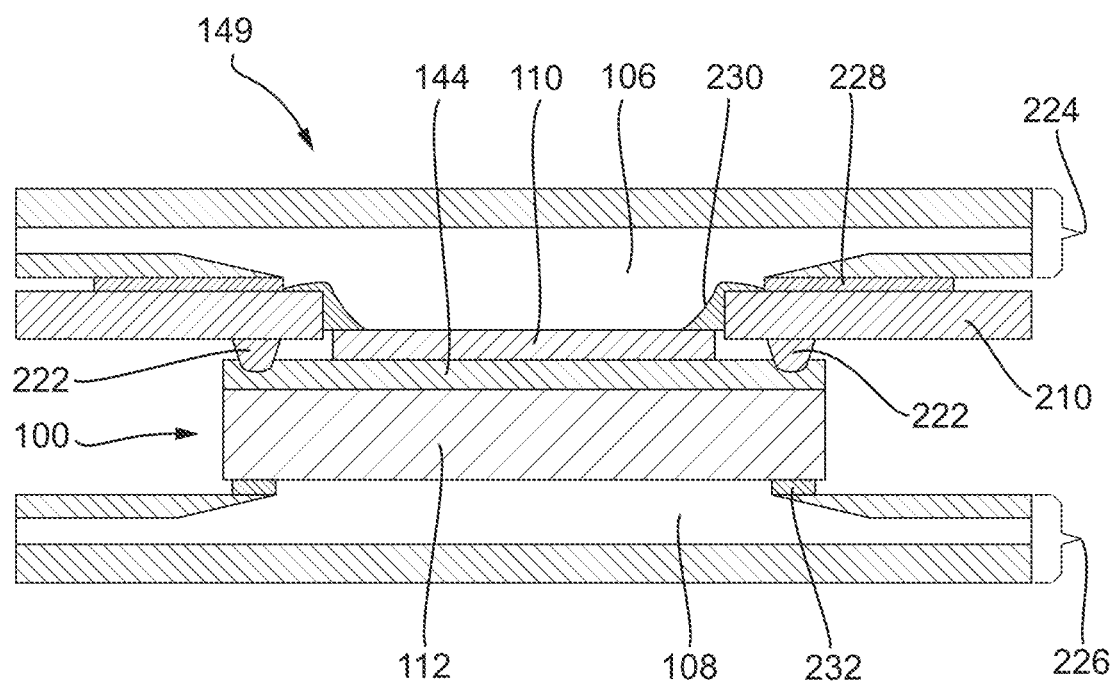

FIGS. 8 and 9 show two further examples of a device 149 including incorporating a structure 100. In each case, the structure 100 takes the form shown in either FIG. 3(a) or 3(b) including a nanopore layer 110, a sense layer 144 and a base layer 112, as described in detail above (although in each case it could be replaced by a structure 100 taking the form shown in FIG. 2).

In each of the examples of FIGS. 8 and 9, the structure 100 separates the analyte chamber 106 and the outlet chamber 108 and is connected to a printed circuit board 210 but with different configurations as follows.

In the example of FIG. 8, the analyte chamber 106 and the outlet chamber 108 are each formed by respective gaskets 216, 218 which seal against the nanopore layer 110 and the base layer 112, respectively. The analyte chamber 106 and the outlet chamber 108 may be open as shown in FIG. 8 or may be closed, for example by respective members extending across the gaskets 216, 218.

In the example of FIG. 8, the printed circuit board 210 is mounted to the base layer 112 by a mechanical bond 212 (e.g. adhesive) on the opposite side from the nanopore layer 110. Thus, the printed circuit board 210 is disposed outside the outlet chamber 108, as shown in FIG. 8. The sense layer 144 is connected to the printed circuit board 210 by a wire bond 214, or any other suitable electrical connection. The nanopore layer 110 has a smaller area than the sense layer 144 to provide space for the wire bond 214.

In the example of FIG. 9, the printed circuit board 210 is mounted to the sense layer 144 by a solder bump connection 222 (e.g. adhesive) on the same side as the nanopore layer 110. Thus the nanopore layer 110 has a smaller area than the sense layer 144 to provide space for the solder bump connection 222. The solder bump connection 222 provides both mechanical and electrical connection between the printed circuit board 210 and the sense layer 144.

In the example of FIG. 9, the analyte chamber 106 and the outlet chamber 108 are each formed in respective flowcells 224, 226 which may be made of any suitable material, for example plastic. The flowcells 224, 226 allow flow of fluid into and out of the analyte chamber 106 and the outlet chamber 108.

The flowcell 224 that forms the analyte chamber 106 is sealed to the printed circuit board 210 around the analyte chamber 106 by a gasket 228, and the printed circuit board 210 is sealed to the edges of the nanopore layer 110 around the analyte chamber 106 by a sealant 230.

The flowcell 224 that forms the outlet chamber 108 is sealed to the base layer 112 around the outlet chamber 108 by a gasket 232.

The examples of FIGS. 8 and 9 can be modified in various ways, for example to provide sealing in other locations (e.g. around the outside edge of the base layer 112) and by any suitable means.

The electrical model of a nanopore sensor has been described above. More generally, a voltage source, not shown in FIG. 2, applies a potential difference between the electrodes configured in the chambers 106, 108. The electrodes impose an electrical potential across the passage 114, including the nanopore 116 and channel 120. The nanopore resistance and channel resistance are significantly higher than the overall fluidic resistance of the reservoirs and, therefore, the nanopore and channel are the dominant components in an equivalent electrical circuit. As shown in FIG. 2, the sensor electrode 126 lies between the nanopore and channel such that it can sense the fluidic electrical potential at the sensor electrode in the passage 114. In other words, the sensor electrode can sense a signal indicative of local electrical potential fluctuations in the passage. Although the configuration in FIG. 2 is an example, the sensor electrode 126 can be located in the cis 106 or trans 108. The sensor electrode 126 can function as the base or gate of a transistor device for measuring electrical potential of the fluid at the location of the sensor electrode 126 when a fluid is provided in the passage. The sensor electrode 126 can detect fluctuations in voltage as a species object, such as a strand of DNA, translocates through the nanopore 126.

The embodiments herein have described a device having a single sample reservoir separated from a single outlet chamber by the structure 100. In light of the teaching herein alternative arrangements can be implemented and include a device having (i) two or more sample reservoirs separated from a common outlet chamber by the structure, (ii) a common sample reservoir separated from two or more outlet chambers by the structure, or (iii) two or more sample reservoirs separated from two or more respective outlet chambers by the structure.

The nanopore layer 110 can be formed separately having an array of wells that can be formed in a number of ways, one of which is by lithographically patterning a polymer layer. The wells in the nanopore layer are then aligned with the channels of the base layer such that each sensor 102 has a passage 114 defined by the well 142 and channel 122. The well 142 shown in FIG. 2 is substantial in comparison to the nanopore 116 located in the membrane 118. The nanopore of FIG. 2 is a biological nanopore in a membrane such as an amphiphilic membrane. Alternatively, each nanopore can be a solid state nanopore located in a solid-state membrane. The solid-state membrane itself can be the nanopore layer 110. Further alternatively, the nanopores can be biological nanopores located in a solid-state membrane. In light of the dimensions of the nanopore relative to the width of the channel, which is greater in diameter, a well can be said to form beneath the nanopore. The nanopore, therefore, defines a part of the passage 114 in each of the alternative nanopore configurations.

Any membrane may be used in accordance with various aspects described herein. An example membrane can comprise an amphiphilic layer or a solid-state layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer include, for example, block copolymers (Gonzalez-Perez et al., Langmuir, 2009, 25, 10447-10450). The copolymer may be a triblock, tetrablock or pentablock copolymer. The membrane can be a triblock or diblock copolymer membrane.

Membranes formed from block copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example, a hydrophobic polymer may be made from siloxane or other non-hydrocarbon-based monomers. The hydrophilic subsection of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer-based membranes for a wide range of applications.

The membrane can be one of the membranes disclosed in WO2014/064443 or WO2014/064444, each of which is hereby incorporated by reference in its entirety. These documents also disclose suitable polymers.

The amphiphilic molecules may be chemically-modified or functionalized to facilitate coupling of the polynucleotide.

The amphiphilic layer may be a monolayer or a bilayer. The amphiphilic layer can be planar (e.g., is planar). The amphiphilic layer may be curved. The amphiphilic layer may be supported. The amphiphilic layer may be concave. The amphiphilic layer may be suspended from raised pillars such that the peripheral region of the amphiphilic layer (which is attached to the pillars) is higher than the amphiphilic layer region. This may allow the microparticle to travel, move, slide or roll along the membrane as described above.

The membrane may be a lipid bilayer. Suitable lipid bilayers are disclosed in WO 2008/102121, WO 2009/077734 and WO 2006/100484.

Various methods for forming lipid bilayers may be used. For example, lipid bilayers can be formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid-state layer may be formed from graphene. Suitable graphene layers are disclosed in WO 2009/035647. Yusko et al., Nature Nanotechnology, 2011; 6: 253-260 and US Patent Application No. 2013/0048499 describe the delivery of proteins to transmembrane pores in solid state layers without the use of microparticles.

Any transmembrane pore may be used. The pore may be biological or artificial. Suitable pores include, but are not limited to, protein pores, polynucleotide pores and solid-state pores. The pore may be a DNA origami pore (Langecker et al., Science, 2012; 338: 932-936).

The transmembrane pore can be a transmembrane protein pore. A transmembrane protein pore is a polypeptide or a collection of polypeptides that permits hydrated ions, such as the by-products of processing a polynucleotide with a polymerase, to flow from one side of a membrane to the other side of the membrane. In one embodiment, the transmembrane protein pore is capable of forming a pore that permits hydrated ions driven by an applied potential to flow from one side of the membrane to the other. The transmembrane protein pore can permit polynucleotides to flow from one side of the membrane, such as a triblock copolymer membrane, to the other. The transmembrane protein pore may allow a polynucleotide, such as DNA or RNA, to be moved through the pore.

The transmembrane protein pore may be a monomer or an oligomer. The pore can be made up of several repeating subunits, such as at least 6, at least 7, at least 8, at least 9, at least 10, at least 11, at least 12, at least 13, at least 14, at least 15, or at least 16 subunits. The pore can be a hexameric, heptameric, octameric or nonameric pore. The pore may be a homo-oligomer or a hetero-oligomer.

According to some embodiments, the transmembrane protein pore comprises a barrel or channel through which the ions may flow. The subunits of the pore can surround (e.g., surround) a central axis and contribute strands to a transmembrane β barrel or channel or a transmembrane α-helix bundle or channel. The barrel or channel of the transmembrane protein pore can include (e.g., comprises) amino acids that facilitate interaction with nucleotides, polynucleotides or nucleic acids. These amino acids can be located near a constriction of the barrel or channel. The transmembrane protein pore can include (e.g., comprises) one or more positively charged amino acids, such as arginine, lysine or histidine, or aromatic amino acids, such as tyrosine or tryptophan. These amino acids may facilitate (e.g., facilitate) the interaction between the pore and nucleotides, polynucleotides or nucleic acids.

Transmembrane protein pores for use in accordance with the invention can be derived from β-barrel pores or α-helix bundle pores. The transmembrane pore may be derived from or based on Msp, α-hemolysin (α-HL), lysenin, CsgG, ClyA, Sp1 and hemolytic protein fragaceatoxin C (FraC). The transmembrane protein pore can be derived from CsgG. Suitable pores derived from CsgG are disclosed in WO 2016/034591. The transmembrane pore may be derived from lysenin. Suitable pores derived from lysenin are disclosed in WO 2013/153359.

The analytes (including, e.g., proteins, peptides, small molecules, polypeptide, polynucleotides) may be present in an analyte. The analyte may be any suitable sample. The analyte may be a biological sample. Any embodiment of the methods described herein may be carried out in vitro on an analyte obtained from or extracted from any organism or microorganism. The organism or microorganism can be (e.g., is) archaean, prokaryotic or eukaryotic and can belong (e.g., belongs) to one of the five kingdoms: plantae, animalia, fungi, monera and protista. In some embodiments, the methods of various aspects described herein may be carried out in vitro on an analyte obtained from or extracted from any virus.

The analyte can be a fluid sample. The analyte can comprise a body fluid. The body fluid may be obtained from a human or animal. The human or animal may have, be suspected of having or be at risk of a disease. The analyte may be urine, lymph, saliva, mucus, seminal fluid or amniotic fluid, but can be whole blood, plasma or serum. In some embodiments, the analyte is human in origin, but alternatively it may be from another mammal such as from commercially farmed animals such as horses, cattle, sheep or pigs or may alternatively be pets such as cats or dogs. Alternatively, an analyte can be of plant origin.

The analyte may be a non-biological sample. The non-biological sample can be a fluid sample. An ionic salt such as potassium chloride may be added to the sample to effect ion flow through the nanopore.

The polynucleotide may be single stranded or double stranded. At least a portion of the polynucleotide may be double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid, such as peptide nucleic acid (PNA), glycerol nucleic acid (GNA), threose nucleic acid (TNA), locked nucleic acid (LNA) or other synthetic polymers with nucleotide side chains. The polynucleotide can be any length.

Any number of polynucleotides can be investigated. For instance, the method may concern characterising 2, 3, 4, 5, 6, 7, 8, 9, 10, 20, 30, 50, 100 or more polynucleotides. If two or more polynucleotides are characterised, they may be different polynucleotides or two instances of the same polynucleotide.

The polynucleotide can be naturally occurring or artificial.

The method may involve measuring two, three, four or five or more characteristics of a polynucleotide. The one or more characteristics can be selected from (i) the length of the polynucleotide, (ii) the identity of the polynucleotide, (iii) the sequence of the polynucleotide, (iv) the secondary structure of the polynucleotide and (v) whether or not the polynucleotide is modified.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

The secondary structure may be measured in a variety of ways. For instance, if the method involves an electrical measurement, the secondary structure may be measured using a change in dwell time or a change in ion current flowing through the pore. This allows regions of single-stranded and double-stranded polynucleotide to be distinguished.

The presence or absence of any modification may be measured. The method can comprises determining whether or not the polynucleotide is modified by methylation, by oxidation, by damage, with one or more proteins or with one or more labels, tags or spacers. Specific modifications will result in specific interactions with the pore which can be measured using the methods described below.

In some embodiments of various aspects described herein, the method may involve further characterizing the target polynucleotide. As the target polynucleotide is contacted with the pore, one or more measurements which are indicative of one or more characteristics of the target polynucleotide are taken as the polynucleotide moves with respect to the pore.

The method may involve determining whether or not the polynucleotide is modified. The presence or absence of any modification may be measured. The method can comprises determining whether or not the polynucleotide is modified by methylation, by oxidation, by damage, with one or more proteins or with one or more labels, tags or spacers.

Also provided is a kit for characterising a target polynucleotide. The kit comprises a pore as disclosed herein and the components of a membrane. The membrane can be formed from the components. The pore can be present in the membrane. The kit may comprise components of any of the membranes disclosed above, such as an amphiphilic layer or a triblock copolymer membrane.

Also provided is an apparatus for characterising a target analyte, such as a target polynucleotide. The apparatus comprises a plurality of the pores as disclosed herein and a plurality of membranes. The plurality of pores can be present in the plurality of membranes. The number of pores and membranes can be equal. A single pore can be present in each membrane.

The apparatus for characterising target analytes, may comprise or an array of pores as disclosed herein, in a plurality of membranes.

The apparatus can further comprises instructions for carrying out the method. The apparatus may be any conventional apparatus for analyte analysis, such as an array or a chip. Any of the embodiments discussed above with reference to the methods are equally applicable to the apparatus of the invention. The apparatus may further comprise any of the features present in the kit as disclosed herein.

The apparatus can be set up to carry out a method as disclosed herein.

The apparatus can comprise: a sensor device that is capable of supporting the plurality of pores and membranes and being operable to perform analyte characterisation using the pores and membranes; and at least one port for delivery of the material for performing the characterisation.

Alternatively, the apparatus can comprise: a sensor device that is capable of supporting the plurality of pores and membranes being operable to perform analyte characterisation using the pores and membranes; and at least one reservoir for holding material for performing the characterisation.

The apparatus can comprise: a sensor device that is capable of supporting the membrane and plurality of pores and membranes and being operable to perform analyte characterising using the pores and membranes; at least one reservoir for holding material for performing the characterising; a fluidics system configured to controllably supply material from the at least one reservoir to the sensor device; and one or more containers for receiving respective samples, the fluidics system being configured to supply the analytes selectively from one or more containers to the sensor device.

The apparatus may be any of those described in WO 2009/077734, WO 2010/122293, WO 2011/067559 or WO 00/28312.

Control of the movement of an analyte with respect to the nanopore e.g. speed of translocation, rejection of the analyte etc., can be managed by the systems and methods disclosed in WO2016/059427, incorporated herein by reference in its entirety. Rejection of an analyte by the nanopore sensor can comprise ejection of the analyte from the nanopore.

The features in description above and in Figures of the invention are interchangeable and compatible in light of the teaching herein. The present invention has been described above purely by way of example, and modifications can be made within the spirit and scope of the invention, which extends to equivalents of the features described and combinations of one or more features described herein. The invention also consists in any individual features described or implicit herein.

| List of features: | |
|---|---|
| 2 | Sensor device |
| 4 | Solid-state pore |
| 6 | Sample |
| 8 | Body |
| 10 | Cis |
| 12 | Fluidic passage |
| 14 | Trans |
| 16 | Sensor |
| 18 | Electrodes |
| 100 | Structure |
| 101 | Nanopore sensor footprint |
| 102 | Nanopore sensor/pixel |
| 102a | Nanopore sensor module |
| 104 | Array of nanopore sensors |

| List of features: -continued | |
|---|---|
| 106 | Sample chamber/cis/first fluidic reservoir |
| 108 | Outlet chamber/trans/second fluidic reservoir |
| 110 | Nanopore layer |
| 112 | Base layer |
| 114 | Passage |
| 116 | Nanopore |
| 118 | Membrane |
| 120 | First end/pore end |
| 122 | Channel |
| 124 | Second end/channel end |
| 126 | sensor electrode |
| 128 | Connection/wire-bond |
| 130 | Electrical circuit |
| 132 | Drive electrodes |
| | (a) Cis electrode |
| | (b) Trans electrode |
| 134 | Cis-surface |
| 136 | Cis-plane |
| 138 | Trans-surface |
| 140 | Trans-plane |
| 142 | Well |
| 142a | Well aperture (well outlet) |
| 144 | Sense layer |
| 146 | Cavity |
| 148 | Sensor aperture |
| 149 | Device/Sensor device/Measurement system |
| 150 | Integrated circuit |
| 151 | Connector |
| 152 | Sensing circuit |
| 153 | Sensing transistor |
| 154 | Sensor terminal |
| 155 | Control circuit |
| 156 | Control transistor |
| 158 | Control circuit |
| 160 | Compensation circuit |
| 161 | Resistor Model |
| 162 | Stray capacitance |
| 164 | Flick/control switch |
| 166 | Guard switch |
| 168 | In-line amplifier |
| 170 | Feedback amplifier |
| 172 | Compensation capacitor |
| 174 | Select/row-column circuit |
| 176 | Row decoder |
| 178 | Column readout |
| 180 | ADC |
| 182 | Control electrode |
| 184 | Guard conductor |
| 192 | Oxide layers |
| 201 | First Schematic Circuit |
| 202 | Second Schematic Circuit |
| 203 | First Conductive Element |
| 204 | Second Conductive Element |
| 205 | Buffer |
| 210 | Printed Circuit Board |
| 212 | Mechanical Bond |
| 214 | Wire Bond |
| 216, 218 | Gaskets |
| 222 | Solder Bump Connection |
| 224, 226 | Flowcells |
| 228 | Gasket |
| 230 | Sealant |
| 232 | Gasket |

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A device for nanopore sensing, said device comprising:
a structure arranged to separate an analyte reservoir and an outlet chamber, the structure comprising an array of nanopore structures, one or more of the nanopore structures comprising a passage for fluid connection through the structure between the analyte reservoir and outlet chamber;
drive electrodes connected respectively in the analyte reservoir and the outlet chamber for imposing an electrical potential difference across the passage;
electrical transduction elements, each element connected to the passage of a respective nanopore structure for measuring the fluidic electrical potential at that electrical transduction element in that nanopore structure; and
control terminals, each terminal connected to a respective nanopore structure for applying a control signal to alter the electrical potential difference across that nanopore structure;
wherein the structure has:
a nanopore layer incorporating a nanopore and/or incorporating a well for supporting a nanopore; and
a base layer incorporating a channel,
wherein the nanopore layer and the base layer are sandwiched together such that the nanopore and/or well are aligned with the channel to define the passage;
wherein the device further comprises a sensor electrode formed on a sense layer, wherein the sense layer is sandwiched between the nanopore layer and the base layer.

2. A device according to claim 1, wherein the electrical transduction element and the control terminal associated with each nanopore structure are directly connected.

3. A device according to claim 1, wherein the terminals are configured to apply the control signal to alter the electrical potential difference across each respective nanopore structure in response to a measurement of the fluidic electrical potential at the electrical transduction element at that nanopore structure.

4. A device according to claim 1, wherein the application of the control signal is configured to alter the potential difference between at least one of the control terminals and at least one of the drive electrodes.

5. A device according to claim 1, wherein the control signal is connectable to a plurality of the nanopore structures to simultaneously alter the potential difference between the connected control terminals and at least one of the drive electrodes.

6. A device according to claim 1, wherein each electrical transduction element is isolatable from a measuring circuit.

7. A device according to claim 6, wherein the electrical transduction elements are isolatable prior to the application of the control signal.

8. A device according to claim 1, wherein the nanopore layer comprises a nanopore.

9. A device according to claim 8, wherein the control signal is applied for the purpose of altering the potential difference across the nanopore in order to:
 unblock the passage of a nanopore when the device detects that an analyte is blocked;
 reject an analyte being measured; and/or
 alter the direction and/or speed of translocation of an analyte through the nanopore.

10. A device according to claim 9, further comprising electronic circuits, wherein each electronic circuit is associated with a group of nanopore structures.

11. A device according to claim 10, wherein each control circuit is associated with a group of nanopore structures.

12. A device according to claim 11, wherein at least one of the electrical transduction element, the control circuit, or the control terminal is disposed on or between the outer surface of the structure.

13. A device according to claim 1, wherein the array has circuits, each circuit associated with a respective nanopore structure and connected to the electrical transduction element, each circuit configured to modify and/or process the signals received therefrom.

14. A device according to claim 1, wherein the array has circuits, each circuit associated with a respective nanopore structure and connected to the control terminal and/or the electrical transduction element, the circuit configured to alter at the respective nanopore structure an electrical potential imposed by the drive electrodes in response to a signal.

15. A device having nanopore structures for sensing an analyte, the nanopore structures configured in a structure, said structure arranged to separate an analyte reservoir and an outlet chamber, each nanopore structure providing a passage for fluid connection through the structure between the analyte reservoir and outlet chamber, wherein each nanopore structure comprises:
 an electrical transduction element; and
 an electronic circuit configured to detect a signal from the electrical transduction element, wherein each of the structures are configured to perform one of, or some combination of, store, transmit, process and communicate at least a portion of the signal to a connectable processor;
wherein the structure has:
a nanopore layer incorporating a nanopore and/or incorporating a well for supporting a nanopore; and
a base layer incorporating a channel,
wherein the nanopore layer and the base layer are sandwiched together such that the nanopore and/or well are aligned with the channel to define the passage;
wherein the device further comprises a sensor electrode formed on a sense layer, wherein the sense layer is sandwiched between the nanopore layer and the base layer.

16. A device having an array of nanopore structures configured in a sheet, the sheet comprising:
 a nanopore layer having an array of nanopores and/or an array of wells for supporting a nanopore; and
 a base layer having an array of channels, said base layer sandwiched to the nanopore layer to form the sheet, wherein the nanopores and/or the wells are aligned with the channels, wherein each of the nanopore structures comprise a passage, each passage defined at least in part by:
 one of the nanopores and/or one of the wells of the nanopore layer, at one side of the passage;
 a channel of the base layer at the other side of the passage; and
an electrical transduction element;
wherein the device further comprises a sensor electrode formed on a sense layer, wherein the sense layer is sandwiched between the nanopore layer and the base layer.

17. A method of operating a device for nanopore sensing, the method comprising:
 imposing an electrical potential difference across an array of nanopore sensors disposed in a structure separating an analyte reservoir and an outlet chamber, each nanopore sensor having a passage for providing a fluid connection between the analyte reservoir and the outlet chamber;
 providing an analyte for analysis by the nanopore sensors, each nanopore sensor having an electrical transduction element for measuring a change in the electrical potential at the electrical transduction element of that nanopore sensor when an analyte is induced through a nanopore of the nanopore sensor; and
 applying a control signal to a control terminal of an electrical transduction element of a nanopore sensor of the array to alter the electrical potential difference across that nanopore sensor;
wherein the structure has:
a nanopore layer incorporating a nanopore and/or incorporating a well for supporting a nanopore; and
a base layer incorporating a channel,
wherein the nanopore layer and the base layer are sandwiched together such that the nanopore and/or well are aligned with the channel to define the passage;
wherein the device further comprises a sensor electrode formed on a sense layer, wherein the sense layer is sandwiched between the nanopore layer and the base layer.

18. A method of forming a device having nanopore structures for sensing an analyte, the method comprising:
 forming nanopore structures in a structure and arranging said structure to separate an analyte reservoir and an outlet chamber of the device such that each nanopore structure provides a passage for fluid connection through the structure between the analyte reservoir and outlet chamber; and
 fabricating in each nanopore structure:
 an electrical transduction element; and
 an electronic circuit configured to measure a signal from the electrical transduction element,
wherein each of the nanopore structures are configured to at least one of store, transmit, process and communicate at least a portion of the measured signal, or information derived therefrom, to a connectable processor;

wherein the structure has:

a nanopore layer incorporating a nanopore and/or incorporating a well for supporting a nanopore; and a base layer incorporating a channel, wherein the nanopore layer and the base layer are sandwiched together such that the nanopore and/or well are aligned with the channel to define the passage;

wherein the device further comprises a sensor electrode formed on a sense layer, wherein the sense layer is sandwiched between the nanopore layer and the base layer.

19. A method of forming a device having an array of nanopore structures configured in a sheet, including arranging the sheet to separate an analyte reservoir and an outlet chamber of the device such that each nanopore structure provides a passage for fluid connection through the structure between the analyte reservoir and outlet chamber, the method comprising:

forming a nanopore layer having an array of nanopores and/or an array of wells for supporting a nanopore;

forming an array of electrical transduction elements;

forming a base layer having an array of channels, said base layer sandwiched to the nanopore layer to form the sheet such that the nanopores and/or the wells are aligned with the electrical transduction elements and channels; and providing a passage through each of the nanopore structures such that each passage is defined at least in part by:

one of the nanopores and/or one of the wells of the nanopore layer, at one side of the passage;

a channel of the base layer at the other side of the passage; and an electrical transduction element;

wherein the device further comprises a sensor electrode formed on a sense layer, wherein the sense layer is sandwiched between the nanopore layer and the base layer.

* * * * *